US012611121B2

(12) United States Patent
    Rao

(10) Patent No.:  US 12,611,121 B2
(45) Date of Patent:       Apr. 28, 2026

(54) SYSTEMS, DEVICES, AND METHODS FOR ANALYTE MONITORING

(71) Applicant: ABBOTT DIABETES CARE INC., Alameda, CA (US)

(72) Inventor: Vivek S. Rao, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 18/078,218

(22) Filed: Dec. 9, 2022

(65) Prior Publication Data

US 2023/0108476 A1      Apr. 6, 2023

Related U.S. Application Data

(63) Continuation of application No. 17/865,843, filed on Jul. 15, 2022, now abandoned.

(60) Provisional application No. 63/222,851, filed on Jul. 16, 2021.

(51) Int. Cl.
    *A61B 5/145*          (2006.01)
(52) U.S. Cl.
    CPC .... *A61B 5/14532* (2013.01); *A61B 2560/063* (2013.01)
(58) Field of Classification Search
    CPC . A61B 5/14503; A61B 5/1473; A61B 5/1486; A61B 5/14865; A61B 5/1451; A61B 2560/063
    See application file for complete search history.

(56) References Cited

U.S. PATENT DOCUMENTS

| | | | |
|---|---|---|---|
| 2,402,306 A | 6/1946 | Turkel | |
| 2,752,918 A | 7/1956 | Uytenbogaart | |
| 3,123,790 A | 3/1964 | Tyler | |
| 3,132,123 A | 5/1964 | Harris, Jr. et al. | |
| 3,173,200 A | 3/1965 | Dunmire et al. | |
| 3,211,001 A | 10/1965 | Petit | |
| 3,260,656 A | 7/1966 | Ross, Jr. | |
| 3,517,670 A | 6/1970 | Speelman | |
| 3,522,807 A | 8/1970 | Millenbach | |
| 3,581,062 A | 5/1971 | Aston | |

(Continued)

FOREIGN PATENT DOCUMENTS

| | | |
|---|---|---|
| AU | 2003259741 | 2/2004 |
| CA | 2291105 | 12/1998 |

(Continued)

OTHER PUBLICATIONS

AU, 2007309066 Examiner's Report, dated Jul. 12, 2012.

(Continued)

*Primary Examiner* — Eric J Messersmith

(74) *Attorney, Agent, or Firm* — ONE LLP

(57) ABSTRACT

Disclosed herein are various embodiments of sensor applicator assemblies for delivering sensor control devices, wherein the embodiments include features for improving the longevity of the sensor applicator or sensor control device, as well as reducing the likelihood of mechanical failure of certain components. Some embodiments include, for example, a pull-tab coupled with the sensor or battery, an adhesive liner for the sensor control device, one or more magnets for retaining the sensor control device in the sensor carrier, and a leaf spring retraction mechanism.

13 Claims, 23 Drawing Sheets

(56)                References Cited

U.S. PATENT DOCUMENTS

| | | |
|---|---|---|
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,960,497 A | 6/1976 | Acord et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,033,330 A | 7/1977 | Willis et al. |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,203,446 A | 5/1980 | Hofert et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,294,258 A | 10/1981 | Bernard |
| 4,305,401 A | 12/1981 | Reissmueller et al. |
| 4,308,981 A | 1/1982 | Miura |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,392,849 A | 7/1983 | Petre et al. |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatasetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,553,541 A | 11/1985 | Burns |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,592,745 A | 6/1986 | Rex et al. |
| 4,595,011 A | 6/1986 | Phillips |
| 4,619,754 A | 10/1986 | Niki et al. |
| 4,619,793 A | 10/1986 | Lee |
| 4,622,966 A | 11/1986 | Beard |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardieri |
| 4,637,403 A | 1/1987 | Garcia et al. |
| 4,639,062 A | 1/1987 | Taniguchi et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,663,824 A | 5/1987 | Kenmochi |
| 4,665,906 A | 5/1987 | Jervis |
| 4,671,288 A | 6/1987 | Gough |
| 4,675,346 A | 6/1987 | Lin et al. |
| 4,679,562 A | 7/1987 | Luksha |
| 4,680,268 A | 7/1987 | Clark, Jr. |
| 4,682,602 A | 7/1987 | Prohaska |
| 4,684,245 A | 8/1987 | Goldring |
| 4,684,537 A | 8/1987 | Graetzel et al. |
| 4,685,463 A | 8/1987 | Williams |
| 4,685,466 A | 8/1987 | Rau |
| 4,690,675 A | 9/1987 | Katz |
| 4,698,057 A | 10/1987 | Joishy |
| 4,703,324 A | 10/1987 | White |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,683 A | 11/1988 | Wozniak et al. |
| 4,781,798 A | 11/1988 | Gough |
| 4,784,736 A | 11/1988 | Lonsdale et al. |
| 4,785,868 A | 11/1988 | Koenig, Jr. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,817,603 A | 4/1989 | Turner et al. |
| 4,818,994 A | 4/1989 | Orth et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,847,785 A | 7/1989 | Stephens |
| 4,848,351 A | 7/1989 | Finch |
| 4,852,025 A | 7/1989 | Herpichböhm |
| 4,854,322 A | 8/1989 | Ash et al. |
| 4,856,648 A | 8/1989 | Krueger |

(56)                    References Cited

U.S. PATENT DOCUMENTS

| | | | |
|---|---|---|---|
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,924,879 A | 5/1990 | O'Brien |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagata |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,985,142 A | 1/1991 | Laycock et al. |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,006,110 A | 4/1991 | Garrison et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,051,688 A | 9/1991 | Murase et al. |
| 5,055,171 A | 10/1991 | Peck |
| 5,058,592 A | 10/1991 | Whisler |
| 5,067,957 A | 11/1991 | Jervis |
| 5,068,536 A | 11/1991 | Rosenthal |
| 5,070,535 A | 12/1991 | Hochmair et al. |
| 5,082,550 A | 1/1992 | Rishpon et al. |
| 5,082,786 A | 1/1992 | Nakamoto |
| 5,086,246 A | 2/1992 | Dymond et al. |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,124,661 A | 6/1992 | Zelin et al. |
| 5,126,034 A | 6/1992 | Carter et al. |
| 5,133,856 A | 7/1992 | Yamaguchi et al. |
| 5,135,003 A | 8/1992 | Souma |
| 5,135,004 A | 8/1992 | Adams et al. |
| 5,140,985 A | 8/1992 | Schroeder et al. |
| 5,141,868 A | 8/1992 | Shanks et al. |
| 5,161,532 A | 11/1992 | Joseph |
| 5,162,407 A | 11/1992 | Turner |
| 5,165,407 A | 11/1992 | Wilson et al. |
| 5,173,165 A | 12/1992 | Schmid et al. |
| 5,174,291 A | 12/1992 | Schoonen et al. |
| 5,190,041 A | 3/1993 | Palti |
| 5,190,546 A | 3/1993 | Jervis |
| 5,192,416 A | 3/1993 | Wang et al. |
| 5,193,545 A | 3/1993 | Marsoner et al. |
| 5,198,367 A | 3/1993 | Aizawa et al. |
| 5,202,261 A | 4/1993 | Musho et al. |
| 5,204,264 A | 4/1993 | Kaminer et al. |
| 5,205,297 A | 4/1993 | Montecalvo et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,228,449 A | 7/1993 | Christ et al. |
| 5,229,282 A | 7/1993 | Yoshioka et al. |
| 5,231,988 A | 8/1993 | Wernicke et al. |
| 5,234,835 A | 8/1993 | Nestor et al. |
| 5,238,729 A | 8/1993 | Debe |
| 5,243,696 A | 9/1993 | Carr et al. |
| 5,245,314 A | 9/1993 | Kah et al. |
| 5,246,867 A | 9/1993 | Lakowicz et al. |
| 5,250,439 A | 10/1993 | Musho et al. |
| 5,251,126 A | 10/1993 | Kahn et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,267,963 A | 12/1993 | Bachynsky |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jackobson et al. |
| 5,293,546 A | 3/1994 | Tadros et al. |
| 5,293,877 A | 3/1994 | O'Hara et al. |
| 5,299,571 A | 4/1994 | Mastrototaro |
| 5,305,008 A | 4/1994 | Turner et al. |
| 5,318,583 A | 6/1994 | Rabenau et al. |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,333,615 A | 8/1994 | Craelius et al. |
| 5,337,747 A | 8/1994 | Neftel |
| 5,340,722 A | 8/1994 | Wolfbeis et al. |
| 5,342,789 A | 8/1994 | Chick et al. |
| 5,352,348 A | 10/1994 | Young et al. |
| 5,356,420 A | 10/1994 | Czernecki et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,384,547 A | 1/1995 | Lynk et al. |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,394,877 A | 3/1995 | Orr et al. |
| 5,395,504 A | 3/1995 | Saurer et al. |
| 5,400,782 A | 3/1995 | Beaubiah |
| 5,400,794 A | 3/1995 | Gorman |
| 5,402,780 A | 4/1995 | Faasse, Jr. |
| 5,407,431 A | 4/1995 | Botich et al. |
| 5,408,999 A | 4/1995 | Singh et al. |
| 5,410,326 A | 4/1995 | Goldstein |
| 5,411,647 A | 5/1995 | Johnson et al. |
| 5,425,361 A | 6/1995 | Fenzlein et al. |
| 5,425,868 A | 6/1995 | Pedersen |
| 5,431,160 A | 7/1995 | Wilkins |
| 5,431,921 A | 7/1995 | Thombre |
| 5,437,999 A | 8/1995 | Diebold et al. |

(56) References Cited

U.S. PATENT DOCUMENTS

| | | |
|---|---|---|
| 5,438,983 A | 8/1995 | Falcone |
| 5,462,051 A | 10/1995 | Oka et al. |
| 5,462,645 A | 10/1995 | Albery et al. |
| 5,469,846 A | 11/1995 | Khan |
| 5,472,317 A | 12/1995 | Field et al. |
| 5,482,473 A | 1/1996 | Lord et al. |
| 5,484,403 A | 1/1996 | Yoakum et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,516,832 A | 5/1996 | Kennan et al. |
| 5,527,288 A | 6/1996 | Gross et al. |
| 5,531,878 A | 7/1996 | Vadgama et al. |
| 5,532,686 A | 7/1996 | Urbas et al. |
| 5,533,977 A | 7/1996 | Metcalf et al. |
| 5,536,259 A | 7/1996 | Utterberg |
| 5,543,326 A | 8/1996 | Heller et al. |
| 5,544,196 A | 8/1996 | Tiedmann, Jr. et al. |
| 5,545,191 A | 8/1996 | Mann et al. |
| 5,549,568 A | 8/1996 | Sheilds |
| 5,551,427 A | 9/1996 | Altman |
| 5,555,190 A | 9/1996 | Derby et al. |
| 5,558,638 A | 9/1996 | Evers et al. |
| 5,560,357 A | 10/1996 | Faupei et al. |
| 5,562,713 A | 10/1996 | Silvian |
| 5,564,434 A | 10/1996 | Halperin et al. |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,571,022 A | 11/1996 | Schaarschmidt |
| 5,575,563 A | 11/1996 | Chiu et al. |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,597,378 A | 1/1997 | Jervis |
| 5,600,301 A | 2/1997 | Robinson, III |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,623,933 A | 4/1997 | Amano et al. |
| 5,626,566 A | 5/1997 | Petersen et al. |
| 5,628,310 A | 5/1997 | Rao et al. |
| 5,628,324 A | 5/1997 | Sarbach |
| 5,628,890 A | 5/1997 | Carter et al. |
| 5,632,557 A | 5/1997 | Simons |
| 5,634,468 A | 6/1997 | Platt et al. |
| 5,636,640 A | 6/1997 | Staehlin |
| 5,638,832 A | 6/1997 | Singer et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,071 A | 9/1997 | Wyrick |
| 5,665,222 A | 9/1997 | Heller et al. |
| 5,669,543 A | 9/1997 | Ueno |
| 5,669,890 A | 9/1997 | Grimm |
| 5,670,031 A | 9/1997 | Hintsche et al. |
| 5,673,322 A | 9/1997 | Pepe et al. |
| 5,680,858 A | 10/1997 | Hansen et al. |
| 5,682,233 A | 10/1997 | Brinda |
| 5,695,623 A | 12/1997 | Michel et al. |
| 5,707,502 A | 1/1998 | McCaffrey et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,724,030 A | 3/1998 | Urbas et al. |
| 5,726,646 A | 3/1998 | Bane et al. |
| 5,733,044 A | 3/1998 | Rose et al. |
| 5,733,259 A | 3/1998 | Valcke et al. |
| 5,733,262 A | 3/1998 | Paul |
| 5,733,313 A | 3/1998 | Barreras, Sr. et al. |
| 5,735,285 A | 4/1998 | Albert et al. |
| 5,738,220 A | 4/1998 | Geszler |
| 5,741,211 A | 4/1998 | Renirie et al. |
| 5,743,262 A | 4/1998 | Lepper, Jr. et al. |
| 5,746,217 A | 5/1998 | Erickson et al. |
| 5,746,697 A | 5/1998 | Swedlow et al. |
| 5,748,103 A | 5/1998 | Flach et al. |
| 5,749,656 A | 5/1998 | Boehm et al. |
| 5,749,907 A | 5/1998 | Mann |
| 5,758,290 A | 5/1998 | Nealon et al. |
| 5,766,131 A | 6/1998 | Kondo et al. |
| 5,770,028 A | 6/1998 | Maley et al. |
| 5,771,001 A | 6/1998 | Cobb |
| 5,771,891 A | 6/1998 | Gozani |
| 5,772,586 A | 6/1998 | Heinonen et al. |
| 5,778,879 A | 7/1998 | Ota et al. |
| 5,779,665 A | 7/1998 | Mastrototaro et al. |
| 5,786,439 A | 7/1998 | Van Antwerp et al. |
| 5,791,344 A | 8/1998 | Schulman et al. |
| 5,798,961 A | 8/1998 | Heyden et al. |
| 5,800,420 A | 9/1998 | Gross et al. |
| 5,804,047 A | 9/1998 | Karube et al. |
| 5,807,375 A | 9/1998 | Gross et al. |
| 5,814,020 A | 9/1998 | Gross |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,823,802 A | 10/1998 | Bartley |
| 5,827,184 A | 10/1998 | Netherly et al. |
| 5,830,064 A | 11/1998 | Bradish et al. |
| 5,833,603 A | 11/1998 | Kovacs et al. |
| 5,840,020 A | 11/1998 | Heinonen et al. |
| 5,842,983 A | 12/1998 | Abel et al. |
| 5,851,197 A | 12/1998 | Marano et al. |
| 5,856,758 A | 1/1999 | Joffe et al. |
| 5,858,001 A | 1/1999 | Tsals et al. |
| 5,865,804 A | 2/1999 | Bachynsky |
| 5,871,494 A | 2/1999 | Simons et al. |
| 5,875,186 A | 2/1999 | Belanger et al. |
| 5,879,311 A | 3/1999 | Duchon et al. |
| 5,885,211 A | 3/1999 | Eppstein et al. |
| 5,891,049 A | 4/1999 | Cyrus et al. |
| 5,899,855 A | 5/1999 | Brown |
| 5,899,856 A | 5/1999 | Schoendorfer et al. |
| 5,914,026 A | 6/1999 | Blubaugh, Jr. et al. |
| 5,918,603 A | 7/1999 | Brown |
| 5,919,141 A | 7/1999 | Money et al. |
| 5,921,963 A | 7/1999 | Erez et al. |
| 5,924,979 A | 7/1999 | Swedlow et al. |
| 5,925,021 A | 7/1999 | Castellano et al. |
| 5,931,814 A | 8/1999 | Alex et al. |
| 5,931,868 A | 8/1999 | Gross |
| 5,935,224 A | 8/1999 | Svancarek et al. |
| 5,938,679 A | 8/1999 | Freeman et al. |
| 5,942,979 A | 8/1999 | Luppino |
| 5,948,006 A | 9/1999 | Mann |
| 5,951,485 A | 9/1999 | Cyrus et al. |
| 5,951,492 A | 9/1999 | Douglas et al. |
| 5,951,521 A | 9/1999 | Mastrototaro et al. |
| 5,951,582 A | 9/1999 | Thorne et al. |
| 5,954,643 A | 9/1999 | Van Antwerp |
| 5,954,685 A | 9/1999 | Tierny |
| 5,957,854 A | 9/1999 | Besson et al. |
| 5,961,451 A | 10/1999 | Reber et al. |
| 5,964,718 A | 10/1999 | Duchon et al. |

(56) References Cited

U.S. PATENT DOCUMENTS

| | | | |
|---|---|---|---|
| 5,964,993 A | 10/1999 | Blubaugh, Jr. et al. |
| 5,965,380 A | 10/1999 | Heller et al. |
| 5,971,922 A | 10/1999 | Arita et al. |
| 5,971,941 A | 10/1999 | Simons et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,315 A | 2/2000 | Iliff |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,028,413 A | 2/2000 | Brockmann |
| 6,032,064 A | 2/2000 | Devlin et al. |
| 6,036,924 A | 3/2000 | Simons et al. |
| 6,048,352 A | 4/2000 | Douglas et al. |
| 6,049,727 A | 4/2000 | Crothall |
| 6,052,565 A | 4/2000 | Ishikura et al. |
| 6,054,194 A | 4/2000 | Kane |
| 6,056,718 A | 5/2000 | Funderburk et al. |
| 6,059,946 A | 5/2000 | Yukawa et al. |
| 6,066,243 A | 5/2000 | Anderson et al. |
| 6,068,399 A | 5/2000 | Tseng |
| 6,071,294 A | 6/2000 | Simons et al. |
| 6,071,391 A | 6/2000 | Gotoh et al. |
| 6,083,710 A | 7/2000 | Heller et al. |
| 6,085,342 A | 7/2000 | Marholev et al. |
| 6,088,605 A | 7/2000 | Griffith et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,097,480 A | 8/2000 | Kaplan |
| 6,099,484 A | 8/2000 | Douglas et al. |
| 6,102,896 A | 8/2000 | Roser |
| 6,103,033 A | 8/2000 | Say et al. |
| 6,106,484 A | 8/2000 | Terwilliger |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,666 A | 10/2000 | DeLuca et al. |
| 6,130,623 A | 10/2000 | MacLellan et al. |
| 6,132,449 A | 10/2000 | Lum et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,144,922 A | 11/2000 | Douglas et al. |
| 6,149,626 A | 11/2000 | Bachynsky et al. |
| 6,157,850 A | 12/2000 | Diab et al. |
| 6,159,147 A | 12/2000 | Lichter et al. |
| 6,159,181 A | 12/2000 | Crossman et al. |
| 6,161,095 A | 12/2000 | Brown |
| 6,162,611 A | 12/2000 | Heller et al. |
| 6,168,606 B1 | 1/2001 | Levin et al. |
| 6,175,752 B1 | 1/2001 | Say et al. |
| 6,186,982 B1 | 2/2001 | Gross et al. |
| 6,192,891 B1 | 2/2001 | Gravel et al. |
| 6,197,040 B1 | 3/2001 | LeVaughn et al. |
| 6,198,946 B1 | 3/2001 | Shin et al. |
| 6,200,265 B1 | 3/2001 | Walsh et al. |
| 6,203,495 B1 | 3/2001 | Bardy et al. |
| 6,212,416 B1 | 4/2001 | Ward et al. |
| 6,213,972 B1 | 4/2001 | Butterfield et al. |
| 6,219,574 B1 | 4/2001 | Cormier et al. |
| 6,223,283 B1 | 4/2001 | Chaiken et al. |
| 6,231,531 B1 | 5/2001 | Lum et al. |
| 6,233,471 B1 | 5/2001 | Berner et al. |
| 6,237,394 B1 | 5/2001 | Harris et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,264,810 B1 | 7/2001 | Stol et al. |
| 6,270,455 B1 | 8/2001 | Brown |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,347 B1 | 10/2001 | Pompei |
| 6,299,757 B1 | 10/2001 | Feldman et al. |
| 6,302,866 B1 | 10/2001 | Marggi |
| 6,304,766 B1 | 10/2001 | Colvin, Jr. |
| 6,306,104 B1 | 10/2001 | Cunningham et al. |
| 6,306,141 B1 | 10/2001 | Jervis |
| 6,309,884 B1 | 10/2001 | Cooper et al. |
| 6,314,317 B1 | 11/2001 | Willis |
| 6,329,161 B1 | 12/2001 | Heller et al. |
| 6,331,244 B1 | 12/2001 | Lewis et al. |
| 6,336,269 B1 | 1/2002 | Eldridge et al. |
| 6,338,790 B1 | 1/2002 | Feldman et al. |
| 6,341,232 B1 | 1/2002 | Conn et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,364,890 B1 | 4/2002 | Lum et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,368,339 B1 | 4/2002 | Amplatz |
| 6,377,828 B1 | 4/2002 | Chaiken et al. |
| 6,377,829 B1 | 4/2002 | Al-Ali |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,409,740 B1 | 6/2002 | Kuhr et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Roques |
| 6,438,414 B1 | 8/2002 | Conn et al. |
| 6,440,068 B1 | 8/2002 | Brown et al. |
| 6,442,413 B1 | 8/2002 | Silver |
| 6,445,374 B2 | 9/2002 | Albert et al. |
| 6,451,025 B1 | 9/2002 | Jervis |
| 6,458,109 B1 | 10/2002 | Henley et al. |
| 6,461,496 B1 | 10/2002 | Feldman et al. |
| 6,471,689 B1 | 10/2002 | Joseph et al. |
| 6,472,220 B1 | 10/2002 | Simons et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,493,069 B1 | 12/2002 | Nagashimada et al. |
| 6,494,830 B1 | 12/2002 | Wessel |
| 6,496,729 B2 | 12/2002 | Thompson |
| 6,497,655 B1 | 12/2002 | Linberg et al. |
| 6,503,381 B1 | 1/2003 | Gotoh et al. |
| 6,510,344 B1 | 1/2003 | Halpern |
| 6,514,460 B1 | 2/2003 | Fendrock |
| 6,514,689 B2 | 2/2003 | Han et al. |

(56) References Cited

U.S. PATENT DOCUMENTS

| | | |
|---|---|---|
| 6,514,718 B2 | 2/2003 | Heller et al. |
| 6,520,326 B2 | 2/2003 | McIvor et al. |
| 6,522,927 B1 | 2/2003 | Bishay et al. |
| 6,533,805 B1 | 3/2003 | Jervis |
| 6,537,242 B1 | 3/2003 | Palmer |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,551,496 B1 | 4/2003 | Moles et al. |
| 6,554,795 B2 | 4/2003 | Bagaoisan et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,572,566 B2 | 6/2003 | Effenhauser |
| 6,574,490 B2 | 6/2003 | Abbink et al. |
| 6,574,510 B2 | 6/2003 | Von Arx et al. |
| 6,575,895 B1 | 6/2003 | Blair |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,602,268 B2 | 8/2003 | Kuhr et al. |
| 6,603,995 B1 | 8/2003 | Carter |
| 6,604,050 B2 | 8/2003 | Trippel et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,543 B2 | 8/2003 | Purcell et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,613,015 B2 | 9/2003 | Sandstrom et al. |
| 6,616,819 B1 | 9/2003 | Liamos et al. |
| 6,618,934 B1 | 9/2003 | Feldman et al. |
| 6,627,154 B1 | 9/2003 | Goodman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,637,611 B2 | 10/2003 | Luch |
| 6,641,533 B2 | 11/2003 | Causey, III et al. |
| 6,645,359 B1 | 11/2003 | Bhullar et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,662,439 B1 | 12/2003 | Bhullar |
| 6,666,849 B2 | 12/2003 | Marshall et al. |
| 6,668,196 B1 | 12/2003 | Villegas et al. |
| 6,671,534 B2 | 12/2003 | Putz |
| 6,675,030 B2 | 1/2004 | Ciurczak et al. |
| 6,676,290 B1 | 1/2004 | Lu |
| 6,676,816 B2 | 1/2004 | Mao et al. |
| 6,682,546 B2 | 1/2004 | Amplatz |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,699,188 B2 | 3/2004 | Wessel |
| 6,702,857 B2 | 3/2004 | Brauker et al. |
| 6,706,159 B2 | 3/2004 | Moerman et al. |
| 6,721,582 B2 | 4/2004 | Trepagnier et al. |
| 6,730,025 B1 | 5/2004 | Platt |
| 6,730,072 B2 | 5/2004 | Shawgo et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,748,445 B1 | 6/2004 | Darcey et al. |
| 6,749,740 B2 | 6/2004 | Liamos et al. |
| 6,758,810 B2 | 7/2004 | Lebel et al. |
| 6,758,835 B2 | 7/2004 | Close et al. |
| 6,764,581 B1 | 7/2004 | Forrow et al. |
| 6,767,440 B1 | 7/2004 | Bhullar et al. |
| 6,770,030 B1 | 8/2004 | Schaupp et al. |
| 6,773,671 B1 | 8/2004 | Lewis et al. |
| 6,781,522 B2 | 8/2004 | Sleva et al. |
| 6,790,178 B1 | 9/2004 | Mault et al. |
| 6,804,558 B2 | 10/2004 | Haller et al. |
| 6,804,561 B2 | 10/2004 | Stover |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,844 B2 | 11/2004 | Bhullar et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Uchigaki et al. |
| 6,850,790 B2 | 2/2005 | Berner et al. |
| 6,850,859 B1 | 2/2005 | Schuh |
| 6,854,882 B2 | 2/2005 | Chen |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,925,393 B1 | 8/2005 | Kalatz et al. |
| 6,931,327 B2 | 8/2005 | Goode, Jr. et al. |
| 6,932,892 B2 | 8/2005 | Chen |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,959,211 B2 | 10/2005 | Rule et al. |
| 6,960,192 B1 | 11/2005 | Flaherty et al. |
| 6,968,294 B2 | 11/2005 | Gutta et al. |
| 6,971,274 B2 | 12/2005 | Olin |
| 6,971,999 B2 | 12/2005 | Py et al. |
| 6,973,706 B2 | 12/2005 | Say et al. |
| 6,974,437 B2 | 12/2005 | Lebel et al. |
| 6,975,893 B2 | 12/2005 | Say et al. |
| 6,983,867 B1 | 1/2006 | Fugere |
| 6,990,366 B2 | 1/2006 | Say et al. |
| 6,997,907 B2 | 2/2006 | Safabash et al. |

(56) References Cited

U.S. PATENT DOCUMENTS

| | | | |
|---|---|---|---|
| 6,998,247 | B2 | 2/2006 | Monfre et al. |
| 6,999,854 | B2 | 2/2006 | Roth |
| 7,003,336 | B2 | 2/2006 | Holker et al. |
| 7,003,340 | B2 | 2/2006 | Say et al. |
| 7,003,341 | B2 | 2/2006 | Say et al. |
| 7,005,857 | B2 | 2/2006 | Stiene et al. |
| 7,009,511 | B2 | 3/2006 | Mazar et al. |
| 7,010,356 | B2 | 3/2006 | Jog et al. |
| 7,015,817 | B2 | 3/2006 | Copley et al. |
| 7,016,713 | B2 | 3/2006 | Gardner et al. |
| 7,020,508 | B2 | 3/2006 | Stivoric et al. |
| 7,022,072 | B2 | 4/2006 | Fox et al. |
| 7,022,219 | B2 | 4/2006 | Mansouri et al. |
| 7,024,236 | B2 | 4/2006 | Ford et al. |
| 7,024,245 | B2 | 4/2006 | Lebel et al. |
| 7,025,743 | B2 | 4/2006 | Mann et al. |
| 7,025,774 | B2 | 4/2006 | Freeman et al. |
| 7,027,848 | B2 | 4/2006 | Robinson et al. |
| 7,027,859 | B1 | 4/2006 | McNichols et al. |
| 7,027,931 | B1 | 4/2006 | Jones et al. |
| 7,029,444 | B2 | 4/2006 | Shin et al. |
| 7,041,057 | B1 | 5/2006 | Faupel et al. |
| 7,041,068 | B2 | 5/2006 | Freeman et al. |
| 7,041,468 | B2 | 5/2006 | Drucker et al. |
| 7,043,305 | B2 | 5/2006 | Kenknight et al. |
| 7,046,153 | B2 | 5/2006 | Oja et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,073,246 | B2 | 7/2006 | Bhullar et al. |
| 7,074,307 | B2 | 7/2006 | Simpson et al. |
| 7,081,195 | B2 | 7/2006 | Simpson et al. |
| 7,082,334 | B2 | 7/2006 | Boute et al. |
| 7,097,637 | B2 | 8/2006 | Triplett et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,118,667 | B2 | 10/2006 | Lee |
| 7,120,483 | B2 | 10/2006 | Russel et al. |
| 7,123,950 | B2 | 10/2006 | Mannheimer |
| 7,124,027 | B1 | 10/2006 | Ernst et al. |
| 7,125,382 | B2 | 10/2006 | Zhou et al. |
| 7,131,984 | B2 | 11/2006 | Sato et al. |
| 7,134,999 | B2 | 11/2006 | Brauker et al. |
| 7,136,689 | B2 | 11/2006 | Shults et al. |
| 7,144,384 | B2 | 12/2006 | Gorman et al. |
| 7,146,202 | B2 | 12/2006 | Ward et al. |
| 7,154,398 | B2 | 12/2006 | Chen et al. |
| 7,155,290 | B2 | 12/2006 | Von Arx et al. |
| 7,167,818 | B2 | 1/2007 | Brown |
| 7,169,600 | B2 | 1/2007 | Hoss et al. |
| 7,171,274 | B2 | 1/2007 | Starkweather et al. |
| 7,174,199 | B2 | 2/2007 | Berner et al. |
| 7,179,226 | B2 | 2/2007 | Crothall et al. |
| 7,183,102 | B2 | 2/2007 | Monfre et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,207,974 | B2 | 4/2007 | Safabash et al. |
| 7,220,387 | B2 | 5/2007 | Flaherty et al. |
| 7,223,276 | B2 | 5/2007 | List et al. |
| 7,225,535 | B2 | 6/2007 | Feldman et al. |
| 7,226,442 | B2 | 6/2007 | Sheppard et al. |
| 7,226,978 | B2 | 6/2007 | Tapsak et al. |
| 7,228,162 | B2 | 6/2007 | Ward et al. |
| 7,228,182 | B2 | 6/2007 | Healy et al. |
| 7,237,712 | B2 | 7/2007 | DeRocco et al. |
| 7,267,665 | B2 | 9/2007 | Steil et al. |
| 7,276,029 | B2 | 10/2007 | Goode, Jr. et al. |
| 7,276,146 | B2 | 10/2007 | Wilsey |
| 7,276,147 | B2 | 10/2007 | Wilsey |
| 7,278,983 | B2 | 10/2007 | Ireland et al. |
| 7,286,894 | B1 | 10/2007 | Grant et al. |
| 7,287,318 | B2 | 10/2007 | Bhullar et al. |
| 7,291,497 | B2 | 11/2007 | Holmes et al. |
| 7,295,867 | B2 | 11/2007 | Berner et al. |
| 7,297,151 | B2 | 11/2007 | Boecker et al. |
| 7,299,082 | B2 | 11/2007 | Feldman et al. |
| 7,310,544 | B2 | 12/2007 | Brister et al. |
| 7,318,816 | B2 | 1/2008 | Bobroff et al. |
| 7,324,012 | B2 | 1/2008 | Mann et al. |
| 7,324,850 | B2 | 1/2008 | Persen et al. |
| 7,329,239 | B2 | 2/2008 | Safabash et al. |
| 7,335,294 | B2 | 2/2008 | Heller et al. |
| 7,340,287 | B2 | 3/2008 | Mason et al. |
| 7,340,309 | B2 | 3/2008 | Miazga et al. |
| 7,344,500 | B2 | 3/2008 | Talbot et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,381,184 | B2 | 6/2008 | Funderburk et al. |
| 7,384,397 | B2 | 6/2008 | Zhang et al. |
| 7,386,937 | B2 | 6/2008 | Bhullar et al. |
| 7,387,010 | B2 | 6/2008 | Sunshine et al. |
| 7,399,277 | B2 | 7/2008 | Saidara et al. |
| 7,400,111 | B2 | 7/2008 | Batman et al. |
| 7,401,111 | B1 | 7/2008 | Batman et al. |
| 7,402,153 | B2 | 7/2008 | Steil et al. |
| 7,404,796 | B2 | 7/2008 | Ginsberg |
| 7,407,493 | B2 | 8/2008 | Cane |
| 7,408,132 | B2 | 8/2008 | Wambsganss et al. |
| 7,416,541 | B2 | 8/2008 | Yuzhakov et al. |
| 7,419,573 | B2 | 9/2008 | Gundel |
| 7,424,318 | B2 | 9/2008 | Brister et al. |
| 7,429,255 | B2 | 9/2008 | Thompson |
| 7,433,727 | B2 | 10/2008 | Ward |
| 7,448,996 | B2 | 11/2008 | Khanuja et al. |
| 7,455,663 | B2 | 11/2008 | Bikovsky |
| 7,460,898 | B2 | 12/2008 | Brister et al. |
| 7,462,264 | B2 | 12/2008 | Heller et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,476,827 | B1 | 1/2009 | Bhullar et al. |
| 7,481,819 | B2 | 1/2009 | Koeppel et al. |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,519,408 | B2 | 4/2009 | Rasdal et al. |
| 7,545,272 | B2 | 6/2009 | Goodnow et al. |
| 7,547,281 | B2 | 6/2009 | Hayes et al. |
| 7,565,197 | B2 | 7/2009 | Haubrich et al. |
| 7,568,619 | B2 | 8/2009 | Todd et al. |
| 7,569,030 | B2 | 8/2009 | Lebel et al. |
| 7,574,266 | B2 | 8/2009 | Dudding et al. |
| 7,582,059 | B2 | 9/2009 | Funderburk et al. |
| 7,583,990 | B2 | 9/2009 | Goode, Jr. et al. |
| 7,585,287 | B2 | 9/2009 | Bresina et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,604,592 | B2 | 10/2009 | Freeman et al. |
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,048 | B2 | 12/2009 | Dobbles et al. |
| 7,643,798 | B2 | 1/2010 | Ljung |
| 7,651,596 | B2 | 1/2010 | Petisce et al. |
| 7,651,845 | B2 | 1/2010 | Doyle, III et al. |
| 7,653,425 | B2 | 1/2010 | Hayter et al. |
| 7,654,956 | B2 | 2/2010 | Brister et al. |
| 7,657,297 | B2 | 2/2010 | Simpson et al. |
| 7,659,823 | B1 | 2/2010 | Killian et al. |
| 7,660,615 | B2 | 2/2010 | VanAntwerp et al. |

(56)     References Cited

U.S. PATENT DOCUMENTS

| | | |
|---|---|---|
| 7,666,149 B2 | 2/2010 | Simons et al. |
| 7,668,596 B2 | 2/2010 | Von Arx et al. |
| 7,682,338 B2 | 3/2010 | Griffin |
| 7,697,967 B2 | 4/2010 | Stafford |
| 7,699,775 B2 | 4/2010 | Desai et al. |
| 7,699,807 B2 | 4/2010 | Faust et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,729,737 B2 | 6/2010 | Ward |
| 7,731,657 B2 | 6/2010 | Stafford |
| 7,731,691 B2 | 6/2010 | Cote et al. |
| 7,736,310 B2 | 6/2010 | Taub et al. |
| 7,736,344 B2 | 6/2010 | Moberg et al. |
| 7,741,734 B2 | 6/2010 | Joannopoulos et al. |
| 7,763,042 B2 | 7/2010 | Iio et al. |
| 7,766,829 B2 | 8/2010 | Sloan et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,680 B2 | 8/2010 | Goode, Jr. et al. |
| 7,779,332 B2 | 8/2010 | Karr et al. |
| 7,780,827 B1 | 8/2010 | Bhullar et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,826,981 B2 | 11/2010 | Goode, Jr. et al. |
| 7,831,310 B2 | 11/2010 | Lebel et al. |
| 7,833,151 B2 | 11/2010 | Khait et al. |
| 7,833,170 B2 | 11/2010 | Matsumoto et al. |
| 7,837,633 B2 | 11/2010 | Conway et al. |
| 7,842,046 B1 | 11/2010 | Nakao |
| 7,846,132 B2 | 12/2010 | Gravesen et al. |
| 7,850,652 B2 | 12/2010 | Liniger et al. |
| 7,860,574 B2 | 12/2010 | Von Arx et al. |
| 7,866,026 B1 | 1/2011 | Wang et al. |
| 7,867,244 B2 | 1/2011 | Lathrop et al. |
| 7,873,299 B2 | 1/2011 | Berner et al. |
| 7,882,611 B2 | 2/2011 | Shah et al. |
| 7,883,464 B2 | 2/2011 | Stafford |
| 7,883,473 B2 | 2/2011 | LeVaughn et al. |
| 7,885,697 B2 | 2/2011 | Brister et al. |
| 7,889,069 B2 | 2/2011 | Fifolt et al. |
| 7,896,844 B2 | 3/2011 | Thalmann et al. |
| 7,899,511 B2 | 3/2011 | Shults et al. |
| 7,899,545 B2 | 3/2011 | John |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,914,460 B2 | 3/2011 | Melker et al. |
| 7,916,013 B2 | 3/2011 | Stevenson |
| 7,920,906 B2 | 4/2011 | Goode, Jr. et al. |
| 7,920,907 B2 | 4/2011 | McGarraugh et al. |
| 7,938,797 B2 | 5/2011 | Estes |
| 7,941,200 B2 | 5/2011 | Weinart et al. |
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,955,297 B2 | 6/2011 | Radmer et al. |
| 7,970,448 B2 | 6/2011 | Shults et al. |
| 7,970,449 B2 | 6/2011 | Ward |
| 7,972,296 B2 | 7/2011 | Braig et al. |
| 7,974,672 B2 | 7/2011 | Shults et al. |
| 7,976,467 B2 | 7/2011 | Young et al. |
| 7,978,063 B2 | 7/2011 | Baldus et al. |
| 7,985,203 B2 | 7/2011 | Haueter et al. |
| 7,985,222 B2 | 7/2011 | Gall et al. |
| 7,996,158 B2 | 8/2011 | Hayter et al. |
| 7,999,674 B2 | 8/2011 | Kamen |
| 8,000,918 B2 | 8/2011 | Fjield et al. |
| 8,005,524 B2 | 8/2011 | Brauker et al. |
| 8,010,174 B2 | 8/2011 | Goode, Jr. et al. |
| 8,010,256 B2 | 8/2011 | Oowada |
| 8,016,774 B2 | 9/2011 | Freeman et al. |
| 8,028,837 B2 | 10/2011 | Gerstle et al. |
| 8,029,441 B2 | 10/2011 | Mazza et al. |
| 8,029,442 B2 | 10/2011 | Funderburk et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,112,240 B2 | 2/2012 | Fennell |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Docks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,670 B2 | 4/2012 | Quyang et al. |
| 8,160,900 B2 | 4/2012 | Taub et al. |
| 8,172,805 B2 | 5/2012 | Mogensen et al. |
| 8,175,673 B2 | 5/2012 | Say et al. |
| 8,179,266 B2 | 5/2012 | Hermle |
| 8,180,423 B2 | 5/2012 | Mang et al. |
| 8,192,394 B2 | 6/2012 | Estes et al. |
| 8,216,138 B1 | 7/2012 | McGaraugh et al. |
| 8,221,332 B2 | 7/2012 | Robbins et al. |
| 8,224,410 B2 | 7/2012 | Hadvary et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,262,618 B2 | 9/2012 | Scheurer |
| 8,282,549 B2 | 10/2012 | Brauker et al. |
| 8,333,714 B2 | 12/2012 | Stafford |
| 8,346,335 B2 | 1/2013 | Harper et al. |
| 8,346,337 B2 | 1/2013 | Heller et al. |
| 8,373,544 B2 | 2/2013 | Pitt-Plady |
| 8,374,668 B1 | 2/2013 | Hayter et al. |
| 8,376,945 B2 | 2/2013 | Hayter et al. |
| 8,377,271 B2 | 2/2013 | Mao et al. |
| 8,382,671 B2 | 2/2013 | Anthony et al. |
| 8,398,664 B2 | 3/2013 | Lamps et al. |
| 8,409,093 B2 | 4/2013 | Bugler |
| 8,409,145 B2 | 4/2013 | Raymond et al. |
| 8,439,838 B2 | 5/2013 | Mogensen et al. |
| 8,444,560 B2 | 5/2013 | Hayter et al. |
| 8,461,985 B2 | 6/2013 | Fennell et al. |
| 8,469,986 B2 | 6/2013 | Schraga |
| 8,512,243 B2 | 8/2013 | Stafford |

(56)                References Cited

U.S. PATENT DOCUMENTS

| | | |
|---|---|---|
| 8,515,518 B2 | 8/2013 | Ouyang et al. |
| 8,515,519 B2 | 8/2013 | Brister et al. |
| 8,538,512 B1 | 9/2013 | Bibian et al. |
| 8,545,403 B2 | 10/2013 | Peyser et al. |
| 8,560,038 B2 | 10/2013 | Hayter et al. |
| 8,562,567 B2 | 10/2013 | Gundberg |
| 8,571,808 B2 | 10/2013 | Hayter |
| 8,583,205 B2 | 11/2013 | Budiman et al. |
| 8,585,591 B2 | 11/2013 | Sloan et al. |
| 8,597,570 B2 | 12/2013 | Terashima et al. |
| 8,600,681 B2 | 12/2013 | Hayter et al. |
| 8,602,991 B2 | 12/2013 | Stafford |
| 8,612,163 B2 | 12/2013 | Hayter et al. |
| 8,615,282 B2 | 12/2013 | Brister et al. |
| 8,617,069 B2 | 12/2013 | Bernstein et al. |
| 8,617,071 B2 | 12/2013 | Say et al. |
| 8,622,903 B2 | 1/2014 | Jin et al. |
| 8,628,498 B2 | 1/2014 | Safabach et al. |
| 8,641,674 B2 | 2/2014 | Bobroff et al. |
| 8,652,043 B2 | 2/2014 | Drucker et al. |
| 8,682,408 B2 | 3/2014 | Boock et al. |
| 8,682,615 B2 | 3/2014 | Hayter et al. |
| 8,684,930 B2 | 4/2014 | Feldman et al. |
| 8,692,655 B2 | 4/2014 | Zimman et al. |
| 8,710,993 B2 | 4/2014 | Hayter et al. |
| 8,747,363 B2 | 6/2014 | Nielsen et al. |
| 8,750,955 B2 | 6/2014 | Brister et al. |
| 8,771,183 B2 | 7/2014 | Sloan |
| 8,797,163 B2 | 8/2014 | Finkenzeller |
| 8,808,515 B2 | 8/2014 | Feldman et al. |
| 8,834,366 B2 | 9/2014 | Hayter et al. |
| 8,845,536 B2 | 9/2014 | Brauker et al. |
| 8,870,822 B2 | 10/2014 | Thalmann et al. |
| 8,880,138 B2 | 11/2014 | Cho |
| 8,945,056 B2 | 2/2015 | Iio et al. |
| 8,961,413 B2 | 2/2015 | Teller et al. |
| 9,007,781 B2 | 4/2015 | Moein et al. |
| 9,014,774 B2 | 4/2015 | Mao et al. |
| 9,031,630 B2 | 5/2015 | Hoss et al. |
| 9,060,719 B2 | 6/2015 | Hayter et al. |
| 9,060,805 B2 | 6/2015 | Goodnow et al. |
| 9,066,697 B2 | 6/2015 | Peyser et al. |
| 9,101,302 B2 | 8/2015 | Mace et al. |
| 9,186,098 B2 | 11/2015 | Lee et al. |
| 9,215,992 B2 | 12/2015 | Donnay et al. |
| 9,241,631 B2 | 1/2016 | Valdes et al. |
| 9,259,175 B2 | 2/2016 | Stafford |
| 9,265,453 B2 | 2/2016 | Curry et al. |
| 9,289,179 B2 | 3/2016 | Hayter et al. |
| 9,295,786 B2 | 3/2016 | Gottlieb et al. |
| 9,357,951 B2 | 6/2016 | Simpson et al. |
| 9,398,872 B2 | 7/2016 | Hayter et al. |
| 9,402,544 B2 | 8/2016 | Yee et al. |
| 9,402,570 B2 | 8/2016 | Pace et al. |
| 9,439,586 B2 | 9/2016 | Bugler |
| 9,451,910 B2 | 9/2016 | Brister et al. |
| 9,474,479 B2 | 10/2016 | Pusey et al. |
| 9,480,421 B2 | 11/2016 | Stafford |
| 9,483,608 B2 | 11/2016 | Hayter et al. |
| 9,504,471 B2 | 11/2016 | Vaitekunas et al. |
| 9,558,325 B2 | 1/2017 | Hayter et al. |
| 9,566,384 B2 | 2/2017 | Gyrn et al. |
| 9,636,068 B2 | 5/2017 | Yee et al. |
| 9,668,682 B2 | 6/2017 | Brister et al. |
| 9,743,876 B2 | 8/2017 | Gelfand et al. |
| 9,808,574 B2 | 11/2017 | Yodfat et al. |
| 9,814,414 B2 | 11/2017 | Brister et al. |
| 10,213,139 B2 | 2/2019 | Rao et al. |
| 10,292,632 B2 | 5/2019 | Lee et al. |
| 10,342,489 B2 | 7/2019 | Stafford |
| 10,772,547 B1 | 9/2020 | Lee et al. |
| 10,820,842 B2 | 11/2020 | Harper |
| 10,827,954 B2 | 11/2020 | Hoss et al. |
| 10,874,338 B2 | 12/2020 | Stafford |
| 10,881,340 B2 | 1/2021 | Curry et al. |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Simpson et al. |
| 11,000,213 B2 | 5/2021 | Kamath et al. |
| 11,000,216 B2 | 5/2021 | Curry et al. |
| 11,006,870 B2 | 5/2021 | Yee et al. |
| 11,006,871 B2 | 5/2021 | Yee et al. |
| 11,013,440 B2 | 5/2021 | Lee et al. |
| 11,051,724 B2 | 7/2021 | Pace et al. |
| 11,064,917 B2 | 7/2021 | Simpson et al. |
| 11,116,430 B2 | 9/2021 | Funderburk et al. |
| 11,141,084 B2 | 10/2021 | Funderburk et al. |
| 11,166,656 B2 | 11/2021 | Yee et al. |
| 11,179,068 B2 | 11/2021 | Pace et al. |
| 11,197,625 B1 | 12/2021 | Schleicher et al. |
| 11,202,591 B2 | 12/2021 | Yee et al. |
| 11,213,229 B2 | 1/2022 | Yee et al. |
| 11,246,519 B2 | 2/2022 | Donnay et al. |
| 11,266,335 B2 | 3/2022 | Donnay et al. |
| 11,298,056 B2 | 4/2022 | Harper |
| 11,298,058 B2 | 4/2022 | Stafford |
| 11,510,625 B2 | 11/2022 | Gray et al. |
| 2001/0016682 A1 | 8/2001 | Berner et al. |
| 2001/0034479 A1 | 10/2001 | Ring et al. |
| 2001/0037060 A1 | 11/2001 | Thompson et al. |
| 2001/0037366 A1 | 11/2001 | Webb et al. |
| 2001/0039387 A1 | 11/2001 | Rutynowski et al. |
| 2001/0044608 A1 | 11/2001 | Odell et al. |
| 2001/0047127 A1 | 11/2001 | New et al. |
| 2001/0056262 A1 | 12/2001 | Cabiri et al. |
| 2002/0002344 A1 | 1/2002 | Douglas et al. |
| 2002/0010390 A1 | 1/2002 | Guice et al. |
| 2002/0013522 A1 | 1/2002 | Lav et al. |
| 2002/0013538 A1 | 1/2002 | Teller |
| 2002/0016534 A1 | 2/2002 | Trepagnier et al. |
| 2002/0016568 A1 | 2/2002 | Lebel et al. |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0029058 A1 | 3/2002 | LeVaughn et al. |
| 2002/0032386 A1 | 3/2002 | Sackner et al. |
| 2002/0039026 A1 | 4/2002 | Stroth et al. |
| 2002/0042090 A1 | 4/2002 | Heller et al. |
| 2002/0045808 A1 | 4/2002 | Ford et al. |
| 2002/0049482 A1 | 4/2002 | Fabian et al. |
| 2002/0050250 A1 | 5/2002 | Peterson et al. |
| 2002/0055711 A1 | 5/2002 | Lavi et al. |
| 2002/0057993 A1 | 5/2002 | Maisey et al. |
| 2002/0065454 A1 | 5/2002 | Lebel et al. |
| 2002/0066764 A1 | 6/2002 | Perry et al. |
| 2002/0072720 A1 | 6/2002 | Hague et al. |
| 2002/0072784 A1 | 6/2002 | Sheppard et al. |
| 2002/0074162 A1 | 6/2002 | Su et al. |
| 2002/0076966 A1 | 6/2002 | Carron et al. |
| 2002/0077599 A1 | 6/2002 | Wojcik |
| 2002/0082487 A1 | 6/2002 | Kollias et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0117639 A1 | 8/2002 | Paolini et al. |
| 2002/0118528 A1 | 8/2002 | Su et al. |
| 2002/0119711 A1 | 8/2002 | VanAntwerp et al. |
| 2002/0120186 A1 | 8/2002 | Keimel |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133066 A1 | 9/2002 | Miller et al. |

(56)                References Cited

U.S. PATENT DOCUMENTS

| | | |
|---|---|---|
| 2002/0147135 A1 | 10/2002 | Schnell |
| 2002/0151770 A1 | 10/2002 | Noll et al. |
| 2002/0151796 A1 | 10/2002 | Koulik |
| 2002/0151816 A1 | 10/2002 | Rich et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0161338 A1 | 10/2002 | Peterson |
| 2002/0164836 A1 | 11/2002 | Ho |
| 2002/0165462 A1 | 11/2002 | Westbrook et al. |
| 2002/0169369 A1 | 11/2002 | Ward et al. |
| 2002/0169439 A1 | 11/2002 | Flaherty et al. |
| 2002/0169635 A1 | 11/2002 | Shillingburg |
| 2002/0183604 A1 | 12/2002 | Gowda et al. |
| 2002/0185128 A1 | 12/2002 | Theobald |
| 2002/0185130 A1 | 12/2002 | Wright et al. |
| 2002/0188748 A1 | 12/2002 | Blackwell et al. |
| 2002/0197522 A1 | 12/2002 | Lawrence et al. |
| 2002/0198444 A1 | 12/2002 | Ughigaki et al. |
| 2002/0198543 A1 | 12/2002 | Burdulis et al. |
| 2003/0004403 A1 | 1/2003 | Drinan et al. |
| 2003/0020477 A1 | 1/2003 | Goldstein |
| 2003/0023189 A1 | 1/2003 | Kuo |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028184 A1 | 2/2003 | Lebel et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0055380 A1 | 3/2003 | Flaherty |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0069509 A1 | 4/2003 | Matzinger et al. |
| 2003/0069510 A1 | 4/2003 | Semler |
| 2003/0076792 A1 | 4/2003 | Theimer |
| 2003/0077642 A1 | 4/2003 | Fritsch et al. |
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0088166 A1 | 5/2003 | Say et al. |
| 2003/0097092 A1 | 5/2003 | Flaherty |
| 2003/0100040 A1 | 5/2003 | Bonnecaze et al. |
| 2003/0100821 A1 | 5/2003 | Heller et al. |
| 2003/0109775 A1 | 6/2003 | O'Neil et al. |
| 2003/0114897 A1 | 6/2003 | Von Arx et al. |
| 2003/0114898 A1 | 6/2003 | Von Arx et al. |
| 2003/0119457 A1 | 6/2003 | Standke |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135127 A1 | 7/2003 | Sackner et al. |
| 2003/0135333 A1 | 7/2003 | Aceti et al. |
| 2003/0144579 A1 | 7/2003 | Buss |
| 2003/0144581 A1 | 7/2003 | Conn et al. |
| 2003/0144608 A1 | 7/2003 | Kojima et al. |
| 2003/0153900 A1 | 8/2003 | Aceti et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199790 A1 | 10/2003 | Boecker et al. |
| 2003/0199910 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216621 A1 | 11/2003 | Alpert et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2003/0225373 A1 | 12/2003 | Bobroff et al. |
| 2003/0236489 A1 | 12/2003 | Jacobson et al. |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0017300 A1 | 1/2004 | Kotzin et al. |
| 2004/0030226 A1 | 2/2004 | Quy |
| 2004/0030531 A1 | 2/2004 | Miller et al. |
| 2004/0030581 A1 | 2/2004 | Levin et al. |
| 2004/0034289 A1 | 2/2004 | Teller et al. |
| 2004/0039255 A1 | 2/2004 | Simonsen et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0061232 A1 | 4/2004 | Shah et al. |
| 2004/0063435 A1 | 4/2004 | Sakamoto et al. |
| 2004/0064068 A1 | 4/2004 | DeNuzzio et al. |
| 2004/0064133 A1 | 4/2004 | Miller et al. |
| 2004/0072357 A1 | 4/2004 | Steine et al. |
| 2004/0073266 A1 | 4/2004 | Haefner et al. |
| 2004/0078215 A1 | 4/2004 | Dahlin et al. |
| 2004/0096959 A1 | 5/2004 | Steine et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0111017 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0117204 A1 | 6/2004 | Mazar et al. |
| 2004/0119169 A1 | 6/2004 | Hanawa |
| 2004/0122353 A1 | 6/2004 | Shahmirian et al. |
| 2004/0122489 A1 | 6/2004 | Mazar et al. |
| 2004/0133089 A1 | 7/2004 | Kilcoyne et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0147996 A1 | 7/2004 | Miazga et al. |
| 2004/0152366 A1 | 8/2004 | Schultz et al. |
| 2004/0152622 A1 | 8/2004 | Keith et al. |
| 2004/0158207 A1 | 8/2004 | Hunn et al. |
| 2004/0162521 A1 | 8/2004 | Bengtsson et al. |
| 2004/0162678 A1 | 8/2004 | Hetzel et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204673 A1 | 10/2004 | Flaherty |
| 2004/0204687 A1 | 10/2004 | Mogensen et al. |
| 2004/0204744 A1 | 10/2004 | Penner et al. |
| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0210122 A1 | 10/2004 | Sieburg |

(56) References Cited

U.S. PATENT DOCUMENTS

| | | |
|---|---|---|
| 2004/0221057 A1 | 11/2004 | Darcey et al. |
| 2004/0223876 A1 | 11/2004 | Kirollos et al. |
| 2004/0223985 A1 | 11/2004 | Dunfield et al. |
| 2004/0225199 A1 | 11/2004 | Evanyk et al. |
| 2004/0225262 A1 | 11/2004 | Fathallah et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0240426 A1 | 12/2004 | Wu et al. |
| 2004/0249253 A1 | 12/2004 | Racchini et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0258564 A1 | 12/2004 | Charlton |
| 2004/0260224 A1 | 12/2004 | Binder et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038465 A1 | 2/2005 | Shraga |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0065464 A1 | 3/2005 | Talbot et al. |
| 2005/0070774 A1 | 3/2005 | Addison et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0096520 A1 | 5/2005 | Maekawa et al. |
| 2005/0096587 A1 | 5/2005 | Santini, Jr. et al. |
| 2005/0101912 A1 | 5/2005 | Faust et al. |
| 2005/0101932 A1 | 5/2005 | Cote et al. |
| 2005/0103624 A1 | 5/2005 | Bhullar et al. |
| 2005/0104457 A1 | 5/2005 | Jordan et al. |
| 2005/0106713 A1 | 5/2005 | Phan et al. |
| 2005/0112169 A1 | 5/2005 | Brauker et al. |
| 2005/0112544 A1 | 5/2005 | Xu et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0131347 A1 | 6/2005 | Marano-Ford et al. |
| 2005/0134731 A1 | 6/2005 | Lee et al. |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0149066 A1 | 7/2005 | Stafford |
| 2005/0151976 A1 | 7/2005 | Toma |
| 2005/0154271 A1 | 7/2005 | Rasdal et al. |
| 2005/0154410 A1 | 7/2005 | Conway et al. |
| 2005/0159678 A1 | 7/2005 | Taniike et al. |
| 2005/0161346 A1 | 7/2005 | Simpson et al. |
| 2005/0165404 A1 | 7/2005 | Miller |
| 2005/0171442 A1 | 8/2005 | Shirasaki et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Heit et al. |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0197793 A1 | 9/2005 | Baker |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0221504 A1 | 10/2005 | Petruno et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245844 A1 | 11/2005 | Mace et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0267325 A1 | 12/2005 | Bouchier et al. |
| 2005/0267327 A1 | 12/2005 | Iizuka et al. |
| 2005/0269214 A1 | 12/2005 | Lee |
| 2005/0277164 A1 | 12/2005 | Drucker et al. |
| 2005/0277912 A1 | 12/2005 | John |
| 2005/0281234 A1 | 12/2005 | Kawamura et al. |
| 2005/0283114 A1 | 12/2005 | Bresina et al. |
| 2005/0283208 A1 | 12/2005 | Von Arx et al. |
| 2005/0283209 A1 | 12/2005 | Katoozi et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0004272 A1 | 1/2006 | Shah et al. |
| 2006/0004303 A1 | 1/2006 | Weidenhaupt et al. |
| 2006/0006141 A1 | 1/2006 | Ufer et al. |
| 2006/0009727 A1 | 1/2006 | O'Mahony et al. |
| 2006/0010098 A1 | 1/2006 | Goodnow et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0030789 A1 | 2/2006 | Allen |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |

(56) References Cited

U.S. PATENT DOCUMENTS

| | | |
|---|---|---|
| 2006/0036145 A1 | 2/2006 | Brister et al. |
| 2006/0040402 A1 | 2/2006 | Brauker et al. |
| 2006/0040793 A1 | 2/2006 | Martens et al. |
| 2006/0041276 A1 | 2/2006 | Chan |
| 2006/0042080 A1 | 3/2006 | Say et al. |
| 2006/0047220 A1 | 3/2006 | Sakata et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0068208 A1 | 3/2006 | Tapsak et al. |
| 2006/0079740 A1 | 4/2006 | Silver et al. |
| 2006/0081469 A1 | 4/2006 | Lee |
| 2006/0086624 A1 | 4/2006 | Tapsak et al. |
| 2006/0091006 A1 | 5/2006 | Wang et al. |
| 2006/0094944 A1 | 5/2006 | Chuang |
| 2006/0095014 A1 | 5/2006 | Ethelfeld |
| 2006/0116607 A1 | 6/2006 | Nakamura et al. |
| 2006/0129173 A1 | 6/2006 | Wilkinson |
| 2006/0129733 A1 | 6/2006 | Solbelman |
| 2006/0135908 A1 | 6/2006 | Liniger et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0155210 A1 | 7/2006 | Beckman et al. |
| 2006/0155317 A1 | 7/2006 | List |
| 2006/0161194 A1 | 7/2006 | Freeman et al. |
| 2006/0161664 A1 | 7/2006 | Motoyama |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0181695 A1 | 8/2006 | Sage, Jr. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0189939 A1 | 8/2006 | Gonnelli et al. |
| 2006/0193375 A1 | 8/2006 | Lee et al. |
| 2006/0195029 A1 | 8/2006 | Shults et al. |
| 2006/0195133 A1 | 8/2006 | Freeman et al. |
| 2006/0200020 A1 | 9/2006 | Brister et al. |
| 2006/0200022 A1 | 9/2006 | Brauker et al. |
| 2006/0200181 A1 | 9/2006 | Fukuzawa et al. |
| 2006/0200970 A1 | 9/2006 | Brister et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0211921 A1 | 9/2006 | Brauker et al. |
| 2006/0220839 A1 | 10/2006 | Fifolt et al. |
| 2006/0222566 A1 | 10/2006 | Brauker et al. |
| 2006/0222866 A1 | 10/2006 | Nakamura et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0224171 A1 | 10/2006 | Sakata et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0247895 A1 | 11/2006 | Liamos et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0258929 A1 | 11/2006 | Goode, Jr. et al. |
| 2006/0258939 A1 | 11/2006 | Pesach et al. |
| 2006/0258959 A1 | 11/2006 | Sode |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0270923 A1 | 11/2006 | Brauker et al. |
| 2006/0271013 A1 | 11/2006 | Triplett et al. |
| 2006/0272652 A1 | 12/2006 | Stocker et al. |
| 2006/0273759 A1 | 12/2006 | Reggiardo |
| 2006/0276714 A1 | 12/2006 | Holt et al. |
| 2006/0276724 A1 | 12/2006 | Freeman et al. |
| 2006/0276771 A1 | 12/2006 | Galley et al. |
| 2006/0281985 A1 | 12/2006 | Ward et al. |
| 2006/0282042 A1 | 12/2006 | Walters et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016129 A1 | 1/2007 | Liniger et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0027507 A1 | 2/2007 | Burdett et al. |
| 2007/0030154 A1 | 2/2007 | Aiki et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0033074 A1 | 2/2007 | Nitzan et al. |
| 2007/0038044 A1 | 2/2007 | Dobbles et al. |
| 2007/0045902 A1 | 3/2007 | Brauker et al. |
| 2007/0049865 A1 | 3/2007 | Radmer et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060801 A1 | 3/2007 | Neinast |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0088377 A1 | 4/2007 | Levaughn et al. |
| 2007/0090511 A1 | 4/2007 | Borland et al. |
| 2007/0093704 A1 | 4/2007 | Brister et al. |
| 2007/0093754 A1 | 4/2007 | Mogensen et al. |
| 2007/0093786 A1 | 4/2007 | Goldsmith et al. |
| 2007/0095661 A1 | 5/2007 | Wang et al. |
| 2007/0100218 A1 | 5/2007 | Sweitzer et al. |
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0108048 A1 | 5/2007 | Wang et al. |
| 2007/0110124 A1 | 5/2007 | Shiraki et al. |
| 2007/0111196 A1 | 5/2007 | Alarcon et al. |
| 2007/0123819 A1 | 5/2007 | Mernoe et al. |
| 2007/0124002 A1 | 5/2007 | Estes et al. |
| 2007/0129621 A1 | 6/2007 | Kellogg et al. |
| 2007/0135696 A1 | 6/2007 | Ward |
| 2007/0135774 A1 | 6/2007 | Turner et al. |
| 2007/0149873 A1 | 6/2007 | Say et al. |
| 2007/0149875 A1 | 6/2007 | Ouyang et al. |
| 2007/0150959 A1 | 6/2007 | Ahdout et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173741 A1 | 7/2007 | Deshmukh et al. |
| 2007/0173761 A1 | 7/2007 | Kanderian, Jr. et al. |
| 2007/0179349 A1 | 8/2007 | Hoyme et al. |
| 2007/0179352 A1 | 8/2007 | Randlov et al. |
| 2007/0179406 A1 | 8/2007 | DeNuzzio et al. |
| 2007/0191701 A1 | 8/2007 | Feldman et al. |
| 2007/0191702 A1 | 8/2007 | Yodfat et al. |
| 2007/0197889 A1 | 8/2007 | Brister et al. |
| 2007/0199818 A1 | 8/2007 | Petyt et al. |
| 2007/0202562 A1 | 8/2007 | Curry et al. |

(56)                References Cited

U.S. PATENT DOCUMENTS

| | | |
|---|---|---|
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213611 A1 | 9/2007 | Simpson et al. |
| 2007/0219480 A1 | 9/2007 | Kamen et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232877 A1 | 10/2007 | He |
| 2007/0232878 A1 | 10/2007 | Kovatchev et al. |
| 2007/0232879 A1 | 10/2007 | Brister et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244383 A1 | 10/2007 | Talbot et al. |
| 2007/0244398 A1 | 10/2007 | Lo et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255125 A1 | 11/2007 | Moberg et al. |
| 2007/0255302 A1 | 11/2007 | Koeppel et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2008/0004512 A1 | 1/2008 | Funderburk et al. |
| 2008/0004515 A1 | 1/2008 | Jennewine et al. |
| 2008/0004573 A1 | 1/2008 | Kaufmann et al. |
| 2008/0004601 A1 | 1/2008 | Jennewine et al. |
| 2008/0004904 A1 | 1/2008 | Tran |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021543 A1 | 1/2008 | Shrivastava |
| 2008/0021666 A1 | 1/2008 | Goode, Jr. et al. |
| 2008/0027296 A1 | 1/2008 | Hadvary et al. |
| 2008/0027474 A1 | 1/2008 | Curry et al. |
| 2008/0029391 A1 | 2/2008 | Mao et al. |
| 2008/0030369 A1 | 2/2008 | Mann et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033273 A1 | 2/2008 | Zhou et al. |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0046038 A1 | 2/2008 | Hill et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0058830 A1 | 3/2008 | Cole et al. |
| 2008/0059227 A1 | 3/2008 | Clapp |
| 2008/0060955 A1 | 3/2008 | Goodnow |
| 2008/0061961 A1 | 3/2008 | John |
| 2008/0062055 A1 | 3/2008 | Cunningham et al. |
| 2008/0064437 A1 | 3/2008 | Chambers et al. |
| 2008/0064937 A1 | 3/2008 | McGarraugh et al. |
| 2008/0064941 A1 | 3/2008 | Funderburk et al. |
| 2008/0064943 A1 | 3/2008 | Talbot et al. |
| 2008/0064944 A1 | 3/2008 | VanAntwerp et al. |
| 2008/0065646 A1 | 3/2008 | Zhang et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0092911 A1 | 4/2008 | Schulman et al. |
| 2008/0097246 A1 | 4/2008 | Stafford |
| 2008/0097289 A1 | 4/2008 | Steil et al. |
| 2008/0097908 A1 | 4/2008 | Dicks et al. |
| 2008/0099332 A1 | 5/2008 | Scott et al. |
| 2008/0102441 A1 | 5/2008 | Chen et al. |
| 2008/0108942 A1 | 5/2008 | Brister et al. |
| 2008/0112848 A1 | 5/2008 | Huffstodt et al. |
| 2008/0114228 A1 | 5/2008 | McCluskey et al. |
| 2008/0114280 A1 | 5/2008 | Stafford |
| 2008/0119705 A1 | 5/2008 | Patel et al. |
| 2008/0119707 A1 | 5/2008 | Stafford |
| 2008/0119710 A1 | 5/2008 | Reggiardo et al. |
| 2008/0125636 A1 | 5/2008 | Ward et al. |
| 2008/0127052 A1 | 5/2008 | Rostoker |
| 2008/0129486 A1 | 6/2008 | Jeckelmann et al. |
| 2008/0133059 A1 | 6/2008 | Trippel et al. |
| 2008/0133702 A1 | 6/2008 | Sharma et al. |
| 2008/0139910 A1 | 6/2008 | Mastrototaro et al. |
| 2008/0146904 A1 | 6/2008 | Hunn |
| 2008/0148873 A1 | 6/2008 | Wang |
| 2008/0154205 A1 | 6/2008 | Wojcik |
| 2008/0154286 A1 | 6/2008 | Abbott et al. |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0167578 A1 | 7/2008 | Bryer et al. |
| 2008/0172205 A1 | 7/2008 | Breton et al. |
| 2008/0177149 A1 | 7/2008 | Weinart et al. |
| 2008/0177165 A1 | 7/2008 | Blomquist et al. |
| 2008/0179187 A1 | 7/2008 | Ouyang |
| 2008/0182537 A1 | 7/2008 | Manku et al. |
| 2008/0183060 A1 | 7/2008 | Steil et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0188796 A1 | 8/2008 | Steil et al. |
| 2008/0189051 A1 | 8/2008 | Goode, Jr. et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214481 A1 | 9/2008 | Challoner et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0215035 A1 | 9/2008 | Yodfat et al. |
| 2008/0228051 A1 | 9/2008 | Shults et al. |

(56) References Cited

U.S. PATENT DOCUMENTS

| | | |
|---|---|---|
| 2008/0228054 A1 | 9/2008 | Shults et al. |
| 2008/0234561 A1 | 9/2008 | Roesicke et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0242963 A1 | 10/2008 | Essenpreis et al. |
| 2008/0243051 A1 | 10/2008 | DeStefano |
| 2008/0252459 A1 | 10/2008 | Butler et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255440 A1 | 10/2008 | Eilerson et al. |
| 2008/0255808 A1 | 10/2008 | Hayter |
| 2008/0256048 A1 | 10/2008 | Hayter |
| 2008/0262300 A1 | 10/2008 | Reynolds et al. |
| 2008/0262469 A1 | 10/2008 | Brister et al. |
| 2008/0267823 A1 | 10/2008 | Wang et al. |
| 2008/0269584 A1 | 10/2008 | Shekalim |
| 2008/0269673 A1 | 10/2008 | Butoi et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0281178 A1 | 11/2008 | Chuang et al. |
| 2008/0281179 A1 | 11/2008 | Fennell et al. |
| 2008/0283396 A1 | 11/2008 | Wang et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0308523 A1 | 12/2008 | Krulevitch et al. |
| 2008/0312518 A1 | 12/2008 | Jina et al. |
| 2008/0312601 A1 | 12/2008 | Cane |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319085 A1 | 12/2008 | Wright et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2008/0319416 A1 | 12/2008 | Yodfat et al. |
| 2009/0005659 A1 | 1/2009 | Kollias et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinart et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0028824 A1 | 1/2009 | Chiang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0036915 A1 | 2/2009 | Karbowniczek et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048499 A1 | 2/2009 | Glejbol |
| 2009/0048503 A1 | 2/2009 | Dalal et al. |
| 2009/0048563 A1 | 2/2009 | Ethelfeld et al. |
| 2009/0054737 A1 | 2/2009 | Magar et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0054866 A1 | 2/2009 | Teisen-Simony et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063187 A1 | 3/2009 | Johnson et al. |
| 2009/0063402 A1 | 3/2009 | Hayter |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0099521 A1 | 4/2009 | Gravesen et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105569 A1 | 4/2009 | Stafford |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0108992 A1 | 4/2009 | Shafer |
| 2009/0112123 A1 | 4/2009 | Freeman et al. |
| 2009/0112478 A1 | 4/2009 | Mueller, Jr. et al. |
| 2009/0118592 A1 | 5/2009 | Klitgaard |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0150454 A1 | 6/2009 | Gejdos et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |

(56)　　References Cited

U.S. PATENT DOCUMENTS

| | | |
|---|---|---|
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0198186 A1 | 8/2009 | Mernoe et al. |
| 2009/0198215 A1 | 8/2009 | Chong et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch-Menges et al. |
| 2009/0212766 A1 | 8/2009 | Olson et al. |
| 2009/0216100 A1 | 8/2009 | Ebner et al. |
| 2009/0216103 A1 | 8/2009 | Brister et al. |
| 2009/0216215 A1 | 8/2009 | Thalmann et al. |
| 2009/0234200 A1 | 9/2009 | Husheer |
| 2009/0240120 A1 | 9/2009 | Mensinger et al. |
| 2009/0240121 A1 | 9/2009 | Bickoff |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorenson |
| 2009/0253973 A1 | 10/2009 | Bashan et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0267765 A1 | 10/2009 | Greene et al. |
| 2009/0270765 A1 | 10/2009 | Ghesquire et al. |
| 2009/0277242 A1 | 11/2009 | Crane et al. |
| 2009/0281406 A1 | 11/2009 | McGarraugh et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292184 A1 | 11/2009 | Funderburk et al. |
| 2009/0292185 A1 | 11/2009 | Funderburk et al. |
| 2009/0294277 A1 | 12/2009 | Thomas et al. |
| 2009/0298182 A1 | 12/2009 | Schulat et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2009/0299301 A1 | 12/2009 | Gottleib et al. |
| 2010/0004597 A1 | 1/2010 | Gryn et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0022988 A1 | 1/2010 | Wochner et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030111 A1 | 2/2010 | Perriere |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0049129 A1 | 2/2010 | Yokoi et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0076379 A1 | 3/2010 | Matusch |
| 2010/0081905 A1 | 4/2010 | Bommakanti et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0105999 A1 | 4/2010 | Dixon et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak et al. |
| 2010/0119881 A1 | 5/2010 | Patel et al. |
| 2010/0121167 A1 | 5/2010 | McGarraugh et al. |
| 2010/0121169 A1 | 5/2010 | Petisce et al. |
| 2010/0137695 A1 | 6/2010 | Yodfat et al. |
| 2010/0141656 A1 | 6/2010 | Krieftewirth |
| 2010/0145229 A1 | 6/2010 | Perez et al. |
| 2010/0145377 A1 | 6/2010 | Lai et al. |
| 2010/0146300 A1 | 6/2010 | Brown |
| 2010/0152548 A1 | 6/2010 | Koski |
| 2010/0152554 A1 | 6/2010 | Steine et al. |
| 2010/0152674 A1 | 6/2010 | Kavazov et al. |
| 2010/0160757 A1 | 6/2010 | Weinart et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168547 A1 | 7/2010 | Kamath et al. |
| 2010/0168660 A1 | 7/2010 | Galley et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0174266 A1 | 7/2010 | Estes |
| 2010/0179399 A1 | 7/2010 | Goode, Jr. et al. |
| 2010/0179400 A1 | 7/2010 | Brauker et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179405 A1 | 7/2010 | Goode, Jr. et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |

(56)                References Cited

U.S. PATENT DOCUMENTS

| | | |
|---|---|---|
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191087 A1 | 7/2010 | Talbot et al. |
| 2010/0191472 A1 | 7/2010 | Doniger et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198042 A1 | 8/2010 | Sloan et al. |
| 2010/0198142 A1 | 8/2010 | Sloan et al. |
| 2010/0198314 A1 | 8/2010 | Wei |
| 2010/0204557 A1 | 8/2010 | Kiaie et al. |
| 2010/0204653 A1 | 8/2010 | Gryn et al. |
| 2010/0212583 A1 | 8/2010 | Brister et al. |
| 2010/0213057 A1 | 8/2010 | Feldman et al. |
| 2010/0213080 A1 | 8/2010 | Celentano et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228111 A1 | 9/2010 | Friman et al. |
| 2010/0228497 A1 | 9/2010 | Kamath et al. |
| 2010/0230285 A1 | 9/2010 | Hoss et al. |
| 2010/0235439 A1 | 9/2010 | Goodnow et al. |
| 2010/0240975 A1 | 9/2010 | Goode, Jr. et al. |
| 2010/0240976 A1 | 9/2010 | Goode, Jr. et al. |
| 2010/0256471 A1 | 10/2010 | Say et al. |
| 2010/0259543 A1 | 10/2010 | Tarassenko et al. |
| 2010/0261987 A1 | 10/2010 | Kamath et al. |
| 2010/0262183 A1 | 10/2010 | Abbott et al. |
| 2010/0262201 A1 | 10/2010 | He et al. |
| 2010/0267161 A1 | 10/2010 | Wu et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0325868 A1 | 12/2010 | Wang et al. |
| 2010/0326842 A1 | 12/2010 | Mazza et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331651 A1 | 12/2010 | Groll |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0004276 A1 | 1/2011 | Blair et al. |
| 2011/0009727 A1 | 1/2011 | Mensinger et al. |
| 2011/0015509 A1 | 1/2011 | Peyser |
| 2011/0016691 A1 | 1/2011 | Alden et al. |
| 2011/0021889 A1 | 1/2011 | Hoss et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0046977 A1 | 2/2011 | Goodnow et al. |
| 2011/0054275 A1 | 3/2011 | Stafford |
| 2011/0054282 A1 | 3/2011 | Nekoomaram et al. |
| 2011/0060196 A1 | 3/2011 | Stafford |
| 2011/0060530 A1 | 3/2011 | Fennell |
| 2011/0070633 A1 | 3/2011 | Matsumoto et al. |
| 2011/0073475 A1 | 3/2011 | Kastanos et al. |
| 2011/0077469 A1 | 3/2011 | Blocker et al. |
| 2011/0077490 A1 | 3/2011 | Simpson et al. |
| 2011/0077494 A1 | 3/2011 | Doniger et al. |
| 2011/0077659 A1 | 3/2011 | Mandecki et al. |
| 2011/0081726 A1 | 4/2011 | Berman et al. |
| 2011/0082484 A1 | 4/2011 | Saravia et al. |
| 2011/0087196 A1 | 4/2011 | Hunn et al. |
| 2011/0097090 A1 | 4/2011 | Cao |
| 2011/0106126 A1 | 5/2011 | Love et al. |
| 2011/0112696 A1 | 5/2011 | Yodfat et al. |
| 2011/0118579 A1 | 5/2011 | Goode, Jr. et al. |
| 2011/0118580 A1 | 5/2011 | Goode, Jr. et al. |
| 2011/0123971 A1 | 5/2011 | Berkowitz et al. |
| 2011/0124992 A1 | 5/2011 | Brauker et al. |
| 2011/0124997 A1 | 5/2011 | Goode, Jr. et al. |
| 2011/0125040 A1 | 5/2011 | Crawford et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137257 A1 | 6/2011 | Gyrn et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0152637 A1 | 6/2011 | Kateraas et al. |
| 2011/0172510 A1 | 7/2011 | Chickering, III et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0184482 A1 | 7/2011 | Eberman et al. |
| 2011/0184752 A1 | 7/2011 | Ray et al. |
| 2011/0190603 A1 | 8/2011 | Stafford |
| 2011/0190614 A1 | 8/2011 | Brister et al. |
| 2011/0191044 A1 | 8/2011 | Stafford |
| 2011/0193704 A1 | 8/2011 | Harper et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0213225 A1 | 9/2011 | Bernstein et al. |
| 2011/0218414 A1 | 9/2011 | Kamath et al. |
| 2011/0218490 A1 | 9/2011 | Ocvirk et al. |
| 2011/0230741 A1 | 9/2011 | Liang et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257495 A1 | 10/2011 | Hoss et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0288574 A1 | 11/2011 | Curry et al. |
| 2011/0289497 A1 | 11/2011 | Kiaie et al. |
| 2011/0290645 A1 | 12/2011 | Brister et al. |

(56)                References Cited

U.S. PATENT DOCUMENTS

| | | |
|---|---|---|
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0088995 A1 | 4/2012 | Fennell et al. |
| 2012/0095406 A1 | 4/2012 | Gyrn et al. |
| 2012/0108934 A1 | 5/2012 | Valdes et al. |
| 2012/0108983 A1 | 5/2012 | Banet et al. |
| 2012/0116322 A1 | 5/2012 | Brink et al. |
| 2012/0123385 A1 | 5/2012 | Edwards et al. |
| 2012/0143135 A1 | 6/2012 | Cole et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179113 A1 | 7/2012 | Yokota et al. |
| 2012/0184909 A1 | 7/2012 | Gyrn et al. |
| 2012/0190989 A1 | 7/2012 | Kaiser et al. |
| 2012/0197098 A1 | 8/2012 | Donnay et al. |
| 2012/0197222 A1 | 8/2012 | Donnay et al. |
| 2012/0245447 A1 | 9/2012 | Karan et al. |
| 2012/0265042 A1 | 10/2012 | Neinast et al. |
| 2012/0296327 A1 | 11/2012 | Hutchins et al. |
| 2012/0303043 A1 | 11/2012 | Donnay et al. |
| 2013/0035575 A1 | 2/2013 | Mayou et al. |
| 2013/0047981 A1 | 2/2013 | Bacon |
| 2013/0109940 A1 | 5/2013 | Yang et al. |
| 2013/0111248 A1 | 5/2013 | Ghesquiere et al. |
| 2013/0150691 A1 | 6/2013 | Pace et al. |
| 2013/0184547 A1 | 7/2013 | Taub et al. |
| 2013/0199312 A1 | 8/2013 | Wilmer et al. |
| 2013/0225959 A1 | 8/2013 | Bugler |
| 2013/0235166 A1 | 9/2013 | Jones et al. |
| 2013/0253289 A1 | 9/2013 | Hadvary et al. |
| 2013/0267811 A1 | 10/2013 | Pryor et al. |
| 2013/0317323 A1 | 11/2013 | Fujiwara et al. |
| 2014/0031655 A1 | 1/2014 | Stafford |
| 2014/0121480 A1 | 5/2014 | Budiman et al. |
| 2014/0148667 A1 | 5/2014 | Boock et al. |
| 2014/0171771 A1 | 6/2014 | Feldman et al. |
| 2014/0188053 A1 | 7/2014 | Lundquist |
| 2014/0228760 A1 | 8/2014 | Ethelfeld |
| 2014/0275907 A1 | 9/2014 | Feldman et al. |
| 2015/0005601 A1 | 1/2015 | Hoss et al. |
| 2015/0018643 A1 | 1/2015 | Cole et al. |
| 2015/0025338 A1 | 1/2015 | Lee et al. |
| 2015/0073238 A1 | 3/2015 | Matsumoto et al. |
| 2015/0105644 A1 | 4/2015 | Yang et al. |
| 2015/0141776 A1 | 5/2015 | Hadvary et al. |
| 2015/0164545 A1 | 6/2015 | Gyrn |
| 2015/0173661 A1 | 6/2015 | Myles |
| 2015/0241407 A1 | 8/2015 | Ou et al. |
| 2015/0326072 A1 | 11/2015 | Petras et al. |
| 2016/0058342 A1 | 3/2016 | Maiz-Aguinaga et al. |
| 2016/0058470 A1 | 3/2016 | Peterson et al. |
| 2016/0058474 A1 | 3/2016 | Peterson et al. |
| 2016/0128615 A1 | 5/2016 | Curry et al. |
| 2016/0157759 A1 | 6/2016 | Yang |
| 2016/0256106 A1 | 9/2016 | Krasnow et al. |
| 2016/0331283 A1 | 11/2016 | Rao et al. |
| 2016/0331284 A1* | 11/2016 | Pace .................. A61B 5/14503 |
| 2016/0338733 A1 | 11/2016 | Shah et al. |
| 2016/0338734 A1 | 11/2016 | Shah et al. |
| 2016/0354555 A1 | 12/2016 | Gibson et al. |
| 2017/0112531 A1 | 4/2017 | Schoonmaker et al. |
| 2017/0112533 A1 | 4/2017 | Schoonmaker et al. |
| 2017/0112534 A1 | 4/2017 | Schoonmaker et al. |
| 2017/0127985 A1 | 5/2017 | Thompson et al. |
| 2017/0128011 A1 | 5/2017 | Frey et al. |
| 2017/0165451 A1 | 6/2017 | Frey et al. |
| 2017/0188908 A1 | 7/2017 | Hoss et al. |
| 2017/0188910 A1 | 7/2017 | Halac et al. |
| 2017/0188912 A1 | 7/2017 | Halac et al. |
| 2017/0216536 A1 | 8/2017 | Scott |
| 2017/0265791 A1 | 9/2017 | Pace et al. |
| 2017/0290534 A1 | 10/2017 | Antonio et al. |
| 2017/0290535 A1 | 10/2017 | Rao et al. |
| 2017/0290546 A1 | 10/2017 | Antonio et al. |
| 2017/0319137 A1 | 11/2017 | Tsubouchi et al. |
| 2017/0367630 A1 | 12/2017 | Arita et al. |
| 2017/0368268 A1 | 12/2017 | Chopra |
| 2018/0116572 A1 | 5/2018 | Simpson et al. |
| 2018/0125464 A1 | 5/2018 | Kolb et al. |
| 2018/0235520 A1 | 8/2018 | Rao et al. |
| 2018/0360493 A1 | 12/2018 | Baker et al. |
| 2018/0368771 A1 | 12/2018 | Gray et al. |
| 2019/0133501 A1 | 5/2019 | Rao et al. |
| 2019/0133638 A1 | 5/2019 | Ii et al. |
| 2019/0298240 A1 | 10/2019 | Lee et al. |
| 2020/0077928 A1 | 3/2020 | Brister et al. |
| 2020/0100712 A1 | 4/2020 | Stafford |
| 2020/0113494 A1 | 4/2020 | Akiyama |
| 2020/0178899 A1 | 6/2020 | Chae et al. |
| 2020/0196919 A1 | 6/2020 | Rao et al. |
| 2020/0397356 A1 | 12/2020 | Yee et al. |
| 2021/0030969 A1 | 2/2021 | Huang et al. |
| 2021/0113124 A1 | 4/2021 | Yee et al. |
| 2021/0161437 A1 | 6/2021 | Thomas et al. |
| 2021/0177315 A1 | 6/2021 | Thomas et al. |
| 2021/0204841 A1 | 7/2021 | Thomas et al. |
| 2021/0204843 A1 | 7/2021 | Mazza et al. |
| 2021/0378592 A1 | 12/2021 | Rodriguez et al. |
| 2022/0007973 A1 | 1/2022 | Rao et al. |
| 2022/0079475 A1 | 3/2022 | Cole et al. |
| 2022/0125480 A1 | 4/2022 | Rao et al. |
| 2023/0108476 A1 | 4/2023 | Rao |
| 2024/0293615 A1 | 9/2024 | Lanigan |

FOREIGN PATENT DOCUMENTS

| | | |
|---|---|---|
| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2766693 A1 | 9/2011 |
| CA | 2617965 | 10/2011 |
| CA | 2766685 A1 | 12/2011 |
| CA | 3050721 | 7/2018 |
| CN | 1202872 | 5/2005 |
| CN | 101163440 | 4/2008 |
| CN | 101268932 | 9/2008 |
| CN | 101296650 | 10/2008 |
| CN | 201370857 | 12/2009 |
| DE | 44 01 400 | 7/1995 |
| DE | 201 10 059 | 8/2002 |
| DE | 101 17 285 | 11/2002 |
| DE | 10 2008 053 216 | 5/2010 |
| EP | 0 010 375 | 4/1980 |
| EP | 0 026 995 | 4/1981 |
| EP | 0 048 090 | 3/1982 |
| EP | 0 078 636 | 5/1983 |
| EP | 0 096 288 | 12/1983 |
| EP | 0 098 592 | 1/1984 |
| EP | 0 125 139 | 11/1984 |
| EP | 0 127 958 | 12/1984 |
| EP | 0 136 362 | 4/1985 |
| EP | 0 170 375 | 2/1986 |
| EP | 0 177 743 | 4/1986 |
| EP | 0 080 304 | 5/1986 |

(56)
References Cited

FOREIGN PATENT DOCUMENTS

| | | |
|---|---|---|
| EP | 0 184 909 | 6/1986 |
| EP | 0 206 218 | 12/1986 |
| EP | 0 230 472 | 8/1987 |
| EP | 0 241 309 | 10/1987 |
| EP | 0 245 073 | 11/1987 |
| EP | 0 255 291 | 2/1988 |
| EP | 0 278 647 | 8/1988 |
| EP | 0 319 277 A1 | 6/1989 |
| EP | 0 320 109 | 6/1989 |
| EP | 0 353 328 | 2/1990 |
| EP | 0 359 831 | 3/1990 |
| EP | 0 368 209 | 5/1990 |
| EP | 0 390 390 | 10/1990 |
| EP | 0 396 788 | 11/1990 |
| EP | 0 400 918 | 12/1990 |
| EP | 0 453 283 | 10/1991 |
| EP | 0 470 290 | 2/1992 |
| EP | 0 567 725 | 11/1993 |
| EP | 0 286 118 | 1/1995 |
| EP | 0 680 727 | 11/1995 |
| EP | 0 724 859 | 8/1996 |
| EP | 0 805 574 | 11/1997 |
| EP | 1 897 488 | 12/1999 |
| EP | 0 973 289 | 1/2000 |
| EP | 0 678 308 | 5/2000 |
| EP | 1 048 264 | 11/2000 |
| EP | 1 177 802 | 2/2002 |
| EP | 0 729 366 | 7/2002 |
| EP | 1 292 218 | 3/2003 |
| EP | 1 077 634 | 7/2003 |
| EP | 1 092 390 | 7/2004 |
| EP | 1 568 309 | 8/2005 |
| EP | 1 630 898 | 3/2006 |
| EP | 1 666 091 | 6/2006 |
| EP | 1 669 020 | 6/2006 |
| EP | 1 703 697 | 9/2006 |
| EP | 1 704 889 | 9/2006 |
| EP | 1 704 893 | 9/2006 |
| EP | 1 729 128 | 12/2006 |
| EP | 0 987 982 | 1/2007 |
| EP | 1 956 371 | 8/2008 |
| EP | 1 972 270 A1 | 9/2008 |
| EP | 2 031 534 | 3/2009 |
| EP | 2 060 284 | 5/2009 |
| EP | 1 897 487 | 11/2009 |
| EP | 1 897 492 | 11/2009 |
| EP | 2 113 864 | 11/2009 |
| EP | 1 681 992 | 4/2010 |
| EP | 2 201 969 | 6/2010 |
| EP | 1 448 489 | 8/2010 |
| EP | 1 971 396 | 8/2010 |
| EP | 1 725 163 | 12/2010 |
| EP | 2 260 757 | 12/2010 |
| EP | 1 413 245 | 6/2011 |
| EP | 2 327 362 | 6/2011 |
| EP | 2 327 984 | 6/2011 |
| EP | 2 335 587 | 6/2011 |
| EP | 2 153 382 | 2/2012 |
| EP | 2 284 773 | 2/2012 |
| EP | 1 789 116 B1 | 5/2013 |
| EP | 3 251 597 B1 | 11/2019 |
| EP | 3 632 314 | 4/2020 |
| EP | 3 632 315 A1 | 4/2020 |
| EP | 3 851 045 A1 | 7/2021 |
| EP | 3 730 044 B1 | 12/2021 |
| EP | 3 730 045 B1 | 3/2022 |
| EP | 3 766 408 B1 | 4/2022 |
| EP | 3 928 688 B1 | 6/2022 |
| EP | 4 111 949 B1 | 7/2023 |
| EP | 4 344 633 | 4/2024 |
| EP | 4 203 819 B1 | 7/2024 |
| GB | 1 394 171 | 5/1975 |
| GB | 1 599 241 | 9/1981 |
| GB | 2 073 891 | 10/1981 |
| GB | 2 067 764 | 1/1984 |
| GB | 2 154 003 | 8/1985 |
| GB | 2 204 408 | 11/1988 |
| GB | 2 254 436 | 10/1992 |
| GB | 2 409 951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 01-114746 | 5/1989 |
| JP | 01-114747 | 5/1989 |
| JP | 01-124060 | 5/1989 |
| JP | 01-134244 | 5/1989 |
| JP | 01-156658 | 6/1989 |
| JP | 02-062958 | 3/1990 |
| JP | 02-120655 | 5/1990 |
| JP | 02-287145 | 11/1990 |
| JP | 02-310457 | 12/1990 |
| JP | 03-020752 | 1/1991 |
| JP | 03-026956 | 2/1991 |
| JP | 03-028752 | 2/1991 |
| JP | 03-500940 | 2/1991 |
| JP | 03-194458 | 8/1991 |
| JP | 03-202764 | 9/1991 |
| JP | 05-072171 | 3/1993 |
| JP | 05-196595 | 8/1993 |
| JP | 06-190050 | 7/1994 |
| JP | 07-055757 | 3/1995 |
| JP | 07-072585 | 3/1995 |
| JP | 07-182462 | 7/1995 |
| JP | 07-311196 | 11/1995 |
| JP | 08-285814 | 11/1996 |
| JP | 08-285815 | 11/1996 |
| JP | 09-021778 | 1/1997 |
| JP | 09-101280 | 4/1997 |
| JP | 09-285459 | 4/1997 |
| JP | 10-170471 | 6/1998 |
| JP | 10-305016 | 11/1998 |
| JP | 11-506629 | 6/1999 |
| JP | 11-225359 | 8/1999 |
| JP | 2003-144417 | 5/2003 |
| JP | 2004-033438 | 2/2004 |
| JP | 2004-214014 | 7/2004 |
| JP | 2004-520103 | 7/2004 |
| JP | 2004-520898 | 7/2004 |
| JP | 2004-358016 | 12/2004 |
| JP | 2006-021031 | 1/2006 |
| JP | 2006-280464 | 10/2006 |
| JP | 2006-527036 | 11/2006 |
| JP | 2007-510499 | 4/2007 |
| JP | 2007-152037 | 6/2007 |
| JP | 2008-506468 | 3/2008 |
| KR | 10-2017-0068694 | 6/2017 |
| SU | 1281988 | 6/1989 |
| WO | WO 89/05119 | 9/1989 |
| WO | WO 89/08713 | 5/1990 |
| WO | WO 90/05300 | 5/1990 |
| WO | WO 90/05910 | 2/1991 |
| WO | WO 91/01680 | 4/1991 |
| WO | WO 91/04704 | 10/1991 |
| WO | WO 91/15993 | 8/1992 |
| WO | WO 92/13271 | 9/1994 |
| WO | WO 94/02062 | 2/1995 |
| WO | WO 95/28878 | 8/1996 |
| WO | WO 96/25089 | 11/1996 |
| WO | WO 96/35370 | 11/1996 |

(56) References Cited

FOREIGN PATENT DOCUMENTS

| | | |
|---|---|---|
| WO | WO 96/39977 | 12/1996 |
| WO | WO 97/02847 | 1/1997 |
| WO | WO 97/19344 | 5/1997 |
| WO | WO 97/21457 | 6/1997 |
| WO | WO 97/33513 | 9/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/04902 | 2/1998 |
| WO | WO 98/35053 | 8/1998 |
| WO | WO 98/56293 | 12/1998 |
| WO | WO 99/27849 | 6/1999 |
| WO | WO 99/28736 | 6/1999 |
| WO | WO 99/33504 | 7/1999 |
| WO | WO 99/56613 | 11/1999 |
| WO | WO 00/40159 | 7/2000 |
| WO | WO 00/49940 | 8/2000 |
| WO | WO 00/59370 | 10/2000 |
| WO | WO 00/60350 | 10/2000 |
| WO | WO 00/74753 | 12/2000 |
| WO | WO 00/78992 | 12/2000 |
| WO | WO 01/17875 A1 | 3/2001 |
| WO | WO 01/52727 A1 | 7/2001 |
| WO | WO 01/52935 | 7/2001 |
| WO | WO 01/54753 | 8/2001 |
| WO | WO 01/58348 | 8/2001 |
| WO | WO 02/15778 | 2/2002 |
| WO | WO 02/16905 | 2/2002 |
| WO | WO 02/50534 | 6/2002 |
| WO | WO 02/058537 | 8/2002 |
| WO | WO 02/100457 | 12/2002 |
| WO | WO 03/026728 | 4/2003 |
| WO | WO 03/028784 | 4/2003 |
| WO | WO 03/056319 | 7/2003 |
| WO | WO 03/057027 | 7/2003 |
| WO | WO 03/072164 | 9/2003 |
| WO | WO 03/073936 | 9/2003 |
| WO | WO 03/076893 | 9/2003 |
| WO | WO 03/082091 | 10/2003 |
| WO | WO 03/085372 | 10/2003 |
| WO | WO 2004/006982 | 1/2004 |
| WO | WO 2004/015539 | 2/2004 |
| WO | WO 2004/028337 | 4/2004 |
| WO | WO 2004/030726 | 4/2004 |
| WO | WO 2004/034024 | 4/2004 |
| WO | WO 2004/047445 | 6/2004 |
| WO | WO 2004/049237 | 6/2004 |
| WO | WO 2004/054445 | 7/2004 |
| WO | WO 2004/060436 | 7/2004 |
| WO | WO 2004/061420 | 7/2004 |
| WO | WO 2004/090503 | 10/2004 |
| WO | WO 2004/098405 | 11/2004 |
| WO | WO 2004/098682 A2 | 11/2004 |
| WO | WO 2004/098683 | 11/2004 |
| WO | WO 2004/098684 | 11/2004 |
| WO | WO 2004/098685 | 11/2004 |
| WO | WO 2004/107971 | 12/2004 |
| WO | WO 2004/112602 | 12/2004 |
| WO | WO 2005/011779 A1 | 2/2005 |
| WO | WO 2005/018450 | 3/2005 |
| WO | WO 2005/037184 | 4/2005 |
| WO | WO 2005/041766 | 5/2005 |
| WO | WO 2005/044116 | 5/2005 |
| WO | WO 2005/045744 | 5/2005 |
| WO | WO 2005/046780 | 5/2005 |
| WO | WO 2005/051170 | 6/2005 |
| WO | WO 2005/057175 | 6/2005 |
| WO | WO 2005/065538 | 7/2005 |
| WO | WO 2005/084534 | 9/2005 |
| WO | WO 2005/089103 | 9/2005 |
| WO | WO 2005/092177 | 10/2005 |
| WO | WO 2005/121785 | 12/2005 |
| WO | WO 2005/123186 | 12/2005 |
| WO | WO 2006/001024 | 1/2006 |
| WO | WO 2006/015922 | 2/2006 |
| WO | WO 2006/017358 | 2/2006 |
| WO | WO 2006/020212 | 2/2006 |
| WO | WO 2006/024671 | 3/2006 |
| WO | WO 2006/026741 | 3/2006 |
| WO | WO 2006/032653 | 3/2006 |
| WO | WO 2006/036145 | 4/2006 |
| WO | WO 2006/040083 | 4/2006 |
| WO | WO 2006/042811 | 4/2006 |
| WO | WO 2006/061354 | 6/2006 |
| WO | WO 2006/064397 | 6/2006 |
| WO | WO 2006/072035 | 7/2006 |
| WO | WO 2006/079114 | 7/2006 |
| WO | WO 2006/086423 | 8/2006 |
| WO | WO 2006/094513 | 9/2006 |
| WO | WO 2006/108809 | 10/2006 |
| WO | WO 2006/110742 | 10/2006 |
| WO | WO 2006/114297 | 11/2006 |
| WO | WO 2006/118947 | 11/2006 |
| WO | WO 2006/121921 | 11/2006 |
| WO | WO 2006/124099 | 11/2006 |
| WO | WO 2007/002189 | 1/2007 |
| WO | WO 2007/007459 | 1/2007 |
| WO | WO 2007/016399 | 2/2007 |
| WO | WO 2007/019289 | 2/2007 |
| WO | WO 2007/027788 | 3/2007 |
| WO | WO 2007/041069 | 4/2007 |
| WO | WO 2007/041070 | 4/2007 |
| WO | WO 2007/041248 | 4/2007 |
| WO | WO 2007/053832 | 5/2007 |
| WO | WO 2007/056638 | 5/2007 |
| WO | WO 2007/065285 | 6/2007 |
| WO | WO 2007/089738 | 8/2007 |
| WO | WO 2007/092618 | 8/2007 |
| WO | WO 2007/097754 | 8/2007 |
| WO | WO 2007/101223 | 9/2007 |
| WO | WO 2007/120363 | 10/2007 |
| WO | WO 2007/126444 | 11/2007 |
| WO | WO 2007/140783 | 12/2007 |
| WO | WO 2007/143225 | 12/2007 |
| WO | WO 2007/149319 | 12/2007 |
| WO | WO 2008/001366 | 1/2008 |
| WO | WO 2008/014792 | 2/2008 |
| WO | WO 2008/021913 | 2/2008 |
| WO | WO 2008/031106 | 3/2008 |
| WO | WO 2008/031110 | 3/2008 |
| WO | WO 2008/039944 | 4/2008 |
| WO | WO 2008/042760 | 4/2008 |
| WO | WO 2008/048452 | 4/2008 |
| WO | WO 2008/051920 | 5/2008 |
| WO | WO 2008/051924 | 5/2008 |
| WO | WO 2008/052374 | 5/2008 |
| WO | WO 2008/061552 A1 | 5/2008 |
| WO | WO 2008/062099 | 5/2008 |
| WO | WO 2008/065646 | 6/2008 |
| WO | WO 2008/073813 | 6/2008 |
| WO | WO 2008/086541 | 7/2008 |
| WO | WO 2008/103620 | 8/2008 |
| WO | WO 2008/114223 | 9/2008 |
| WO | WO 2008/115409 | 9/2008 |
| WO | WO 2008/128210 | 10/2008 |
| WO | WO 2008/129532 | 10/2008 |
| WO | WO 2008/130896 | 10/2008 |
| WO | WO 2008/130897 | 10/2008 |
| WO | WO 2008/130898 | 10/2008 |
| WO | WO 2008/133702 | 11/2008 |
| WO | WO 2008/138006 | 11/2008 |
| WO | WO 2008/143943 | 11/2008 |
| WO | WO 2008/144445 | 11/2008 |
| WO | WO 2008/147921 | 12/2008 |
| WO | WO 2008/150917 | 12/2008 |
| WO | WO 2008/153693 | 12/2008 |
| WO | WO 2008/155377 | 12/2008 |
| WO | WO 2008/157821 | 12/2008 |
| WO | WO 2009/007287 | 1/2009 |
| WO | WO 2009/010396 | 1/2009 |
| WO | WO 2009/016635 | 2/2009 |
| WO | WO 2009/016638 | 2/2009 |

(56)                  References Cited

FOREIGN PATENT DOCUMENTS

| WO | WO 2009/018058 | 2/2009 | | |
|----|----|----|----|----|
| WO | WO 2009/035773 | 3/2009 | | |
| WO | WO 2009/039013 | 3/2009 | | |
| WO | WO 2009/062674 | 5/2009 | | |
| WO | WO 2009/062675 | 5/2009 | | |
| WO | WO 2009/066288 A1 | 5/2009 | | |
| WO | WO 2009/068661 | 6/2009 | | |
| WO | WO 2009/086216 | 7/2009 | | |
| WO | WO 2009/096992 | 8/2009 | | |
| WO | WO 2009/097594 | 8/2009 | | |
| WO | WO 2010/062898 | 6/2010 | | |
| WO | WO 2010/077329 | 7/2010 | | |
| WO | WO 2010/091005 | 8/2010 | | |
| WO | WO 2010/099507 | 9/2010 | | |
| WO | WO 2010/112521 | 10/2010 | | |
| WO | WO 2010/141922 | 12/2010 | | |
| WO | WO 2011/000528 | 1/2011 | | |
| WO | WO 2011/002815 | 1/2011 | | |
| WO | WO 2011/015659 | 2/2011 | | |
| WO | WO 2011/022418 | 2/2011 | | |
| WO | WO 2011/025549 | 3/2011 | | |
| WO | WO 2011/104616 | 9/2011 | | |
| WO | WO 2011/119896 | 9/2011 | | |
| WO | WO 2011/119898 A1 | 9/2011 | | |
| WO | WO 2012/103429 | 8/2012 | | |
| WO | WO 2013/090215 | 6/2013 | | |
| WO | WO 2016/183493 | 11/2016 | | |
| WO | WO 2017/027749 | 2/2017 | | |
| WO | WO 2017/116915 A1 | 7/2017 | | |
| WO | WO 2017/134227 | 8/2017 | | |
| WO | WO 2018/136898 | 7/2018 | | |
| WO | WO 2018/166963 | 9/2018 | | |
| WO | WO 2019/005627 A1 | 1/2019 | | |
| WO | WO 2019/236850 | 12/2019 | | |
| WO | WO 2019/236859 | 12/2019 | | |
| WO | WO 2019/236876 | 12/2019 | | |
| WO | WO-2019236876 A1 * | 12/2019 | ......... | A61B 5/14532 |
| WO | WO 2022/046416 A1 | 3/2022 | | |
| WO | WO 2022/060677 | 3/2022 | | |

OTHER PUBLICATIONS

AU, 2007309066 Examiner's Report, dated Aug. 16, 2013.
AU, 2008265541 Examiner's Report, dated Oct. 15, 2012.
AU, 2008265541 Examiner's Report, dated Nov. 29, 2013.
AU, 2010286917 Examiner's Report, dated Sep. 8, 2014.
AU, 2011230596 Examiner's Report, dated Feb. 28, 2014.
AU, 2011269796 Examiner's Report, dated Apr. 3, 2014.
AU, 2016201703 Examiner's Report, dated Mar. 22, 2017.
AU, 2017254903 Examiner's Report, dated Dec. 11, 2018.
AU, 2018200899 Examiner's Report, dated Dec. 6, 2018.
CA, 2,765,712 Examiner's Report, dated Apr. 10, 2017.
CA, 2,765,712 Examiner's Report, dated Mar. 27, 2018.
CA, 2,872,576 Examiner's Report, dated Feb. 17, 2015.
CA, 2,872,576 Examiner's Report, dated Feb. 19, 2016.
CN, 200780045373.9 Notice of Allowance, dated May 18, 2011.
CN, 200780045373.9 Office Action, dated Apr. 14, 2010.
CN, 201080027344.1 Office Action, dated Jun. 5, 2014.
CN, 201080027344.1 Office Action, dated Feb. 6, 2015.
CN, 201080006480.2 Office Action, dated May 6, 2013.
CN, 201080006480.2 Office Action, dated Dec. 11, 2013.
CN, 201080006481.7 Office Action, dated Dec. 2, 2014.
CN, 201180002616.7 Office Action, dated Apr. 24, 2014.
CN, 201180002617.1 Office Action, dated Jul. 3, 2014.
CN, 20160144860.1 Office Action, dated Mar. 23, 2018.
CN, 20160144860.1 Office Action, dated Dec. 10, 2018.
CN, 20160144860.1 Office Action, dated May 23, 2019.
EP, 06804122.7 Decision to Refuse the Application, dated Feb. 25, 2013.
EP, 06804122.7 Examination Report, dated Nov. 30, 2011.
EP, 06804122.7 Examination Report, dated Jan. 25, 2011.
EP, 06815715.5 Extended Search Report, dated Oct. 30, 2009.

EP, 06851063.5 Extended Search Report, dated Sep. 21, 2009.
EP, 07842173.2 Examination Report, dated Mar. 21, 2013.
EP, 07842173.2 Extended Search Report, dated Dec. 29, 2010.
EP, 07842180.7 Examination Report, dated Oct. 23, 2012.
EP, 07842180.7 Examination Report, dated Dec. 14, 2011.
EP, 07842180.7 Examination Report, dated Feb. 23, 2011.
EP, 07842180.7 Extended Search Report, dated Sep. 28, 2009.
EP, 07843396.8 Extended Search Report, dated Dec. 22, 2010.
EP, 10739015.5 Extended Search Report, dated May 10, 2013.
EP, 10739031.2 Extended Search Report, dated May 7, 2013.
EP, 10739031.2 Examination Report, dated Oct. 28, 2016.
EP, 10739031.2 Notice of Opposition, Dec. 20, 2018.
EP, 10739031.2 Reply to Notice of Opposition, May 21, 2019.
EP, 10739031.2 Reply to Notice of Opposition Reply, Aug. 8, 2019.
EP, 10739031.2 Summons to Attend Oral Proceedings, Sep. 17, 2019.
EP, 10739031.2 Written Submissions, Dec. 3, 2019.
EP, 10739031.2 Response to Written Submissions, Jan. 24, 2020.
EP, 10739031.2 Summons to Attend Oral Proceedings, May 20, 2020.
EP, 10739031.2 Written Submissions, Nov. 20, 2020.
EP, 10739031.2 Response to Written Submissions, Jan. 7, 2021.
EP, 10739031.2 Decision and Grounds for Revoking Patent, dated Jun. 9, 2021.
EP, 10739031.2 Grounds of Appeal, dated Oct. 19, 2021.
EP, 10739031.2 Response to Grounds of Appeal, dated Mar. 1, 2022.
EP, 10739031.2 Response to Response to Grounds of Appeal, dated Jul. 29, 2022.
EP, 10812438.9 Extended Search Report, dated Dec. 10, 2013.
EP, 11760268.0 Decision of the Oral Proceedings, Sep. 27, 2022.
EP, 11760268.0 Minutes of Oral Proceedings, Aug. 11, 2022.
EP, 11760268.0 Communication from Board of Appeals, Mar. 31, 2022.
EP, 11760268.0 Response to Written Submissions, Jan. 14, 2020.
EP, 11760268.0 Response to Notice of Appeal, Sep. 5, 2019.
EP, 11760268.0 Statement of Grounds of Appeal, Apr. 23, 2019.
EP, 11760268.0 Grounds of Appeal, Apr. 18, 2019.
EP, 11760268.0 Notice of Appeal Abbott Diabetes Care Inc., Feb. 25, 2019.
EP, 11760268.0 Notice of Appeal Dexcom, Feb. 22, 2019.
EP, 11760268.0 Interlocutory Decision, Dec. 13, 2018.
EP, 11760268.0 Response to Summons to Attend Oral Proceedings, Sep. 13, 2018.
EP, 11760268.0 Letter Regarding the Opposition Procedure, Sep. 12, 2018.
EP, 11760268.0 Summons to Attend Oral Proceedings, Mar. 22, 2018.
EP, 11760268.0 Comments on Reply to Notice of Opposition, Dec. 27, 2017.
EP, 11760268.0 Reply to Notice of Opposition, Sep. 4, 2017.
EP, 11760268.0 Notice of Opposition, Mar. 29, 2017.
EP, 11760268.0 Extended Search Report, dated Apr. 14, 2014.
EP, 13000104.3 Extended Search Report, dated Mar. 12, 2013.
EP, 13000105.0 Examination Report, dated Oct. 18, 2016.
EP, 13000105.0 Minutes of the Oral Proceedings, Oct. 18, 2016.
EP, 13000105.0 Notice of Opposition, Jan. 4, 2019.
EP, 14179905.6 Summons to Attend Oral Proceedings, Apr. 10, 2017.
EP, 14179905.6 Notice of Opposition, May 19, 2016.
EP, 14179905.6 Extended Search Report, dated Dec. 23, 2014.
EP, 15002441.2 Extended Search Report, dated Dec. 18, 2015.
EP, 15184320.8 Examination Report, dated Apr. 18, 2017.
EP, 16176370.1 Extended Search Report, dated Dec. 7, 2016.
EP, 16793637.6 Extended Search Report, dated Oct. 9, 2018.
EP, 17182379.2 Extended Search Report, dated Feb. 21, 2018.
EP, 17201183.5 Extended Search Report, dated May 7, 2018.
EP, 17201183.5 Examination Report, dated May 7, 2019.
EP, 18192278.2 Extended Search Report, dated Mar. 13, 2019.
EP, 18208224.8 Extended Search Report, dated Oct. 11, 2019.
EP, 18741791.0 Extended Search Report, dated Sep. 23, 2020.
EP, 19151577.4 Extended Search Report, dated Aug. 16, 2019.
EP, 19151577.4 Examination Report, dated May 27, 2022.

(56)  References Cited

OTHER PUBLICATIONS

EP, 19184881.1 Extended Search Report, dated Nov. 21, 2019.
EP, 19900891.3 Extended Search Report, dated Sep. 26, 2022.
EP, 20177703.4 Grounds of Opposition, Sep. 28, 2022.
EP, 20177703.4 Notice of Opposition, Sep. 28, 2022.
EP, 20177703.4 Examination Report, dated Jun. 25, 2021.
EP, 20177703.4 Extended Search Report, dated Sep. 25, 2020.
EP, 20177712.5 Extended Search Report, dated Sep. 30, 2020.
EP, 20195922.8 Extended Search Report, dated Dec. 16, 2020.
EP, 21152231.3 Extended Search Report, dated May 11, 2021.
EP, 21192910.4 Extended Search Report, dated Jan. 31, 2022.
EP, 21211041.5 Extended Search Report, dated Mar. 3, 2022.
EP, 22168031.7 Extended Search Report, dated Aug. 17, 2022.
EP, 22169853.3 Extended Search Report, dated Sep. 2, 2022.
IL, 198329 Office Action, dated Mar. 5, 2012.
JP, 2009-534798 Office Action, dated Sep. 25, 2012.
JP, 2012-526736 Office Action, dated Apr. 15, 2014.
JP, 2012-526736 Office Action, dated Dec. 16, 2014.
JP, 2013-501503 Office Action, dated Mar. 3, 2015.
JP, 2015-159805 Office Action, dated Aug. 9, 2016.
JP, 2016-44196 Office Action, dated Apr. 11, 2017.
MX, MX/a/2009/004398 Office Action, dated Sep. 24, 2012.
MY, PI2021004760 Examination Report, dated Mar. 30, 2022.
MY, PI2021005830 Examination Report, dated Mar. 30, 2022.
MY, PI2021005830 Examination Report, dated Aug. 29, 2022.
NL, 2009963 Search Report, dated Aug. 12, 2013.
US, Institution Decision, IPR No. 2022-00605, dated Jul. 27, 2022.
US, Patent Owner's Preliminary Sur-Reply, IPR No. 2022-00605, dated Jun. 28, 2022.
US, Petitioner's Preliminary Reply to Patent Owner's Preliminary Response, IPR No. 2022-00605, dated Jun. 21, 2022.
US, Patent Owner's Preliminary Response, IPR No. 2022-00605, dated May 24, 2022.
US, Petition for Inter Partes Review of U.S. Pat. No. 10,945,649, IPR No. 2022-00605, Feb. 15, 2022.
US, Institution Decision, IPR No. 2022-00637, dated Jul. 27, 2022.
US, Patent Owner's Preliminary Sur-Reply, IPR No. 2022-00637, dated Jun. 28, 2022.
US, Petitioner's Preliminary Reply to Patent Owner's Preliminary Response, IPR No. 2022-00637, dated Jun. 21, 2022.
US, Patent Owner's Preliminary Response, IPR No. 2022-00637, dated Jun. 9, 2022
US, Petition for Inter Partes Review of U.S. Pat. No. 11,013,440, IPR No. 2022-00637, Feb. 8, 2022.
US, Reexamination U.S. Appl. No. 95/002,162 Request to Review Order Denying Request for Reexamination, dated Dec. 13, 2012.
US, Reexamination U.S. Appl. No. 95/002,162 Order Denying Request for Reexamination, dated Nov. 13, 2012.
US, Request for Reexamination U.S. Appl. No. 95/002,162 of U.S. Pat. No. 8,175,673, dated Sep. 7, 2012.
US, Reexamination U.S. Appl. No. 95/002,113 Request to Review Order Denying Request for Reexamination, dated Dec. 13, 2012.
US, Reexamination U.S. Appl. No. 95/002,113 Order Denying Request for Reexamination, dated Nov. 13, 2012.
US, Request for Reexamination U.S. Appl. No. 95/002,113 of U.S. Pat. No. 6,990,366, dated Aug. 30, 2012.
US, Reexamination U.S. Appl. No. 90/011,730 Notice of Intent to Issue Ex Parte Reexamination Certificate, dated Apr. 5, 2012.
US, Reexamination U.S. Appl. No. 90/011,730 Office Action, dated Jan. 11, 2012.
US, Reexamination U.S. Appl. No. 90/011,730 Order Granting Request for Reexamination, dated Aug. 24, 2011.
US, Request for Reexamination U.S. Appl. No. 90/011,730 of U.S. Pat. No. 6,990,366, dated Jun. 3, 2011.
US, Reexamination U.S. Appl. No. 90/010,791 Ex Parte Reexamination Certificate, dated May 17, 2011.
US, Reexamination U.S. Appl. No. 90/010,791 Office Action, dated Dec. 17, 2010.
US, Reexamination U.S. Appl. No. 90/010,791 Office Action, dated May 28, 2010.
US, Reexamination U.S. Appl. No. 90/010,791 Order Granting Request for Reexamination, dated Feb. 22, 2010.
US, Request for Reexamination U.S. Appl. No. 90/010,791 of U.S. Pat. No. 6,990,366, dated Dec. 22, 2009.
US, Reexamination U.S. Appl. No. 90/009,328 Notice of Intent to Issue Ex Parte Reexamination Certificate, dated Nov. 20, 2009.
US, Reexamination U.S. Appl. No. 90/009,328 Office Action, dated Sep. 30, 2009.
US, Reexamination U.S. Appl. No. 90/009,328 Office Action, dated Aug. 4, 2009.
US, Reexamination U.S. Appl. No. 90/009,328 Order Granting Request for Reexamination, dated Dec. 9, 2008.
US, Request for Reexamination U.S. Appl. No. 90/009,328 of U.S. Pat. No. 6,990,366, dated Nov. 10, 2008.
US, Reexamination U.S. Appl. No. 90/009,104 Notice of Intent to Issue Ex Parte Reexamination Certificate, dated Nov. 20, 2009.
US, Reexamination U.S. Appl. No. 90/009,104 Office Action, dated Sep. 30, 2009.
US, Reexamination U.S. Appl. No. 90/009,104 Office Action, dated Aug. 4, 2009.
US, Reexamination U.S. Appl. No. 90/009,104 Office Action, dated Oct. 16, 2008.
US, Reexamination U.S. Appl. No. 90/009,104 Order Granting Request for Reexamination, dated Jun. 5, 2008.
US, Request for Reexamination U.S. Appl. No. 90/009,104 of U.S. Pat. No. 6,990,366, dated Apr. 8, 2008.
US, Reexamination U.S. Appl. No. 90/008,457 Notice of Intent to Issue Ex Parte Reexamination Certificate, dated Mar. 13, 2008.
US, Reexamination U.S. Appl. No. 90/008,457 Order Granting Request for Reexamination, dated Feb. 23, 2007.
US, Request for Reexamination U.S. Appl. No. 90/008,457 of U.S. Pat. No. 6,990,366, dated Jan. 23, 2007.
US, Request for Reexamination U.S. Appl. No. 90/008,172 of U.S. Pat. No. 6,990,366, dated Aug. 16, 2006.
US, Reexamination U.S. Appl. No. 90/007,910 Patent Board Decision, dated May 17, 2013.
US, Reexamination U.S. Appl. No. 90/007,910 Decision on Appeal, dated Jan. 18, 2011.
US, Reexamination U.S. Appl. No. 90/007,910 Advisory Action, dated Jul. 30, 2009.
US, Reexamination U.S. Appl. No. 90/007,910 Advisory Action, dated Feb. 6, 2009.
US, Reexamination U.S. Appl. No. 90/007,910 Examiner's Answer to Appeal Brief, dated Nov. 19, 2009.
US, Reexamination U.S. Appl. No. 90/007,910 Office Action, dated Oct. 2, 2008.
US, Reexamination U.S. Appl. No. 90/007,910 Office Action, dated Feb. 13, 2008.
US, Reexamination U.S. Appl. No. 90/007,910 Order Granting Request for Reexamination, dated Mar. 27, 2006.
US, Request for Reexamination U.S. Appl. No. 90/007,910 of U.S. Pat. No. 6,175,752, dated Feb. 1, 2006.
US, Reexamination U.S. Appl. No. 90/009,270 Order Denying Request for Reexamination, dated Dec. 1, 2008.
US, Request for Reexamination U.S. Appl. No. 90/009,270 of U.S. Pat. No. 6,175,752, dated Sep. 8, 2008.
US, Reexamination U.S. Appl. No. 90/009,497 Notice of Intent to Issue Reexamination Certificate, dated Aug. 23, 2010.
US, Reexamination U.S. Appl. No. 90/009,497 Order Granting Request, dated Jul. 30, 2009.
US, Request for Reexamination U.S. Appl. No. 90/009,497 of U.S. Pat. No. 6,175,752, dated Jun. 17, 2009.
WO, PCT/US2006/037312 ISR and Written Opinion, dated Apr. 17, 2007.
WO, PCT/US2006/037928 ISR and Written Opinion, dated Jul. 11, 2008.
WO, PCT/US2006/062690 ISR and Written Opinion, dated Jan. 2, 2008.
WO, PCT/US2007/078065 ISR and Written Opinion, dated Apr. 11, 2008.
WO, PCT/US2007/078073 ISR and Written Opinion, dated Apr. 11, 2008.

(56)        References Cited

OTHER PUBLICATIONS

WO, PCT/US2007/079774 ISR and Written Opinion, dated Apr. 1, 2008.
WO, PCT/US2007/082114 ISR and Written Opinion, dated May 9, 2008.
WO, PCT/US2010/002401 ISR and Written Opinion, dated Nov. 12, 2010.
WO, PCT/US2010/022860 ISR and Written Opinion, dated Mar. 23, 2010.
WO, PCT/US2010/022928 ISR and Written Opinion, dated Mar. 21, 2010.
WO, PCT/US2010/047381 ISR and Written Opinion, dated Oct. 15, 2010.
WO, PCT/US2010/050772 ISR and Written Opinion, dated Dec. 3, 2010.
WO, PCT/US2010/050888 ISR and Written Opinion, dated Nov. 29, 2010.
WO, PCT/US2010/051861 ISR and Written Opinion, dated Nov. 30, 2010.
WO, PCT/US2011/029881 ISR and Written Opinion, dated May 20, 2011.
WO, PCT/US2011/029883 ISR and Written Opinion, dated Jun. 2, 2011.
WO, PCT/US2011/029884 ISR and Written Opinion, dated Jun. 1, 2011.
WO, PCT/US2012/068839 ISR and Written Opinion, dated Feb. 22, 2013.
WO, PCT/US2013/052397 ISR and Written Opinion, dated Dec. 2, 2013.
WO, PCT/US2016/032485 ISR and Written Opinion, dated Sep. 12, 2016.
WO, PCT/US2018/014745 ISR and Written Opinion, dated Jun. 4, 2018.
WO, PCT/US2019/035843 ISR and Written Opinion, dated Sep. 18, 2019.
WO, PCT/US2021/040541 ISR and Written Opinion, dated Dec. 20, 2021.
WO, PCT/US2021/045576 ISR and Written Opinion, dated Jan. 27, 2022.
WO, PCT/US2021/048086 ISR and Written Opinion, dated Feb. 28, 2022.
WO, PCT/US2021/050672 ISR and Written Opinion, dated Jan. 5, 2022.
WO, PCT/US2022/037291 Invitation to Pay Additional Fees, dated Sep. 29, 2022.
WO, PCT/US2022/037291 ISR and Written Opinion, dated Nov. 22, 2022.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
Accu-Chek Compact Plus Owner's Booklet, 2008, pp. 1-100.
Accu-Chek Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Affidavit of Richard Paragas signed on May 18, 2016, pp. 1-4.
Affidavit of Paul Neale signed on May 18, 2016, pp. 1-2.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.

Alcock, S J, et al., "Continuous analyte monitoring to aid clinical practice," IEEE Engineering in Medicine & BioloXY Magazine, 1994, vol. 13. pp. 319-325.
Ambade, V. N., et al., "Methods for Estimation of Blood Glucose: A Comparative Evaluation", Medical Journal Armed Forces India, 1998, vol. 54, No. 2, pp. 131-133.
Anderson, L. B., et al., "Thin-Layer Electrochemistry: Steady-State Methods of Studying Rate Processes", Journal of ElectroAnalytical Chemistry, 1965, vol. 10, pp. 295-305.
Application Note AN048, Antenna Part No. FR05-S1-N-0-102, Compact Reach Xtend™, Bluetooth®, 802.11b/g WLAN Chip Antenna, 2008, pp. 1-13.
Application Note AVR2023—AT86RF231 PCB reference design for antenna diversity, Atmel Corporation, 2008, pp. 1-15.
Application Note nRF9E5 RF and antenna layout, Nordic Semiconductor, 2006, pp. 1-13.
Armour, J. C., et al., "Application of Chronic Intravascular Blood Glucose Sensor in Dogs," Diabetes, 1990, vol. 39, pp. 1519-1526.
ASTM International, Designation D2240-05, 2010, pp. 1-13.
Aussedat, B., et al., "A User-Friendly Method for Calibrating a Subcutaneous Glucose Sensor-Based Hypoglycemic Alarm", Biosensors & Bioelectronics, 1997, vol. 12, No. 11, pp. 1061-1071.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Benkič, K., et al., "Using RSSI value for distance estimation in Wireless sensor networks based on ZigBee", 15th International Conference on Systems, Signals and Image Processing, Bratislava, Slovakia, 2008, pp. 1-4.
Bennion, N., et al., "Alternate Site Glucose Testing: A Crossover Design", Diabetes Technology & Therapeutics, 2002, vol. 4, No. 1, pp. 25-33.
Bindra, D.S., et al., "Pulsed Amperometric Detection of Glucose in Biological Fluids at a Surface-Modified Gold Electrode", American Chemical Society, 1989, vol. 61, No. 22, pp. 2566-2570.
Bindra, D.S., et al., "Design and in Vitro Studies of a Needle-Type Glucose Sensor for Subcutaneous Monitoring," Anal. Chem., 1991, vol. 63, No. 17, pp. 1692-1696.
Biosensors: Fundamentals and Applications, Turner et al., Eds., 1987, pp. 1-786.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, 2002, vol. 4624, pp. 1-10.
"Bluetooth Antenna Design", National Semiconductor Application Note, 2005, pp. 1-16.
Bluetooth Core Specification 4.0, Jun. 30, 2010, Master Table of Contents & Compliance Requirements, pp. 1-89.
Bobbioni-Harsch, E. et al., "Lifespan of subcutaneous glucose sensors and their performances during dynamic glycaemia changes in rats," J. Biomed. Eng., 1993, vol. 15, pp. 457-463.
Bonnett, A. H., et al., "Squirrel-Cage Rotor Options for AC Induction Motors", IEEE Transactions on Industry Applications, 2001, vol. 37, No. 4, pp. 1197-1209.
Brandt, J., et al., "Covalent Attachment of Proteins to Polysaccharide Carriers by Means of Benzoquinone", Biochimica et Biophysica Acta, 1975, vol. 386, pp. 196-202.
Brooks, S. L., et al., "Development of an On-Line Glucose Sensor for Fermentation Monitoring", Biosensors, 1987/88, vol. 3, pp. 45-56.
Brownlee, M., et al., "A Glucose-Controlled Insulin-Delivery System: Semisynthetic Insulin Bound to Lectin", Science, 1979, vol. 206, pp. 1190-1191.
Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.

(56)         References Cited

OTHER PUBLICATIONS

Callaway, Jr., E. H., "Wireless Sensor Networks: Architectures and Protocols", 2004, Chapter 8, Antennas and the Definition of RF Performance, pp. 201-202.

Cass, A.E.G. et al., "Ferrocene-Mediated Enzyme Electrode for Amperometric Determination of Glucose," Anal. Chem., 1984, vol. 56, No. 4, pp. 667-671.

Cass, A.E.G. et al., "Ferricinium Ion as an Electron Acceptor for Oxido-Reductases", Journal of ElectroAnalytical Chemistry, 1985, vol. 190, pp. 117-127.

Castner, J. F., et al., "Mass Transport and Reaction Kinetic Parameters Determined Electrochemically for Immobilized Glucose Oxidase", Biochemistry, 1984, vol. 23, No. 10, pp. 2203-2210.

Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.

Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.

Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.

Claremont, D. J., et al., "Biosensors for Continuous In Vivo Glucose Monitoring", Proceedings of the Annual International Conference of the IEEE Engineering in Medicine and Biology Society, 1988, vol. 10, pp. 1-2.

Clark Jr., L. C., et al., "Electrode Systems for Continuous Monitoring in Cardiovascular Surgery", Annals New York Academy of Sciences, 1962, pp. 29-45.

Clark Jr., L. C., et al., "Differential Anodic Enzyme Polarography for the Measurement of Glucose", Oxygen Transport to Tissue: Instrumentation, Methods, and Physiology, 1973, pp. 127-133.

Clark Jr., L. C., et al., "Long-term Stability of Electroenzymatic Glucose Sensors Implanted in Mice", American Society of Artificial Internal Organs Transactions, 1988, vol. XXXIV, pp. 259-265.

Clarke, W. L., et al., "Evaluating Clinical Accuracy of Systems for Self-Monitoring of Blood Glucose", Diabetes Care, 1987, vol. 10, No. 5, pp. 622-628.

Clarke, W., et al., "Statistical Tools to Analyze Continuous Glucose Monitor Data", Diabetes Technology & Therapeutics, 2009, vol. 11, Suppl. 1, pp. S-45-S-54.

Cleo™ 90 Infusion Set, 510(k) Summary of Safety and Effectiveness, Aug. 10, 2004, pp. 1-618.

Cleo® 90 Infusion Set Training Guide, 2011, 1 page.

Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.

Complaint *Abbott Diabetes Care Inc.* v. *Dexcom, Inc.* U.S. District Court Delaware C.A. No. 05-590 filed Aug. 11, 2005.

Complaint, Amended, *Abbott Diabetes Care Inc.* v. *Dexcom, Inc.* U.S. District Court Delaware C.A. No. 05-590 filed Jun. 27, 2006.

Complaint *Abbott Diabetes Care Inc.* v. *Dexcom, Inc.* U.S. District Court Delaware C.A. No. 06-514 filed Aug. 17, 2006.

Cox, M., "An Overview of Continuous Glucose Monitoring Systems", Journal of Pediatric Health Care, 2009, vol. 23, No. 5, pp. 344-347.

Csöregi, E., et al., "Design and Optimization of a Selective Subcutaneously Implantable Glucose Electrode Based on 'Wired' Glucose Oxidase", Analytical Chemistry, 1995, vol. 67, No. 7, pp. 1240-1244.

Csöregi, E., et al., "Design, Characterization, and One-Point in Vivo Calibration of a Subcutaneously Implanted Glucose Electrode", Analytical Chemistry, 1994, vol. 66 No. 19, pp. 3131-3138.

Csöregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.

Cullen, M.T., et al., "The Changing Presentations of Diabetic Ketoacidosis During Pregnancy", Amer. J. Perinatol, 1996, vol. 13, No. 7, pp. 449-451 (abstract only).

In Vivo Glucose Sensing, Cunningham et al., Eds., 2010, Chemical Analysis, vol. 174, pp. 1-466.

Darley, J., "Is your user experience as good as your technology?", 2019, retrieved from https://www.massdevice.com/is-your-user-experience-as-good-as-your-technology/, pp. 1-16.

Davis, G., "Electromechanical Techniques for the Development of Amperometric Biosensors", Biosensors, 1985, vol. 1, pp. 161-178.

IPR2022-00605 (Ex. 2001) Declaration of Michael Cima, Ph.D dated May 24, 2022, pp. 1-70.

IPR2022-00637 (Ex. 2001) Declaration of Michael Cima, Ph.D dated Jun. 9, 2022, pp. 1-79.

IPR2022-00605 (Ex. 1003) Declaration of Gary D. Fletcher, Ph.D dated Feb. 15, 2022, pp. 1-122.

IPR2022-00605 (Ex. 1003) Corrected Declaration of Gary D. Fletcher, Ph.D dated Feb. 18, 2022, pp. 1-124.

IPR2022-00637 (Ex. 1035) Second Declaration of Gary D. Fletcher, Ph.D dated Feb. 28, 2022, pp. 1-136.

Decuir, J., "Bluetooth 4.0: Low Energy", IEEE SCV Consultants' Network of Silicon Valley, 2012, pp. 1-68.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.

Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.

Dehez, B., et al., "Development of a Spherical Induction Motor With Two Degrees of Freedom", IEEE Transactions on Magnetics, 2006, vol. 42, No. 8, pp. 2077-2089.

Delve Talks: Jake Leach, Dexcom, retrieved from https://www.delve.com/podcasts/delve-talks-jake-leach-dexcom, 2019, pp. 1-9.

Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.

Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.

"Dexcom CEO tells investors not to fear new competition from Abbott's Freestyle Libre", 2017, retrieved from https://www.mobihealthnews.com/content/dexcom-ceo-tells-investors-not-fear-new-competition-abbotts-freestyle-libre, pp. 1-3.

Dexcom G5 Mobile System User Guide, 2020, pp. 1-410.

Dexcom G6, Winner Health & Wellness Award, Core77 Design Awards, 2019, retrieved from https://designawards.core77.com/health-wellness/85111/Dexcom-G6, pp. 1-8.

DexCom™ STS™ Continuous Glucose Monitoring System User's Guide, 2006, pp. 1-57.

Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.

Diem, P., et al., "Clinical Performance of a Continuous Viscometric Affinity Sensor for Glucose", Diabetes Technology & Therapeutics, 2004, vol. 6, pp. 790-799.

ECMA International Standard ECMA-340, Near Field Communication Interface and Protocol (NFCIP-1), 2nd Edition, 2004, pp. 1-65.

(56)                References Cited

OTHER PUBLICATIONS

El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, 2007, vol. 1, No. 2, pp. 181-192.

Ellis, C. D., et al., "Selectivity and Directed Charge Transfer through an Electroactive Metallopolymer Film", Journal of the American Chemical Society, 1981, vol. 103, No. 25, pp. 7480-7483.

Engstrom, R. C., "Electrochemical Pretreatment of Glassy Carbon Electrodes", Analytical Chemistry, 1982, vol. 54, No. 13, pp. 2310-2314.

Engstrom, R. C., et al., "Characterization of Electrochemically Pretreated Glassy Carbon Electrodes", Analytical Chemistry, 1984, vol. 56, No. 2, pp. 136-141.

Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.

Feldman, B., et al., "Electron Transfer Kinetics at Redox Polymer/ Solution Interfaces Using Microelectrodes and Twin Electrode Thin Layer Cells", Journal of ElectroAnalytical Chemistry, 1985, vol. 194, pp. 63-81.

Feldman, B., et al., "A Continuous Glucose Sensor Based on Wired Enzyme™ Technology—Results from a 3-Day Trial in Patients with Type 1 Diabetes", Diabetes Technology & Therapeutics, 2003, vol. 5, No. 5, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

File History of U.S. Pat. No. 10,292,632.

File History of U.S. Pat. No. 10,945,649.

File History of U.S. Pat. No. 11,013,440.

U.S. Appl. No. 60/587,787.

U.S. Appl. No. 12/250,760.

Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.

Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.

Foulds, N. C., et al., "Immobilization of Glucose Oxidase in Ferrocene-Modified Pyrrole Polymers", Analytical Chemistry, 1988, vol. 60, No. 22, pp. 2473-2478.

Freedman, D., et al., Statistics: Second Edition, 1991, Chapter 5, p. 74.

Freestyle Navigator Continuous Glucose Monitor FDA Premarket Approval (PMA), May 2022, pp. 1-6.

Freestyle Navigator Summary of Safety and Effectiveness Data, 2008, pp. 1-27.

Freestyle Navigator User's Guide, 2008, pp. 1-195.

Frenzel, L. E., "Printed-Circuit-Board Antennas", retrieved from https://www.electronicdesign.com/technologies/boards/article/21751417/printedcircuitboard-antennasprint/3266, Electronic Design, 2005, pp. 1-4.

Frew, J. E., et al., "Electron-Transfer Biosensors", Philosophical Transactions of the Royal Society of London, 1987, vol. 316, pp. 95-106.

Fujipoly Silver ZEBRA® Connector Data Sheet FSDS 01-34, Version 5, 2006, pp. 1-7.

Garg, S., et al., "Improvement in Glycemic Excursions with a Transcutaneous, Real-Time Continuous Glucose Sensor", Diabetes Care, 2006, vol. 29, No. 1, pp. 44-50.

Garibotto, J., et al., "An Innovative Application of Shape Memory Alloy Technology Yields a Novel Therapeutic Approach to Diabetes Management", Insulet Corporation, 2006, p. A41.

Gilligan, B. J., et al., "Evaluation of a Subcutaneous Glucose Sensor out to 3 Months in a Dog Model", Diabetes Care, 1994, vol. 17, No. 8, pp. 882-887.

Gonzales, W. V., et al., "The Progress of Glucose Monitoring—A Review of Invasive to Minimally and Non-Invasive Techniques, Devices and Sensors", Sensors, 2019, vol. 19, No. 800, pp. 1-45.

Gonzalez, O. L., et al., "Low-Cost Wireless Sensors—Designer Reference Manual", Freescale Semiconductor, 2007, pp. 1-146.

Gorton, L., et al., "Selective Detection in Flow Analysis Based on the Combination of Immobilized Enzymes and Chemically Modified Electrodes", Analytica Chimica Acta, 1991, vol. 250, pp. 203-248.

Gregg, B. A., et al., "Cross-Linked Redox Gels Containing Glucose Oxidase for Amperometric Biosensor Applications," Analytical Chemistry, 1990, vol. 62, No. 3, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.

Gregg, T. H., "How Continuous Glucose Monitoring is Transforming Diabetes Treatment", Qualcomm Life Connect, 2013, pp. 1-33.

Guardian® RT Continuous Glucose Monitoring System REF MMT-7900 User Guide, 2005, pp. 1-128.

Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.

Guerra, S., et al., "A Dynamic Risk Measure from Continuous Glucose Monitoring Data", Diabetes Technology & Therapeutics, 2011, vol. 13, No. 8, pp. 843-852.

Güler, N. F., et al., "Theory and Applications of Biotelemetry", Journal of Medical Systems, 2002, vol. 26, No. 2, pp. 159-178.

Gunasingham, et al., "Electrochemically Modulated Optrode for Glucose", Biosensors & Bioelectronics, 1992, vol. 7, pp. 353-359.

Hale, P. D., et al., "A New Class of Amperometric Biosensor Incorporating a Polymeric Electron-Transfer Mediator", Journal of the American Chemical Society, 1989, vol. 111, No. 9, pp. 3482-3484.

Hao, Y., "Wireless body sensor networks for health-monitoring applications", Physiol. Meas., 2008, vol. 29, R27-R56.

Harrison, D. J. et al., "Characterization of Perfluorosulfonic Acid Polymer Coated Enzyme Electrodes and a Miniaturized Integrated Potentiostat for Glucose Analysis in Whole Blood," Anal. Chem., 1988, vol. 60, No. 19, pp. 2002-2007.

Hawkridge, F. M., et al., "Indirect Coulometric Titration of Biological Electron Transport Components", Analytical Chemistry, 1973, vol. 45, No. 7, pp. 1021-1027.

Heftman, G., "Chip Antenna Reduces Cell-Phone Dimensions", Microwaves & RF, 1999, p. 182.

Heise, T., et al., "Hypoglycemia Warning Signal and Glucose Sensors: Requirements and Concepts", Diabetes Technology & Therapeutics, 2003, vol. 5, No. 4, pp. 563-571.

Heller, A., "Electrical Connection of Enzyme Redox Centers to Electrodes," J. Phys. Chem., 1992, vol. 96, No. 9, pp. 3579-3587.

Heller, A., "Electrical Wiring of Redox Enzymes," Acc. Chem. Res., 1990, vol. 23, No. 5, pp. 129-134.

Heller, A., et al., "Amperometric Biosensors Based on Three-Dimensional Hydrogel-Forming Epoxy Networks", Sensors and Actuators B, 1993, vol. 13-14, pp. 180-183.

Heller, A., "Implanted Electrochemical Glucose Sensors for the Management of Diabetes", Annnu. Rev. Biomed. Eng., 1999, vol. 1, pp. 153-175.

Hirsch, I. B., "Introduction: History of Glucose Monitoring", Clinical Compendia, 2018, vol. 2018, No. 1, 1 page.

Hoel, P. G., Elementary Statistics: Fourth Edition, 1976, Chapter 5, pp. 113-114.

Howe, D., "Comparing the Dexcom G6 to the G5", 2018, retrieved from https://beyondtype1.org/comparing-the-dexcom-g6-to-the-g5/, pp. 1-10.

Huang, Y., et al., "Antennas from Theory to Practice", 2008, Chapter 8, Antenna Diversity, pp. 322-325.

(56) References Cited

OTHER PUBLICATIONS

Ianniello, R. M., et al., "Immobilized Enzyme Chemically Modified Electrode as an Amperometric Sensor", Analytical Chemistry, 1981, vol. 53, No. 13, pp. 2090-2095.

Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.

Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.

Ikeda, T., et al., "Glucose Oxidase—Immobilized Benzoquinone-Carbon Paste Electrode as a Glucose Sensor", Agricultural and Biological Chemistry, 1985, vol. 49, No. 2, pp. 541-543.

Ikeda, T., et al., "Artificial Pancreas—Investigation of the Stability of Glucose Sensors Using a Telemetry System" (English language translation of abstract), Jpn. J. Artif. Organs, 1990, vol. 19, No. 2, pp. 889-892.

"In Vitro Diagnostic Products for Human Use", Federal Register, 1974, vol. 39, No. 126, pp. 24136-24147.

Isermann, R., "Supervision, Fault-Detection and Fault-Diagnosis Methods—An Introduction", Control Engineering Practice, 1997, vol. 5, No. 5, pp. 639-652.

Isermann, R., et al., "Trends in the Application of Model-Based Fault Detection and Diagnosis of Technical Processes", Control Engineering Practice, 1997, vol. 5, No. 5, pp. 709-719.

Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.

James, Jr., et al., "Handbook of Microstrip Antennas", 1969, pp. 1038-1047.

Johnson, J. M., et al., "Potential-Dependent Enzymatic Activity in an Enzyme Thin-Layer Cell", Analytical Chemistry, 1982, vol. 54, No. 8, pp. 1377-1383.

Johnson, K. W., "Reproducible Electrodeposition of Biomolecules for the Fabrication of Miniature Electroenzymatic Biosensors", Sensors and Actuators B, 1991, vol. 5, pp. 85-89.

Johnson, K. W., et al., "In vivo evaluation of an electroenzymatic glucose sensor implanted in subcutaneous tissue," Biosensors and Bioelectronics, 1992, vol. 7, pp. 709-714.

Johnson, P. C., "Peripheral Circulation", John Wiley & Sons, 1978, p. 198.

Jönsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.

Josowicz, M., et al., "Electrochemical Pretreatment of Thin Film Platinum Electrodes", Journal of the Electrochemical Society, 1988, vol. 135, No. 1, pp. 112-115.

Jovanovic, L., "The Role of Continuous Glucose Monitoring in Gestational Diabetes Mellitus", Diabetes Technology & Therapeutics, 2000, vol. 2, Supplement 1, pp. S-67-S-71.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, 2001, vol. 24, No. 7, pp. 1303-1304.

Kaplan, S. M., "Wiley Electrical and Electronics Engineering Dictionary", IEEE Press, 2004, pp. 141, 142, 548, 549.

Katakis, I., et al., "L-$\alpha$-Glycerophosphate and $_L$-Lactate Electrodes Based on the Electrochemical 'Wiring' of Oxidases", Analytical Chemistry, 1992, vol. 64, No. 9, pp. 1008-1013.

Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.

Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine) $_2$Cl] $^{+/2+}$", Journal of the Chemical Society, Faraday Transactions, 1996, vol. 92, No. 20, pp. 4131-4136.

Klonoff, D. C., "A Review of Continuous Glucose Monitoring Technology", Diabetes Technology & Therapeutics, 2005, vol. 7, No. 5, pp. 770-775.

Kondepati, V., et al., "Recent Progress in Analytical Instrumentation for Glycemic Control in Diabetic and Critically Ill Patients", Analytical Bioanalytical Chemistry, 2007, vol. 388, pp. 545-563.

Koudelka, M., et al., "In-Vivo Behaviour of Hypodermically Implanted Microfabricated Glucose Sensors", Biosensors & Bioelectronics, 1991, vol. 6, pp. 31-36.

Kovatchev, B. P., et al., "Evaluating the Accuracy of Continuous Glucose-Monitoring Sensors", Diabetes Care, 2004, vol. 27, No. 8, pp. 1922-1928.

Kulys, J., et al., "Mediatorless Peroxidase Electrode and Preparation of Bienzyme Sensors", Bioelectrochemistry and Bioenergetics, 1990, vol. 24, pp. 305-311.

Lager, W., et al., "Implantable Electrocatalytic Glucose Sensor", Hormone Metabolic Research, 1994, vol. 26, pp. 526-530.

León, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.

Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, 2003, vol. 5, No. 4, pp. 573-587.

Lortz, J., et al., "What is Bluetooth? We Explain The Newest Short-Range Connectivity Technology", Smart Computing Learning Series, Wireless Computing, 2002, vol. 8, Issue 5, pp. 72-74.

Loy, M., et al., "ISM-Band and Short Range Device Antennas", Texas Instruments Application Report, 2005, pp. 1-38.

Maidan, R. et al., "Elimination of Electroaxidizable Interferant-Produced Currents in Amperometric Biosensors," Analytical Chemistry, 1992, vol. 64, No. 23, pp. 2889-2896.

Malin, S. F., et al., "Noninvasive Prediction of Glucose by Near-Infrared Diffuse Reflectance Spectoscopy", Clinical Chemistry, 1999, vol. 45, No. 9, pp. 1651-1658.

Mastrototaro, J.J., et al., "An Electroenzymatic Glucose Sensor Fabricated on a Flexible Substrate," Sensors and Biosensors B Chemical, 1991, B5, pp. 139-144.

Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, 2001, vol. 3, No. 3, pp. 367-376.

McKean, B., et al., "A Telemetry-Instrumentation System for Chronically Implanted Glucose and Oxygen Sensors," IEEE Transactions on Biomedical Engineering, 1988, vol. 35, No. 7, pp. 526-532.

McNeil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.

Medtronic Guardian® REAL-Time Continuous Glucose Monitoring System User Guide, 2006, pp. 1-184.

IPR2022-00605 (Ex. 1027) The Merriam-Webster Dictionary, Merriam Webster, Incorporated (2005), pp. 66, 403, and 415.

Microchip Technology Inc., MRF24J40MA Data Sheet, 2008, pp. 1-30.

(56) References Cited

OTHER PUBLICATIONS

IPR2022-00605 (Ex. 2008) MiniMed® Glucose Sensor, REF MMT-7002, Instructions for Use, May 1999, pp. 1-4.

Minimed Technologies, "Tape Tips and Other Infusion Site Information", 1995.

Minimed Quick-set™ retrieved from https://web.archive.org/web/20010412224824/http://www.minimed.com/patientfam/pf_ipt_pumpinfusion_quickset.shtml, Apr. 12, 2001, pp. 1-2.

Minimed Sof-set Micro QR® Sof-set Ultimate QR® retrieved from https://web.archive.org/web/20010412225617/http://www.minimed.com/patientfam/pf_ipt_pumpinfusion_sofset.shtml, Apr. 12, 2001, pp. 1-2.

Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.

Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, 1992, vol. 7, pp. 345-352.

Moatti-Sirat, D., et al., "Reduction of Acetaminophen Interference in Glucose Sensors by a Composite Nafion Membrane: Demonstration in Rats and Man", Diabetologia, 1994, vol. 37, pp. 610-616.

Moatti-Sirat, D., et al., "Towards Continuous Glucose Monitoring: In Vivo Evaluation of a Miniaturized Glucose Sensor Implanted For Several Days in Rat Subcutaneous Tissue," Diabetolocia, 1992, vol. 35, No. 3 (1 page—Abstract only).

IPR2022-00605 (Ex. 2003) "Monitoring Your Blood Sugar", retrieved from https://www.cdc.gov/diabetes/managing/managing-blood-sugar/bloodglucosemonitoring.html, 2021, pp. 1-3.

Moore, B., "The Potential Use of Radio Frequency Identification Devices for Active Monitoring of Blood Glucose Levels", Journal of Diabetes Science and Technology, 2009, vol. 3, No. 1, pp. 180-183.

Morak, J., et al., "Design and Evaluation of a Telemonitoring Concept Based on NFC- Enabled Mobile Phones and Sensor Devices", IEEE Transactions on Information Technology in Biomedicine, 2012, vol. 16, No. 1, pp. 17-23.

Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.

Mougiakakou, S. G., et al., "A Real Time Simulation Model of Glucose-Insulin Metabolism for Type 1 Diabetes Patients", Proceedings of the 2005 IEEE, 2005, pp. 298-301.

Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.

"Murata Puts Antenna on a Chip", Passives, 1999, vol. 44, 1 page.

Nagy, G., et al., "A New Type of Enzyme Electrode: The Ascorbic Acid Eliminator Electrode", Life Sciences, 1982, vol. 31, No. 23, pp. 2611-2616.

Nakamura, S., et al., "Effect of Periodate Oxidation on the Structure and Properties of Glucose Oxidase", Biochimica et Biophysica Acta., 1976, vol. 445, pp. 294-308.

Narasimham, K., et al., "p-Benzoquinone Activation of Metal Oxide Electrodes for Attachment of Enzymes", Enzyme and Microbial Technology, 1985, vol. 7, pp. 283-286.

Ohara, T. J., et al., "Glucose Electrodes Based on Cross-Linked $[Os(bpy)_2Cl]^{+/2+}$ Complexed Poly(1-vinylimadazole) Films," Analytical Chemistry, 1993, vol. 65, No. 23, pp. 3512-3516.

Ohara, T. J., et al., "'Wired' Enzyme Electrodes for Amperometric Determination of Glucose or Lactate in the Presence of Interfering Substances", Analytical Chemistry, 1994, vol. 66, No. 15, pp. 2451-2457.

Ohara, T. J., "Osmium Bipyridyl Redox Polymers Used in Enzyme Electrodes", Platinum Metals Review, 1995, vol. 39, No. 2, pp. 54-62.

Olievier, C. N., et al., "In Vivo Measurement of Carbon Dioxide Tension with a Miniature Electrodes", Pflugers Archiv: European Journal of Physiology, 1978, vol. 373, pp. 269-272.

OmniPod Insulet UST400 User Manual, 2011, pp. 1-190.

Opinion of the Court, Supreme Court of the United States, No. 04-1350, *KSR International co.*, Petitioner v. *Teleflex Inc et al.*, Apr. 30, 2007.

Osmonics, Poretics® Polycarbonate Membrane; Product Leaflet; Engineering Purity, 2002, pp. 1-2.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.

Palleschi, G., et al., "A Study of Interferences in Glucose Measurements in Blood by Hydrogen Peroxide Based Glucose Probes", Analytical Biochemistry, 1986, vol. 159, pp. 114-121.

Pankratov, I., et al., "Sol-Gel Derived Renewable-Surface Biosensors", Journal of ElectroAnalytical Chemistry, 1995, vol. 393, pp. 35-41.

Parker, R., et al., "Robust H∞ Glucose Control in Diabetes Using a Physiological Model", AIChE Journal, 2000, vol. 46, No. 12, 2000, pp. 2537-2549.

Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.

Pathak, C., et al., "Rapid Photopolymerization of Immunoprotective Gels in Contact with Cells and Tissue", Journal of the American Chemical Society, 1992, vol. 114, No. 21, pp. 8311-8312.

Patton, S. R., et al., "Continuous Glucose Monitoring Versus Self-monitoring of Blood Glucose in Children with Type 1 Diabetes—Are there Pros and Cons for Both?", US Endocrinol., 2012, vol. 8, No. 1, pp. 27-29.

Pickup, J., "Developing Glucose Sensors for in Vivo Use", Tibtech, 1993, vol. 11, pp. 285-291.

Pickup, J., et al., "Implantable Glucose Sensors: Choosing the Appropriate Sensing Strategy", Biosensors, 1987/88, vol. 3, pp. 335-346.

Pickup, J. C., et al., "In Vivo Molecular Sensing in Diabetes Mellitus: An Implantable Glucose Sensor With Direct Electron Transfer," Diabetologia, 1989, vol. 32, No. 3, pp. 213-217.

Pickup, J., et al., "Potentially-Implantable, Amperometric Glucose Sensors with Mediated Electron Transfer: Improving the Operating Stability", Biosensors, 1989, vol. 4, pp. 109-119.

Pishko, M. V., et al., "Amperometric Glucose Microelectrodes Prepared Through Immobilization of Glucose Oxidase in Redox Hydrogels," Anal. Chem., 1991, vol. 63, No. 20, pp. 2268-2272.

Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", Diabetologia, 1993, vol. 36, pp. 658-663.

Poitout, V., et al., "Calibration in Dogs of a Subcutaneous Miniaturized Glucose Sensor Using a Glucose Meter for Blood Glucose Determination", Biosensors & Bioelectronics, 1992, vol. 7, pp. 587-592.

Poitout, V., et al., "In Vitro and in Vivo Evaluation in Dogs of a Miniaturized Glucose Sensor," ASAIO Transactions, 1991, vol. 37, No. 3 (1 page—Abstract only).

Pollak, A., et al., "Enzyme Immobilization by Condensation Copolymerization into Cross-Linked Polyacrylamide Gels", Journal of the American Chemical Society, 1980, vol. 102, No. 20, pp. 6324-6336.

Quinn, C. P., et al., "Kinetics of Glucose Delivery to Subcutaneous Tissue in Rats Measured with 0.3-mm Amperometric Microsensors", The American Physiological Society, 1995, E155-E161.

Ratner, B. D., "Reducing Capsular Thickness and Enhancing Angeiogenesis Around Implant Drug Release Systems", Journal of Controlled Release, 2002, vol. 78, pp. 211-218.

Reach, G., et al., "Can Continuous Glucose Monitoring Be Used for the Treatment of Diabetes?", Analytical Chemistry, 1992, vol. 64, No. 6, pp. 381-386.

(56) References Cited

OTHER PUBLICATIONS

Rebrin, K., et al., "Automated Feedback Control of Subcutaneous Glucose Concentration in Diabetic Dogs," Diabetologia, 1989, vol. 32, No. 8, pp. 573-576.

Repas, R., "Sensor Sense: RFID for smart position sensing", retrieved from https://www/machinedesign/com/automation-iiot/article/21818777/sensor-sense-rfid-for-smart-position-sensing, 2010, pp. 1-2.

Rodriguez, N., et al., "Flexible Communication and Control Protocol for Injectable Neuromuscular Interfaces", IEEE Transactions on Biomedical Circuits and Systems, 2007, vol. 1, No. 1, pp. 19-27.

Roe, J. N., et al., "Bloodless Glucose Measurements", Critical Review in Therapeutic Drug Carrier Systems, vol. 15, Issue 3, 1998, pp. 199-241.

IPR2022-00605 (Ex. 1024) "Rotor," Dictionary of Mechanical Engineering, Fourth Ed., G.H.F. Nayler, Society of Automotive Engineers, Inc., 1996, p. 328.

IPR2022-00605 (Ex. 1025) "Rotor," Random House Kernerman Webster's College Dictionary, K Dictionaries Ltd. (2010), available at https://www.thefreedictionary.com/rotor.

IPR2022-00605 (Ex. 1026) "Rotate," Random House Kernerman Webster's College Dictionary, K Dictionaries Ltd. (2010), available at https://www.thefreedictionary.com/rotate.

Sakakida, M., et al., "Ferrocene-mediated needle-type glucose sensor covered with newly designed biocompatible membrane," Sensors and Actuators B, 1993, vols. 13-14, pp. 319-322.

Sakakida, M., et al., "Development of ferrocene-mediated needle-type glucose sensor as a measure of true subcutaneous tissue glucose concentrations", Artif Organs Today, 1992, vol. 2, No. 2, pp. 145-458.

Salditt, P., "Trends in Medical Device Design and Manufacturing", SMTA News and Journal of Surface Mount Technology, 2004, vol. 17, pp. 19-24.

Salehi, C., et al., "A Telemetry-Instrumentation System for Long-Term Implantable Glucose and Oxygen Sensors", Analytical Letters, 1996, vol. 29, No. 13, pp. 2289-2308.

Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.

Sandham, W., et al., "Blood Glucose Prediction for Diabetes Therapy Using a Recurrent Artificial Neural Network", 9th European Signal Processing Conference, 1998, Rhodes, Greece, pp. 1-4.

Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.

IPR2022-00605 (Ex. 1013) Scheduling Order in *Abbott Diabetes Care Inc., et al.* v. *Dexcom, Inc.*, 1:21-cv-00977 (D. Del.), dated Dec. 2, 2021.

Scheller, F., et al., "Enzyme Electrodes and Their Application", Philosophical Transactions of the Royal Society of London B, 1987, vol. 316, pp. 85-94.

Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.

Schmidt, F. J., et al., "Calibration of a Wearable Glucose Sensor", The International Journal of Artificial Organs, 1992, vol. 15, No. 1, pp. 55-61.

Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.

Schmidtke, D. W., et al., "Measurement and Modeling of the Transient Difference Between Blood and Subcutaneous Glucose Concentrations in the Rat After Injection of Insulin", Proceedings of the National Academy of Sciences, 1998, vol. 95, pp. 294-299.

Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.

Sharawi, M. S., "Use of low-cost patch antennas in modern wireless technology", IEEE Potentials, 2006, pp. 35-38 and 47.

Shaw, G. W., et al., "In Vitro Testing of a Simply Constructed, Highly Stable Glucose Sensor Suitable for Implantation in Diabetic Patients", Biosensors & Bioelectronics, 1991, vol. 6, pp. 401-406.

Shichiri, M., et al., "Glycaemic Control in Pancreatectomized Dogs with a Wearable Artificial Endocrine Pancreas," Diabetologia, 1983, vol. 24, No. 3, pp. 179-18.

Shichiri, M., et al., "Membrane Design for Extending the Long-Life of an Implantable Glucose Sensor", Diabetes Nutrition and Metabolism, 1989, vol. 2, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device with Needle-type Glucose Sensor: A Useful Tool for Blood Glucose Monitoring in Diabetic Individuals," Diabetes Care, 1986, vol. 9, No. 3, pp. 298-301.

Shichiri, M., et al., "In Vivo Characteristics of Needle-Type Glucose Sensor—Measurement of Subcutaneous Glucose Concentrations in Human Volunteers," Horm Metab Res Suppl. 1988, vol. 20, pp. 17-20.

Shichiri, M., et al., "Wearable Artificial Endocrine Pancreas With Needle-Type Glucose Sensor," The Lancet, 1982, vol. 2, No. 8308, pp. 1129-1131.

Shults, M., "A Telemetry-Instrumentation System for Monitoring Multiple Subcutaneously Implanted Glucose Sensors," IEEE Transactions on Biomedical Engineering, 1994, vol. 41, No. 10, pp. 937-942.

Sittampalam, G., et al., "Surface-Modified Electrochemical Detector for Liquid Chromatography", Analytical Chemistry, 1983, vol. 55, No. 9, pp. 1608-1610.

Soegijoko, S., et al., "External Artificial Pancreas: A New Control Unit Using Microprocessor", Hormone and Metabolic Research Supplement Series, 1982, vol. 12, pp. 165-169.

Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.

Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.

Sternberg, F., et al., "Calibration Problems of Subcutaneous Glucosensors when Applied "In-Situ" in Man", Hormone and Metabolic Research, 1994, vol. 26, pp. 523-526.

Sternberg, R., et al., "Covalent Enzyme Coupling on Cellulose Acetate Membranes for Glucose Sensor Development", Analytical Chemistry, 1988, vol. 60, No. 24, pp. 2781-2786.

Sternberg, R., et al., "Study and Development of Multilayer Needle-type Enzyme-based Glucose Microsensors," Biosensors, 1988, vol. 4, pp. 27-40.

Suekane, M., et al., "Immobilization of Glucose Isomerase", Zettschrift fur Allgemeine Mikrobiologie, 1982, vol. 22, No. 8, pp. 565-576.

Tajima, S., et al., "Simultaneous Determination of Glucose and 1,5-Anydroglucitol", Chemical Abstracts, 1989, vol. 111, No. 25, p. 394.

Tarasevich, M. R., "Bioelectrocatalysis", Comprehensive Treatise of Electrochemistry, 1985, vol. 10, pp. 231-295.

Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.

Taylor, C., et al., ""Wiring" of Glucose Oxidase Within a Hydrogel Made with Polyvinyl Imidazole Complexed with [(Os-4,4'-dimethoxy-2,2'-bipyridine)Cl]$^{+/2+}$", Journal of ElectroAnalytical Chemistry, 1995, vol. 396, pp. 511-515.

Thompson, M., et al., "In Vivo Probes: Problems and Perspectives", Clinical Biochemistry, 1986, vol. 19, pp. 255-261.

(56)           References Cited

OTHER PUBLICATIONS

Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.

Townsend, K., et al., "Getting Started with Bluetooth Low Energy—Chapter 1", 2014, pp. 1-26.

Trojanowicz, M., et al., "Enzyme Entrapped Polypyrrole Modified Electrode for Flow—Injection Determination of Glucose", Biosensors & Bioelectronics, 1990, vol. 5, pp. 149-156.

Tsalikian, e., et al., "Accuracy of the GlucoWatch G2® Biographer and the Continuous Glucose Monintoring System During Hypoglycemia: Experience of the Diabetes Research in Children Network", Diabetes Care, 2004, vol. 27, No. 3, pp. 722-726.

Tung, S., "Layers of Security for Active RFID Tags", RFID Handbook: Applications, Technology, Security, and Privacy, Edited by Ehson, et al., Chapter 33, 2008, pp. 1-28.

Turner, A.P.F., et al., "Diabetes Mellitus: Biosensors for Research and Management", Biosensors, 1985, vol. 1, pp. 85-115.

Turner, R.F.B., et al., "A Biocompatible Enzyme Electrode for Continuous in vivo Glucose Monitoring in Whole Blood", Sensors and Actuators B, 1990, vol. 1, pp. 561-564.

Tuzhi, P., et al., "Constant Potential Pretreatment of Carbon Fiber Electrodes for in Vivo Electrochemistry", Analytical Letters, 1991, vol. 24, No. 6, pp. 935-945.

Umana, M., "Protein-Modified Electrochemically Active Biomaterial Surface", U.S. Army Research Office, Analytical and Chemical Sciences Research Triangle Institute, 1988, pp. 1-9.

United States Court of Appeals for the Federal Circuit, No. 06-1402, *Leapfrog Enterprises, Inc.* v. *Fisher-Price, Inc. and Mattel, Inc.*, May 9, 2007.

Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous In vivo Monitoring, Chapter 4, 1997, pp. 117-137.

Updike, S. J., et al., "A Subcutaneous Glucose Sensor With Improved Longevity, Dynamic Range, and Stability of Calibration", Diabetes Care, 2000, vol. 23, pp. 208-214.

Urban, G., et al., "Miniaturized Thin-Film Biosensors Using Covalently Immobilized Glucose Oxidase", Biosensors & Bioelectronics, 1991, vol. 6, pp. 555-562.

Velho, G., et al., "In Vitro and In Vivo Stability of Electrode Potentials in Needle-Type Glucose Sensors", Diabetes, 1989, vol. 38, No. 2, pp. 164-171.

Velho, G et al., "Strategies for Calibrating a Subcutaneous Glucose Sensor," Biomed. Biochim. Acta, 1989, 48 (11112), pp. 957-964.

Von Woedtke, T., et al., "In Situ Calibration of Implanted Electrochemical Glucose Sensors", Biomedica Biochimica Acta, 1989, vol. 48, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.

Wang, D. L., et al., "Miniaturized Flexible Amperometric Lactate Probe", Analytical Chemistry, 1993, vol. 65, No. 8, pp. 1069-1073.

Wang, J., et al., "Activation of Glassy Carbon Electrodes by Alternating Current Electrochemical Treatment", Analytica Chimica Acta, 1985, vol. 167, pp. 325-334.

Wang, J., et al., "Amperometric Biosensing of Organic Peroxides with Peroxidase-Modified Electrodes", Analytica Chimica Acta, 1991, vol. 254, pp. 81-88.

Wang, J., et al., "Screen-Printable Sol-Gel Enzyme-Containing Carbon Inks", Analytical Chemistry, 1996, vol. 68, No. 15, pp. 2705-2708.

Wang, J., et al., "Sol-Gel-Derived Metal-Dispersed Carbon Composite Amperometric Biosensors", Electroanalysis, 1997, vol. 9, No. 1, pp. 52-55.

Wang, X.H., et al., "Bluetooth: Opening a blue sky for healthcare", Mobile Information Systems, 2006, vol. 2, pp. 151-167.

Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.

Waterhouse, R., "Printed Antennas for Wireless Communications," 2007, pp. 116-129 and 284-289.

Williams, D. L., et al., "Electrochemical-Enzymatic Analysis of Blood Glucose and Lactate", Analytical Chemistry, 1970, vol. 42, No. 1, pp. 118-121.

Wilson, G. S., et al., "Progress Toward the Development of an Implantable Sensor for Glucose," Clinical Chemistry, 1992, vol. 38, No. 9, pp. 1613-1617.

Wong, KL, "Planar Antennas for Wireless Communications," 2003, Chapter 1, Introduction and Overview, pp. 4-17, 38-45, and 218-221.

Yabuki, S., et al., "Electro-Conductive Enzyme Membrane", Journal of the Chemical Society, Chemical Communications, 1989, pp. 945-946.

Yang, L., et al., "Determination of Oxidase Enzyme Substrates Using Cross-Flow Thin-Layer Amperometry", Electroanalysis, 1996, vol. 8, No. 8-9, pp. 716-721.

Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.

Yao, T., "A Chemically-Modified Enzyme Membrane Electrode as an Amperometric Glucose Sensor", Analytica Chimica Acta, 1983, vol. 148, pp. 27-33.

Ye, L. et al., "High Current Density "Wired" Quinoprotein Glucose Dehydrogenase Electroade," Anal. Chem., 1993, vol. 65, No. 3, pp. 238-241.

Yildiz, A., et al., "Evaluation of an Improved Thin-Layer Electrode", Analytical Chemistry, 1968, vol. 40, No. 7, pp. 1018-1024.

Zamzow, K., et al., "New Wearable Continuous Blood Glucose Monitor (BGM) and Artificial Pancreas (AP)", Diabetes, 1990, vol. 39, pp. 5A-20.

Z-Carbon Connector, retrieved from http://www.zaxisconnector.com/SS_zc.shtml, 2004, 2 pages.

Zhang, Y., et al., "Application of Cell Culture Toxicity Tests to the Development of Implantable Biosensors", Biosensors & Bioelectronics, 1991, vol. 6, pp. 653-661.

Zhang, Y., et al., "Elimination of the Acetaminophen Interference in an Implantable Glucose Sensor", Analytical Chemistry, 1994, vol. 66, No. 7, pp. 1183-1188.

Zhu, J., et al., "Fabrication and Characterization of Glucose Sensors Based on a Microarray $H_2O_2$ electrode", Biosensors & Bioelectronics, 1994, vol. 9, pp. 295-300.

Zisser, H. C., "The OmniPod Insulin Management System: the Latest Innovation in Insulin Pump Therapy", Diabetes Ther, 2010, vol. 1, No. 1, pp. 10-24.

Z-Silver Connector, retrieved from http://www.zaxisconnector.com/SS_zs.shtml, 2004, 2 pages.

Certified U.S. Appl. No. 60/424,099, filed Nov. 5, 2002.

De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.

U.S. Appl. No. 10/633,367.

Medtronic MiniMed Sen-Serter® User Guide, 2006, pp. 1-96.

CA, 3,120,335 Examiner's Report, dated Mar. 31, 2023.

CA, 182,961 Examiner's Report, dated Mar. 29, 2023.

CN, 201980082748.1 First Office Action, dated Jan. 10, 2023.

EP, 10739031.2 Response to Response to Response to Grounds of Appeal, dated Jan. 18, 2023.

(56) References Cited

OTHER PUBLICATIONS

EP, 20177703.4 Notice of Intervention, dated Jun. 23, 2023.
EP, 20177703.4 Reply to Opposition, Feb. 22, 2023.
EP, 20177712.5 Notice of Intervention, dated Jun. 23, 2023.
EP, 20177712.5 Reply to Opposition, May 23, 2023.
EP, 20177712.5 Grounds of Opposition Gulde & Partner Patent, Dec. 22, 2022.
EP, 20177712.5 Grounds of Opposition Dexcom, Dec. 22, 2022.
EP, 20177712.5 Notice of Opposition Gulde & Partner Patent, Dec. 22, 2022.
EP, 20177712.5 Notice of Opposition Dexcom, Dec. 22, 2022.
EP, 20195922.8 Reply to Opposition, Jun. 20, 2023.
EP, 20195922.8 Notice of Intervention, dated Jun. 13, 2023.
EP, 20195922.8 Grounds of Opposition Dexcom, Jan. 26, 2023.
EP, 20195922.8 Notice of Opposition Dexcom, Jan. 26, 2023.
JP, 2021-531135 Office Action, dated Feb. 22, 2023.
WO, PCT/US2012/062551 ISR and Written Opinion, dated Jan. 2, 2013.
WO, PCT/US2023/010054 ISR and Written Opinion, dated May 15, 2023.
WO, PCT/US2023/010054 Invitation to Pay Additional Fees, dated Mar. 24, 2023.
"Abbott Receives CE Mark for Freestyle® Libre, A Revolutionary Glucose Monitoring System for People With Diabetes", 2014, 7 pages.
"Alcove", Webster's New College Dictionary, 2001, p. 26.
Anderson, A. J., "Foundations of Computer Technology", 1994, pp. 55-57.
Boise, M., "Dexcom CEO Kevin Sayer Explains G6", 2018, retrieved from https://beyondtype1.org/dexcom-ceo-kevin-sayer-explains-g6/, 9 pages.
Certified True Copy of Preliminary Amendment filed on Apr. 20, 2018 for U.S. Pat. No. 10,827,954, 7 pages.
Certified True Copy of Excerpts of the File History of U.S. Pat. No. 10,973,443, 22 pages.
CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.
"Deciding When to Submit a 510(k) for a Change to an Existing Device, Guidance for Industry and Food and Drug Administration Staff", 2017, pp. 1-77.
"Deciding When to Submit a 510(k) for a Software Change to an Existing Device, Guidance for Industry and Food and Drug Administration Staff", 2017, pp. 1-31.
Dexcom CEO—Prime Position in Our Market—Mad Money—CNBC.mp4, Transcript 2023 by Sonix, 2 pages.
DexCom (DXCM) 2017 Q4 Earnings Call Transcript, 2017, retrieved from https://docoh.com/transcript/1093557/2017Q4/DXCM, 11 pages.
DexCom (DXCM) Q1 2018 Results—Earnings Call Transcript, 2018, retrieved from https://seekingalpha.com/article/4168949-dexcom-dxcm-q1-2018-results-earnings-call-transcript, 4 pages.
Dexcom, Inc. NasdaqGS:DXCM Company Conference Presentation, 2019, 10 pages.
Dexcom, Inc. NasdaqGS:DXCM Company Conference Presentation, 2020, 9 pages.
Dexcom, Inc. NasdaqGS:DXCM Company Conference Presentation, 2021, 16 pages.
Dexcom G6 Continuous Glucose Monitoring System User Guide, pp. 1-22.
Dexcom G6 Start Here Set up Guide, pp. 1-8.
Dexcom G6 Using Your G6 Guide, Mar. 2020, pp. 1-7.
Dexcom Seven® Plus Continuous Glucose Monitoring System User's Guide, 2011, pp. 1-144.
DexCom™ STS™ Continuous Glucose Monitoring System FDA Premarket Approval (PMA), 2006, pp. 1-7.
DexCom™ STS™ Continuous Glucose Monitoring System Summary of Safety and Effectiveness Data, 2006, 20 pages.
DexCom™ STS™ Sensor Instructions for Use, 2006, pp. 1-6.

Dexcom STS-7 Continuous Glucose Monitoring System FDA Premarket Approval (PMA), 2007, pp. 1-7.
Dexcom STS®-7 Continuous Glucose Monitoring System Summary of Safety and Effectiveness Data, 2007, 14 pages.
Dexcom STS®-7 Continuous Glucose Monitoring System User's Guide, 2007, pp. 1-74.
Diglas, J., et al., "Reduced pain perception with Pen Mate™, an automatic needle insertion device for use with an insulin pen", Practical Diabetes International, 1999, vol. 16, No. 2, pp. 39-41.
"Does Dexcom Really Have a Future If It Can't Match Abbott's Scale", 2019, retrieved from https://www.sprucepointcap.com/reports/dxcm_research_thesis_3-21-2019.pdf, p. 46.
Email chain from Sophie Hood, oldest email dated Jan. 24, 2023, 5 pages.
European Standard, ISO 11607-1, Packaging for terminally sterilized medical devices—Part 1: Requirements for materials, sterile barrier systems and packaging systems, 2006, 32 pages.
European Standard, ISO 13485, Medical devices—Quality management systems—Requirement for regulatory purposes, 2003, 69 pages.
European Standard, ISO 15197, In vitro diagnostic test systems - Requirements for blood glucose monitoring systems for self-testing in managing diabetes mellitus, 2003, 43 pages.
Explore The Monroe Street Market Community, Retrieved from https://www.monroestreetmarket.com/floor-plans/apartment/B-231, 2 pages.
"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
Food and Drug Administration, HHS, 2009, Code of Federal Regulation § 820.30, Subpart C—Design Controls, pp. 147-148.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
FreeStyle Navigator Continuous Glucose Monitoring System FDA Premarket Approval (PMA), 2008, pp. 1-7.
Hemmerich, K. J., et al., "Sterilization Methods Stand the Test of Time", 2004, retrieved from https://www.mddionline.com/sterilization/sterilization-methods-stand-test-time, pp. 1-8.
Hirsch, I. B., "Realistic Expectations and Practical Use of Continuous Glucose Monitoring for the Endocrinologist", The Journal of Clinical Endocrinology & Metabolism, 2009, VI. 94, No. 7, pp. 2232-2238.
Hoss, U., et al., "Continuous glucose monitoring in the tissue: Do we really need to calibrate in-vivo?", pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Hughes, M. D., "The Business of Self-Monitoring of Blood Glucose: A Market Profile", Journal of Diabetes Science and Technology, 2009, vol. 3, No. 5, pp. 1219-1223.
IEEE 100 The Authoritative Dictionary of IEEE Standards Terms, Seventh Edition, 2000, 3 pages.
International Standard, ISO 14971, Medical devices—Application of risk management to medical devices, 2007, 90 pages.
"An Interview with Kevin Sayer, President and CEO of Dexcom, About The New G6", 2021, 5 pages.
Kal, S., "Basic Electronics—Devices, Circuits and IT Fundamentals", 2006, Chapter 13, Microcomputers and Microprocessors, p. 412.

(56) References Cited

OTHER PUBLICATIONS

Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.
Medtronic Guardian® Real-Time Continuous Glucose Monitoring System User Guide, 2006, pp. 1-181.
Medtronic MiniMed Guardian RT FDA Premarket Approval (PMA), 2005, pp. 1-6.
Medtronic MiniMed Guardian RT Summary of Safety and Effectiveness Data, 2005, 13 pages.
Medtronic MiniMed Paradigm® REAL-Time 522 and 722 Insulin Pumps User Guide, 2008, pp. 1-262.
Occupational Safety and Health Admin., Labor, 2003, 29 CFR § 1910.1030 Bloodborne pathogens, pp. 260-273.
Omnipod image, Exhibit 182 of ADC Reply Brief SJ, Daubert, Sep. 22, 2022, 2 pages.
One Touch® Ultra™ Blood Glucose Monitoring System Owner's Booklet, 2000, 23 pages.
OneTouch Ultra2 Blood Glucose Monitoring System Owner's Booklet, 2005, 34 pages.
Order, Federal Communications Commission, 2006, pp. 1-8.
Program, 2nd International Conference on Advanced Technologies & Treatments for Diabetes, Athens, Greece, 2009, 3 pages.
"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
"Submission and Review of Sterility Information in Premarket Notification (510(k)) Submissions for Devices Labeled as Sterile, Guidance for Industry and Food and Drug Administration Staff", 2016, pp. 1-11.
Tegnestedt, C., et al., "Levels and sources of sound in the intensive care unit—an observational study of three room types", Acta Anaesthiesiologica Scandinavica, 2013, pp. 1-10.
Watkin, J., "An Introduction to Flash Glucose Monitoring", 14 pages.
CN 201980082748.1 Second Office Action Jul. 10, 2023.
EP 20177703.4 Reply to Reply to Notice of Opposition Jun. 29, 2023.
EP 20177712.5 Reply to Reply to Notice of Opposition Dexcom Sep. 27, 2023.
EP 20177712.5 Reply to Reply to Notice of Opposition Gulde & Partner Patent Aug. 30, 2023.
EP 20195922.8 Summons to Attend Oral Proceedings Sep. 21, 2023.
EP 20195922.8 Reply to Notice of Intervention Aug. 29, 2023.
EP 20195922.8 Reply to Reply to Notice of Opposition Aug. 21, 2023.
JP 2021-531135 Office Action Aug. 9, 2023.
MY PI2022007295 Examination Report Jul. 11, 2023.
US Petition For Inter Partes Review Of U.S. Pat. No. 11,202,591, IPR No. 2023-01409 Oct. 11, 2023.
US Petition For Inter Partes Review Of U.S. Pat. No. 11,266,335, IPR No. 2023-01397 Oct. 6, 2023.
US Petition For Inter Partes Review Of U.S. Pat. No. 11,266,335, IPR No. 2023-01396 Oct. 6, 2023.
US Final Written Decision, IPR No. 2022-00605 Jul. 10, 2023.
US Petitioner's Reply to Patent Owner's Response to Petition, IPR No. 2022-00605 Jan. 11, 2023.
US Supplemental Declaration of Gary D. Fletcher, Ph.D, IPR No. 2022-00605 Jan. 11, 2023.

Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.
Dexcom G6 Continuous Glucose Monitoring System User Guide, 2019, pp. 1-27.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Email from John Shaw of Shaw & Keller dated May 16, 2023, 2 pages.
Panteleon, A. E., et al., "The Role of the Independent Variable to Glucose Sensor Calibration", Diabetes Technology & Therapeutics, 2003, vol. 5, No. 3, pp. 401-410.
Parker, S. P., ed., McGraw-Hill Dictionary of Mechanical and Design Engineering, 1984 (excerpted), pp. 1-4.
Shenoi, B. A., ed., Introduction to Digital Signal Processing and Filter Design, 2006, "Introduction", Chapter 1, pp. 1-30.
Smith, S. S., ed., The Scientist and Engineer's Guide to Digital Signal Processing, Second Edition, 1997-1999, "Digital Signal Processors", Chapter 28, pp. 503-534.
CA 2,617,192 Examiner's Report Oct. 22, 2012.
CA 2,984,939 Examiner's Report Nov. 15, 2023.
CA 3,182,961 Examiner's Report Nov. 15, 2023.
CN 200780039416.2 Second Office Action, Apr. 25, 2012.
CN 200780039416.2 First Office Action Mar. 30, 2011.
CN 200880005388.7 Second Office Action May 16, 2012.
CN 200880005388.7 First Office Action Jul. 25, 2011.
CN 201980082748.1 Final Office Action, Nov. 27, 2023.
EP 06788869.3 Examination Report Sep. 25, 2012.
EP 06788869.3 Extended Search Report Mar. 18, 2010.
EP 06813967.4 Extended Search Report Mar. 4, 2010.
EP 07854298.2 Extended Search Report Mar. 29, 2010.
EP 08730066.1 Extended Search Report Oct. 5, 2012.
EP 18741791.0 Examination Report Dec. 15, 2023.
EP 20177703.4 Reply to Reply to Reply to Notice of Opposition ADC Dec. 18, 2023.
EP 20177703.4 Reply to Notice of Intervention Nov. 17, 2023.
EP 20177712.5 Reply to Reply to Reply to Notice of Opposition ADC Dec. 18, 2023.
EP 20177712.5 Reply to Notice of Intervention, Nov. 17, 2023.
EP 20195922.8 Response to Summons to Attend Oral Proceedings Feb. 15, 2024.
EP 20195922.8 Written Submissions Dexcom, Dec. 12, 2023.
EP 20195922.8 Written Submissions ADC Oct. 23, 2023.
EP 23166498.8 Extedned Search Report Nov. 17, 2023.
EP 23190032.5 Extended Search Report Nov. 17, 2023.
JP 2009-534799 Final Office Action Feb. 19, 2013.
JP 2009-534799 Office Action Sep. 27, 2011.
MX MX/a/2009/004322 Office Action Mar. 11, 2013.
MX MX/a/2009/004322 Office Action Sep. 19, 2012.
MY PI202302023005466 Examination Report Dec. 28, 2023.
RU 2009135048 Office Action Dec. 20, 2011.
RU 2009119430 Office Action Jun. 5, 2011.
Third Declaration of Gary Fletcher, Ph.D., IPR No. 2024-00520 Jan. 31, 2024.
Petition for Inter Partes Review of U.S. Pat. No. 11,266,335, IPR No. 2024-00520.
Petitioner's Explanation of Material Differneces Between Petitions, IPR No. 2023-01397 Oct. 6, 2023.
Declaration of Gary D. Fletcher, Ph. D, IPR No. 2023-01396 and IPR No. 2023-01397, Oct. 6, 2023.
Petitioner's Explanation of Material Differences Between Petitions, IPR No. 2023-01396, Oct. 6, 2023.
Notice of Fnal Written Decision re Inter Partes Review of the '649 Patent, IPR No. 2022-00604 Jul. 13, 2023.
Record of Oral Hearing, IPR No. 2022-00605 Apr. 26, 2023.
Second Declaration by Dr. Michael Cima in Support of Patent Owner's Response, IPR No. 2022-00605 Oct. 19, 2022.
Patent Owner's Response, IPR No. 2022-00605, Oct. 19, 2022.
Reexamination U.S. Appl. No. 90/019,331 Order Granting Request for Reexamination of U.S. Pat. No. 11,013,440 Jan. 23, 2024.

(56)                References Cited

OTHER PUBLICATIONS

Request for Ex Parte Reexamination Under 35.U.S.C. §§ 302-307 and 37 C.F.R. § 1.510 of U.S. Pat. No. Dec. 11, 2023.
US Request for Ex Parte Reexamination Under 35.U.S.C. §§ 302-307 and 37 C.F.R. § 1.510 of U.S. Pat. No. 11,000,216.
US Reexamination U.S. Appl. No. 90/019,307 Order Granting Request for Reexamination of U.S. Pat. No. 10,973,443.
US Request for Ex Parte Reexamination Under 35.U.S.C. §§ 302-307 and 37 C.F.R. § 1.510 of U.S. Pat. No. 10,973,443.
US Request for Ex Parte Reexamination Under 35.U.S.C. §§ 302-307 and 37 C.F.R. § 1.510 of U.S. Pat. No. 10,959,654.
WO PCT/US2006/029541 ISR and Written Opinion Apr. 24, 2007.
WO PCT/US2006/033885 ISR and Written Opinion Aug. 3, 2007.
WO PCT/US2007/082121 ISR and Written Opinion May 9, 2008.
WO PCT/US2008/054186 ISR and Written Opinion Aug. 8, 2008.
WO PCT/US2008/065154 ISR and Written Opinion Sep. 3, 2008.
WO PCT/US2010/047065 ISR and Written Opinion Dec. 21, 2010.
WO PCT/US2010/047414 ISR and Written Opinion Dec. 27, 2010.
WO PCT/US2010/047415 ISR and Written Opinion Oct. 25, 2010.
CA 3,120,335 Examiner's Report May 27, 2024.
EP 10739031.2 Decision of Oral Proceedings Jun. 11, 2024.
EP 10739031.2 Minutes of Oral Proceedings May 10, 2024.
EP 10739031.2 Communication from Board of Appeals Feb. 21, 2024.
EP 10739031.2 Summons to Attend Oral Proceedings Oct. 26, 2023.
EP 20177703.4 Summons to Attend Oral Proceedings Apr. 29, 2024.
EP 20177712.5 Response to Written Submissions Dexcom Feb. 26, 2024.
EP 20177712.5 Written Submissions ADC Jan. 26, 2024.
EP 20195922.8 Written Submissions Dexcom May 9, 2024.
EP 20195922.8 Decision Revoking the European Patent May 8, 2024.
EP 20195922.8 Minutes of the Oral Proceedings May 8, 2024.
EP 20195922.8 Written Submissions Dexcom Mar. 15, 2024.
EP 21211041.5 Grounds of Opposition Dexcom Mar. 28, 2024.
EP 21211041.5 Notice of Opposition Dexcom Mar. 28, 2024.
EP 24152079.0 Partial Search Report Jun. 14, 2024.
Patent Owner's Exhibit List, IPR2024-00520 Mar. 23, 2024.
Telephonic Hearing, IPR2024-00520 Mar. 13, 2024.
Petitioner's Explanation of Material Differences Between the Petition in IPR2024-00520 and Previously Filed Petitions in IPR2023-01396 and IPR2023-01397, IPR No. 2024-00520 Jan. 31, 2024.
Patent Owner's Preliminary Response, IPR No. 2023-01409 Jan. 18, 2024.
Notice of Filing Date Accorded to Petition and Time for Filing Patent Owner Preliminary Response, IPR No. 2023-01409, Jan. 18, 2024.
Patent Owner's Updated Exhibit List, IPR2023-01397 Mar. 25, 2024.
Telephonic Hearing, IPR2023-01397 Mar. 13, 2024.
Patent Owner's Preliminary Response, IPR No. 2023-01397 Jan. 18, 2024.
Patent Owner's Response to Petitioner's Explanation of Material Differences Between Petitions, IPR Nos. 2023-01396 and 2023-01397 Jan. 18, 2024.
Telephonic Hearing, IPR2023-01396 Mar. 13, 2024.
Petitioner's Updated Mandatory Notices Pursuant to 37 C.F.R. § 42.8(a)(3), IPR No. 2023-01396 Feb. 19. 2024.
Patent Owner's Preliminary Response, IPR No. 2023-01396 Jan. 18, 2024.
Notice of Filing Date Accorded to Petition and Time for Filing Patent Owner Preliminary Response, IPR No. 2023-01396 Oct. 18, 2023.
Reexamination U.S. Appl. No. 90/019,329 Order Granting Request for Reexamination of U.S. Pat. No. 11,013,440 Jan. 30, 2024.
Reexamination U.S. Appl. No. 90/019,331 Declaration of Gary D. Fletcher, Ph.D. Dec. 11, 2023.
Reexamination U.S. Appl. No. 90/019,331 Order Granting Request for Reexamination of U.S. Pat. No. 11,000,216 Jan. 23, 2024.
Reexamination U.S. Appl. No. 90/019,330 Order Granting Request for Reexamination of U.S. Pat. No. 10,959,654, Jan. 23, 2024.
Reexamination U.S. Appl. No. 90/019,330 Declaration of John Mastrototaro, Ph.D. Dec. 11, 2023.
WO PCT/US24/11756 Invitation to Pay Additional Fees May 7, 2024.
WO PCT/US24/16127 Invitation to Pay Additional Fees Jun. 4, 2024.
Continuous Glucose Monitoring Systems Product Reference Guide, Diabetes Health, 2006- 2007, pp. 50-51.
Das, S. D., et al., "Review—Electrochemistry and Other Emerging Technologies for Continuous Glucose Monitoring Devices", ECS Sensors Plus, 2022, 19 pages.
Dexcom G6 Continuous Glucose Monitoring System User Guide, 2022, 346 pages.
Englert, K., et al., "Skin and Adhesive Issues With Continuous Glucose Monitors: A Sticky Situation", Journal of Diabetes Science and Technology, 2014, vol. 8, No. 4, pp. 745-751.
U.S. Appl. No. 61/317,243.
U.S. Appl. No. 61/345,562.
U.S. Appl. No. 61/361,374.
U.S. Appl. No. 61/411,262.
Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.
Freestyle Libre Brochure, 2016, 10 pages.
Freestyle Libre Fact Sheet, 2016, retrieved from www.FreeStyleLibre.de, 2 pages.
Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.
Hovorka, R., "Continuous glucose monitoring and closed-loop systems", Diabetic Medicine, 2005, vol. 23, pp. 1-12.
Medtronic MiniMed iPro2 User Guide, 2010, pp. 1-99.
Nichols, S. P., et al., "Biocompatible Materials for Continuous Glucose Monitoring Devices", Chem Rev., 2013, vol. 113, No. 4, pp. 2528-2549.
Rice, M. J., et al., "Continuous Measurement of Glucose: Facts and Challenges", Anesthesiology, 2012, vol. 116, No. 1, pp. 199-204.
Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.
Rocchitta, G., et al., "Enzyme Biosensors for Biomedical Applications: Strategies for Safeguarding Analytical Performances in Biological Fields", Sensors, 2016. vol. 16, No. 6, 21 pages.
"Transcutaneous", Webster's Third New International Dictionary, 2002, pp. 2426.
Xu, J., et al., "Anti-Biofouling Strategies for Long-Term Continuous Use of Implantable Sensors", Chemosensors, 2020, vol. 20 No. 3, 29 pages.
CA 2,984,939 Examiner's Report Aug. 7, 2024.
CN 200880005149.1 Notice of Allowance Jun. 21, 2013.
CN 200880005149.1 Fourth Office Action Dec. 3, 2012.
CN 200880005149.1 Third Office Action Feb. 16, 2012.
CN 200880005149.1 Second Office Action Aug. 17, 2011.
CN 200880005149.1 First Office Action Jul. 29, 2010.
DE Complaint in Litigation of EP 3300658 Mar. 20, 2024.
EP 17182379.2 Grounds of Opposition Jul. 12, 2024.
EP 17182379.2 Notice of Opposition Jul. 12, 2024.
EP 17182379.2 Reply to Examination Report Apr. 9, 2021.
EP 17182379.2 Reply to Search Report Oct. 3, 2018.
EP 20177712.5 Summons to Attend Oral Proceedings Oct. 1, 2024.
EP 20177712.5 Response to Summons to Attend Oral Proceedings Aug. 30, 2024.
EP 20177712.5 Summons to Attend Oral Proceedings Jul. 2, 2024.
EP 20195922.8 Grounds of Appeal Sep. 6, 2024.
EP 20195922.8 Notice of Appeal Jul. 4, 2024.
EP 21211041.5 Summons to Attend Oral Proceedings Sep. 23, 2024.
EP 21211041.5 Reply to Notice of Opposition Jul. 17, 2024.
EP 23166498.8 Examination Report, Sep. 2, 2024.
EP 24152079.0 Extended Search Report, Sep. 4, 2024.

(56)                References Cited

OTHER PUBLICATIONS

EP 24187206.8 Extended Search Report, Oct. 9, 2024.
GB Claim No. HP-2021-000025 Approved Judgement, Oct. 18, 2023.
MX MX/a/2021/007294 Office Action, Aug. 20, 2024.
RU 2009134334 Office Action, Feb. 7, 2012.
UP First Expert Opinion of Dr Michael Schoemaker of Litigation of EP 3977921, Jun. 11, 2024.
US Notice of Filing Date Accorded to Petition and Time for Filing Patent Owner Preliminary Response, IPR No. 2024-00860. May 23, 2024.
US Declaration of Dr. Cameron Riviere, Ph.D., IPR No. 2024-00860, May 9, 2024.
US Petition For Inter Partes Review Of U.S. Pat. No. 11,510,625, IPR No. 2024-00860, May 9, 2024.
US Decision Denying Institution of Inter Partes Review, IPR No. 2024-00520, Aug. 8, 2024.
US Patent Owner's Authorized Sur-Reply to Petitioner's Reply to Patent Owner's Preliminary Response, IPR No. 2024-00520, Jun., 11, 2024.
US Petitioner's Authorized Reply to Patent Owner's Preliminary Response, IPR No. 2024-00520, May 31, 2024.
US Patent Owner's Preliminary Response, IPR No. 2024-00520, May 8, 2024.
US Order, IPR No. 2023-01409, May 30, 2024.
US Notice of Stipulation, IPR No. 2023-01409, May 29, 2024.
US Patent Owner's Objections to Petitioner's Exhibits to the Petition, IPR No. 2023-01409, Apr. 29, 2024.
US Patent Owner's Request for Rehearing by the Director, IPR 2023-01409, Apr. 29, 2024.
US Email of Peter McAndrews, IPR 2023-01409. Apr. 29, 2024.
US Decision Granting Institution of Inter Partes Review, IPR No. 2023-01409, Apr. 29, 2024.
US Scheduling Order, IPR 2023-01409, Apr. 15, 2024.
US Order Conduct of the Proceeding 37 C.F.R. § 42.5, IPR No. 2023-01409.
Petitioner's Updated Exhibit List, IPR No. 2023-01409, Feb. 5, 2024.
Telephonic Conference Call, IPR No. 2023-01409, Feb. 2, 2025.
Patent Owner's Updated Mandatory Notices, IPR No. 2023-01409, Feb. 2, 2024.
Email of Andrew M. Mason, IPR 2023-01409, Jan. 30, 2024.
Decision Denying Institution of Inter Partes Review, IPR No. 2023-01397, Apr. 16, 2024.
Petitioner's Updated Mandatory Notices Pursuant to 37 C.F.R. § 42.8(a)(3), IPR No. 2023-01397, Feb. 19, 2024.
Patent Owner's Updated Mandatory Notices, IPR No. 2023-01397, Feb. 2, 2024.
Petitioner's Request for Rehearing of Decision Denying Institution, IPR No. 2023-01396, May 16, 2024.
Decision Denying Institution of Inter Partes Review, IPR No. 2023-01396, Apr. 16, 2024.
Patent Owner's Updated Exhibit List, IPR No. 2023-01396, Mar. 25, 2024.
Reexamination No. U.S. Appl. No. 90/019,307 Petition Under 37 CFR § 1.181 to Terminate, Aug. 15, 2024.
Reexamination No. U.S. Appl. No. 90/019,307 Decision on Petitions, Aug. 7, 2024.
Reexamination No. U.S. Appl. No. 90/019,307 Petition Under 37 CFR § 1.59 to Expunge Application Papers, Aug. 1, 2024.
Reexamination No. U.S. Appl. No. 90/019,307 Petition Under 37 CFR § 1.59 to Expunge Application Papers. Jun. 12, 2024.
Reexamination U.S. Appl. No. 90/019,307 Notification of Concurrent Proceedings, May 15, 2024.
Reexamination No. U.S. Appl. No. 90/019,307 Petition Under 37 CFR §§ 1.182 and/or § 1.183 to Allow Filing and Consideration of Response to Patent Owner's Extraordinary Petition to Suspend, Mar. 19, 2024.
Reexamination No. U.S. Appl. No. 90/019,307 Petition Under 37 CFR § 1.181 and/or § 1.183 to Suspend, Mar. 1, 2024.

Reexamination U.S. Appl. No. 90/019,329 Notice of Intent to Issue Ex Parte Reexamination Certificate.
Reexamination U.S. Appl. No. 90/019,329 Decision on Petition Under 37 C.F.R. § 1.59, Sep. 16, 2024.
Reexamination U.S. Appl. No. 90/019,329 Statutory disclaimer per Manual of Patent Examining Procedure (MPEP) 1490, Sep. 3, 2024.
Reexamination U.S. Appl. No. 90/019,329 Petition Under 37 C.F.R. § 1.182 to Seal Document Versions Filed via IDS and Substitute Redacted Document Versions Therfor, Aug. 1, 2024.
Reexamination No. U.S. Appl. No. 90/019,329 Petition Under 37 CFR § 1.59 to Expunge Application Papers, Jul. 25, 2024.
Reexamination No. U.S. Appl. No. 90/019,329 Ex Parte Reexamination Interview Summary, Jul. 25, 2024.
Reexamination U.S. Appl. No. 90/019,329 Decision on Petition Under 37 C.F.R. § 1.59, Jul. 22, 2024.
Reexamination No. U.S. Appl. No. 90/019,329 Decision Sua Sponte Vacating Notice of Intent to Issue Ex Parte Reexamination Certificate, Jul. 3, 2024.
Reexamination No. U.S. Appl. No. 90/019,329 Petition Under 37 CFR § 1.59 to Expunge Application Papers, Jun. 12, 2024.
Reexamination U.S. Appl. No. 90/019,329 Notification of Concurrent Proceedings, May 15, 2024.
Petition Under 37 CFR § 1.181 and/or § 1.182 to Terminate Reexamination No. U.S. Appl. No. 90/019,329. Apr. 26, 2024.
Reexamination U.S. Appl. No. 90/019,330 Notice of Intent to Issue Ex Parte Reexamination Certificate, Oct. 7, 2024.
Reexamination U.S. Appl. No. 90/019,330 Decision on Petition Under 37 C.F.R. § 1.59. Sep. 16, 2024.
Reexamination U.S. Appl. No. 90/019,330 Decision Granting Petition and Vacating a Reexamination Certificate, Aug. 26, 2024.
Ex Parte Reexamination Certificate of U.S. Pat. No. 10,959,654, Aug. 5, 2024.
Reexamination U.S. Appl. No. 90/019,330 Petition Under 37 C.F.R. § 1.182 to Seal Document Versions Filed via IDS and Substitute Redacted Document Versions Therfor, Aug. 1, 2024.
Reexamination No. U.S. Appl. No. 90/019,330 Petition Under 37 CFR § 1.59 to Expunge Application Papers, Aug. 1, 2024.
Reexamination U.S. Appl. No. 90/019,330 Petition to Withdraw From Issue and Reopen the Proceeding Jul. 26, 2024.
Reexamination U.S. Appl. No. 90/019,330 Decision on Petition Under 37 C.F.R. § 1.59 Jul. 16, 2024.
Reexamination U.S. Appl. No. 90/019,330 Notice of Intent to Issue Ex Parte Reexamination Certificate of U.S. Pat. No. 10,959,654 Jul. 1, 2024.
Reexamination No. U.S. Appl. No. 90/019,330 Petition Under 37 CFR § 1.59 to Expunge Application Papers Jun. 12, 2024.
Reexamination U.S. Appl. No. 90/019,330 Notification of Concurrent Proceedings May 15, 2024.
Reexamination U.S. Appl. No. 90/019,331 Decision on Petition Under 37 C.F.R. § 1.59 Sep. 16, 2024.
Reexamination U.S. Appl. No. 90/019,331 Decision Granting Petition Aug. 26, 2024.
Reexamination U.S. Appl. No. 90/019,331 Petition Under 37 C.F.R. § 1.182 to Seal Document Versions Filed via IDS and Substitute Redacted Document Versions Therfor Aug. 1, 2024.
Reexamination No. U.S. Appl. No. 90/019,331 Petition Under 37 CFR § 1.59 to Expunge Application Papers Aug. 1, 2024.
Reexamination U.S. Appl. No. 90/019,331 Petition to Withdraw From Issue and Reopen the Proceeding Jul. 26, 2024.
Reexamination U.S. Appl. No. 90/019,331 Decision on Petition Under 37 C.F.R. § 1.59 Jul. 16, 2024.
Reexamination U.S. Appl. No. 90/019,331 Notice of Intent to Issue Ex Parte Reexamination Certificate Jul. 10, 2024.
Reexamination U.S. Appl. No. 90/019,331 Notification of Concurrent Proceedings May 15, 2024.
WO PCT/US2008/054165 ISR and Written Opinion Jun. 5, 2008.
WO PCT/US2008/067791 ISR and Written Opinion Sep. 30, 2008.
WO PCT/US24/11756 ISR and Written Opinion Jun. 28, 2024.
WO PCT/US24/16127 ISR and Written Opinion Sep. 11, 2024.
WO PCT/US24/18665 ISR and Written Opinion Jun. 21, 2024.
"27 Winners Announced at the 19[th]Annual Medical Design Excellence Awards (MDEA) Award Ceremony", UBM Americas, 2017, 4 pages.

(56)          References Cited

OTHER PUBLICATIONS

"55 Chosen as Winners in Annual BIG Innovation Awards", 2018, retrieved from https://www.bintelligence.com/posts/55-chosen-as-winners-in-annual-big-innovation-awards, 2 pages.

2017 Good Design Award, retrieved from https://www.g-mark.org/gallery/winners/9dda01a3-803d-11ed-af7e-0242ac130002, 9 pages.

"2019 Top 10 Innovations", The Scientist, retrieved from https://www.the-scientist.com/2019-top-10-innovations-66738, 7 pages.

Abbott 2023 Annual Report, retrieved from https://www.abbottinvestor.com/static-files/6cb09c09-2422-40e0-a24b-6545ffcf5267, pp. 1-82.

Abbott Clinical Trials Competitor and Ecosystem Players, 2020, 28 pages.

"Abbott's Freestyle Libre® Is Named Best Medical Technology In Last 50 Years By The Galien Foundation", 2022, PRNewswire, 1 page.

"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards# :~:text=FDA%20clears%20Abbott's%20FreeStyle%20Libre,high%20or%20low%20without%20scanning, on Jul. 7, 2024, 3 pages.

"Abbott's Freestyle Libre® 3 Receives U.S. FDA Clearance—Features World's Smallest, Thinnest and Most Accurate 14-Day Glucose Sensor", 2022, PRNewswire, 3 pages.

"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.

"Abbott's Freestyle® Libre 14 Day Flash Glucose Monitoring System Now Approved in U.S.", 2018, PRNewswire, 2 pages.

About the Edison Awards retrieved from https://edisonawards.com/about/, 2024, 3 pages.

Ahn, D., "Abbott's Euro approved wearable glucose monitor is different than anything on the market", 2014, retrieved from https://www.imedicalapps.com/2014/09/abbotts-wearable-glucose-monitor/, 6 pages.

"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.

Blum, A., "Freestyle Libre Glucose Monitoring System", Clinical Pharmacology Update, 2018, vol. 36, No. 2, pp. 203-204.

Cather, D. E., "Cgm Frustrations Survey", 2020, 36 pages.

Certified U.S. Appl. No. 61/149,639, filed Feb. 3, 2009.

CES 2022 Innovation Award Honorees, retrieved from https://www.ces.tech/innovation-awards/honorees/2022/best-of/f/freestyle-libre-3-system.aspx, 1 page.

2019 Chicago Innovation Award Winner Abbott Laboratories, retrieved from https://chicagoinnovation.com/winners/abbott-laboratories/, 4 pages.

Design Concepts Project Status Update, Glucose Sensor Applicator Dexcom (project #2554), 2014, 5 pages.

Dexcom G5 Quick Start Guide, 2020, pp. 1-31.

Dexcom G6 Start Here Set up Guide, 2022, pp. 18 pages

Dexcom G6 Continuous Glucose Monitoring (CGM) System Section 510(k) Approval, 2022, 7 pages.

"The Dexcom G7. The most accurate CGM system.1" retrieved from https://www.dexcom.com/g7-cgm-system on Jun. 27, 2024, 20 pages.

Dexcom G7 Continuous Glucose Monitoring (CGM) System Section 510(k) Approval, 2022, 10 pages.

Dexcom G7 User Guide, 2024, p. i-186.

Edison Awards Announces 2016 Gold, Silver, and Bronze Awards Winners, Edison Awards, 9 pages.

Edison Best New Product Awards™ 2021 Winners retrieved from https://edisonawards.com/2021-winners/, 19 pages.

Edison Best New Product Awards™ 2022 Winners retrieved from https://edisonawards.com/2022-winners/, 52 pages.

Email from Christopher M Dougherty dated Dec. 17, 2019, 68 pages.

U.S. Appl. No. 62/524,247.

Freestyle Libre FAQ, 2024, retrieved from https://www.freestyle.abbott/uk-en/support/faq/question-answer.html?q=UKFaqquestion-55#, 2 pages.

"FreeStyle Libre Honored by Prix Galien", 2019, 4 pages.

FreeStyle Libre In-Service Guide, 2021, 28 pages.

FreeStyle Libre 2 Get Started Guide, 2023, pp. 1-28.

Freestyle Libre 2 HCP Pulse Report, 2021, 13 pages.

"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/# :~:text=Beschreibung%20Die%20kontinuierliche%20Glukosemessung%20mit, um%20di e%20Glukosewerte%20kontinuierlich%20aufzuzeichnen, 1 page.

FreeStyle Libre 3 Get Started Guide, 2023, pp. 1-20.

FreeStyle Libre 3 User's Manual, 2022-2023, pp. iv-241.

The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.

Gough, D. A., et al., "Development of the Implantable Glucose Sensor: What Are the Prospects and Why Is It Taking So Long?", Diabetes, 1995, vol. 44, pp. 1005-1009.

Hermanides, J., et al., "Current Application of Continuous Glucose Monitoring in the Treatment of Diabetes", Diabetes Care, 2011, vol. 34, Suppl. 2, pp. S197-S201.

Insert Molding, 1996, retrieved from https://www.mddionline.com/equipment/insert-molding, 4 pages.

International Diabetes Device 2022 Blue Book, Seagrove Partners, 142 pages.

Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.

Lomas, P., "Dexcom G7 Release: The Most Exciting New Features", 2024, retrieved from https://notjustapatch.com/dexcom-g7-features/, 13 pages.

Lovett, L., "What's next for Dexcom? Ceo, Cto talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.

Medtronic Enlite Serter User Guide, 2014, 26 pages.

Meltsner, M A, et al., "Observations on rotating needle insertions using a brachytherapy robot", Phys. Med. Biol., 2007, vol. 52, pp. 6027-6037.

Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.

"Periphery", Cambridge Dictionary of American English, 2000, p. 631.

"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.

"Real-World Data Show Abbott's Freestyle LibreR Systems And GLP-1 Medicines Work Better Together For People With Type 2 Diabetes", 2024, PRNewswire, 2 pages.

Sclater, N., et al., eds., Mechanisms and Mechanical Devices Sourcebook, Fourth Edition, 2007, Chapter 12—Shaft Couplings and Connections, pp. 290-307.

Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.

Van Den Boom, L., et al., "Changes in the utilization of blood glucose test strips among patients using intermittent-scanning con-

(56) References Cited

OTHER PUBLICATIONS tinuous glucose monitoring in Germany", Diabetes, Obesity and Metabolism, 2020, vol. 22, pp. 922-928.
CA 3,050,721 Examiner's Report Nov. 8, 2024.
EP 19151577.4 Examination Report Oct. 7, 2024.
EP 20177703.4 Response to Withdrawals Jan. 7, 2025.
EP 20177703.4 Withdrawal of Intervention Dec. 27, 2024.
EP 20177703.4 Withdrawal of Opposition Dec. 27, 2024.
EP 20177703.4 Written Submissions Dexcom Nov. 22, 2024.
EP 20195922.8 Withdrawal of Intervention Dec. 27, 2024.
EP 20195922.8 Withdrawal of Opposition Dec. 27, 2024.
EP 21211041.5 Withdrawal of Opposition Dec. 27, 2024.
EP 21211041.5 Notice of Appeal Dec. 17, 2024.
EP 21211041.5 Response to Summons to Attend Oral Proceedings Dexcom Nov. 12, 2024.
EP 21211041.5 Response to Summons to Attend Oral Proceedings Nov. 12, 2024.
EP 24152079.0 Examination Report Dec. 2, 2024.
EP 24183336.7 Extended Search Report Oct. 11, 2024.
EP 24194029.5 Extended Search Report Nov. 18, 2024.
EP 24201435.5 Extended Search Report Jan. 27, 2025.
JP 2024-31538 Office Action Oct. 16, 2024.
MY PI2022002786 Examination Report Jan. 8, 2025.
UP Second Expert Opinion of Dr Michael Schoemaker in Litigation of EP 3977921 Nov. 8, 2024.
Decision Denying Institution of Inter Partes Review, IPR No. 2024-00860 Nov. 20, 2024.
Patent Owner's Response To Petitioner's Explanation Of Parallel Petitions Challenging U.S. Pat. No. 11,510,325, IPR No. 2024-00860 Aug. 23, 2024.
Patent Owner Preliminary Response Pursuant to 37 C.F.R. § 42.107, IPR No. 2024-00860 Aug. 23, 2024.
Declaration of Julia Castellano, IPR No. 2024-00860 Aug. 21, 2024.
Declaration of Scott E. Davis, IPR No. 2024-00860 Jun. 5, 2024.
Petitioner's Explanation Of Parallel Petitions Challenging U.S. Pat. No. 11,510,325, IPR No. 2024-00860 May 9, 2024.
Patent Owner's Request For Oral Argument, IPR No. 2023-01409 Dec. 3, 2024.
Petitioner's Request For Oral Argument, IPR No. 2023-01409 Dec. 3, 2024.
Patent Owner's Objections to Petitioner's Exhibits Submitted With Its Reply, IPR No. 2023-01409 Nov. 1, 2024.
Petitioner's Updated Exhibit List, IPR No. 2023-01409 Oct. 25, 2024.
Second Declaration of Gary Fletcher, Ph.D., IPR No. 2023-01409 Oct. 25, 2024.
Petitioner's Reply to Patent Owner's Response, IPR No. 2023-01409, Oct. 25, 2024.
Deposition of Karl R. Leinsing, MSME, PE, IPR No. 2023-01409 Oct. 17, 2024.
Conference Call Before The Patent Trial And Appeal Board • Before Judge Cynthia Hardman, IPR No. 2023-01409 Oct. 17, 2024.
Notice of Joint Stipulation to Modify Schedule, IPR No. 2023-01409 Sep. 26, 2024.
Declaration of Karl R. Leinsing, MSME, PE, IPR No. 2023-01409 Jul. 19, 2024.
Patent Owner's Response, IPR No. 2023-01409 Jul. 19, 2024.
Deposition of Gary Fletcher, Ph.D., IPR No. 2023-01409 Jun. 26, 2024.
Decision Denying Patent Owner's Request on Rehearing of Decision Denying Institution, IPR No. 2023-01396 Aug. 9, 2024.
Ex Parte Reexamination Certificate of U.S. Pat. No. 11,013,440 Oct. 30, 2024.
Reexamination U.S. Appl. No. 90/019,331 Ex Parte Rexxamination Certificate Nov. 14, 2024.
Reexamination U.S. Appl. No. 90/019,331 Notice of Intent to Issue Ex Parte Reexamination Certificate Oct. 15, 2024.
Reexamination U.S. Appl. No. 90/019,331 Petition Under 37 CFR § 1.59 to Expunge Application Papers Jun. 12, 2024.
Ex Parte Reexamination Certificate of U.S. Pat. No. 10,959,654, Nov. 5, 2024.
Abbott Patent Marking Diabetes, 2024, retrieved from https://www.abbott.com/patents/diabetes-patents.html, 6 pages.
ACCU-CHEK® Softclix Lancet Device retrieved from file:///C:/Users/afredericks/Downloads/softclix-user-manual.pdf, 2007, 2 pages.
Using your ACCU-CHEK® Multiclix Lancet Device, 2005, retrieved from https://www.northcoastmed.com/wp-content/uploads/2023/03/multiclix_userguide.pdf, 2 pages.
"The Advantages of the Cleo® 90 Infusion Set Are Clear", 2019, retrieved from https://web.archive.org/web/20220816002119/https://smiths-medical.com/-/media/M/Smiths-medical_com//Files/Import-Files/Product-Literature/IN193873GB-092019_LR.pdf, 2 pages.
American National Standard, ANSI/AAMI HE75:2009, Human factors engineering—Design of medical devices, 2010, 465 pages.
Automated Retractable VanishPoint Syringe 510(k) Safety and Effectiveness Summary, 1998, 5 pages.
"Bluetooth rival unveiled by Nokia", 2006, retrieved from News.bbc.co.uk/1/hi/technology/5403564.stm, 2 pages.
Breton, M., et al., "Fully Integrated Artificial Pancreas in Type 1 Diabetes: Modular Closed- Loop Glucose Control Maintains Near Normoglycemia", Diabetes, 2012, vol. 61, No. 9, pp. 2230-2237.
Burge, M. R., et al., "Continuous Glucose Monitoring: The Future of Diabetes Management", Diabetes Spectrum, 2008, vol. 21, No. 2, pp. 112-119.
Clancy, N. T., et al., "A new device for assessing changes in skin viscoelasticity using indentation and optical measurement", Skin Research and Technology, 2010, vol. 16, pp. 210-228.
Cleo® 90 Infusion Set 510(k) Premarket Notification, 2004, 1 page.
Dexcom G5 Mobile System User Guide, 2015, pp. 1-260.
Dexcom STS Continuous Monitors FDA Premarket Approval (PMA), 2006, 2 pages.
U.S. Appl. No. 61/569,287.
Freestyle Navigator Answers to Frequently Asked Questions, 2007, retrieved from https://web.archive.org/web/20080917183534/http://www.freestylenavigator.com/ab_nav/url/content/en_US/3 0.10.10:1 O/general_content/General_ContenL0000004.htm, 2 pages.
"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.
International Standard, IEC 62366, Medical devices—Application of usability engineering to medical devices, 2007, 214 pages.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
Medtronic MiniMed Guardian@ Real-Time Components, 2007, retrieved from https://web.archive.org/20071013095335/http:/www.medtronicdiabetes.com/products/guardian/components.html, 2 pages.
Medtronic MiniMed Guardian® Real-Time Features, 2007, retrieved from https://web.archive.org/20071025084715/http:/www.medtronicdiabetes.com/products/guardia n/features.html, 2 pages.
Medtronic MiniMed One-press Serter User Guide, 2015, 26 pages.
Medtronic MiniMed Paradigm® 512 and 712 Insulin Pumps User Guide, 2005, pp. 1-136.
Microlet® 2 Lancing Device, 2008, retrieved from https://image.tigermedical.com/Manuals/BAY6606-20141216010820833.pdf, 1 page.
Piper, H. G., et al., "Real-Time Continuous Glucose Monitoring in Pediatric Patients During and After Cardiac Surgery", Pediatrics, 2006, vol. 118, No. 3, pp. 1176-1184.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.
Sacks, A. H., et al., "Skin blood flow changes and tissue deformations produced by cylindrical indentors", Journal of Rehabilitation Research and Development, 1985, vol. 22, No. 3, pp. 1-6.

(56)                    References Cited

OTHER PUBLICATIONS

Schneider, M., et al., "Evaluating the use of the Cleo® 90 infusion set for patients on a palliative care unit", International Journal of Palliative Nursing, 2009, vol. 15,. No. 8, pp. 372-376.
AU 2019404908 Examiner's Report, Feb. 17, 2025.
CA 3,228,738 Examiner's Report, May 8, 2025.
CN 202211091194.1 Notification of Filing Divisional Application, Mar. 27, 2025.
EP 17182379.2 Reply to Reply to Opposition, May 16, 2025.
EP 17182379.2 Reply to Opposition, Feb. 27, 2025.
EP 19900891.3 Examination Report, May 8, 2025.
EP 21211041.5 Grounds of Appeal, Apr. 23, 2025.
EP 21211041.5 Minutes of Oral Proceedings, Dec. 13, 2024.
EP 23190032.5 Examination Report, May 19, 2025.
JP 2023-516522 Office Action, Mar. 5, 2025.
JP 2023-514023 Office Action, Apr.16, 2025.
MX MX/a/2021/007294 Second Office Action, Feb. 19, 2025.
MY PI2021003022 Examination Report, Mar. 5, 2025.
Termination Due to Settlement After Institution of Trial, IPR No. 2023-01409, Jan. 7, 2025.
Joint Motion to Treat Settlement Agreement as Business Confidential Information. IPR No. 2023-01409, Jan. 3, 2025.
Joint Motion to Terminate Proceeding Under 35 U.S.C. § 317(a), IPR No. 2023-01409, Jan. 3, 2025.
Order Setting Oral Argument, IPR No. 2023-01409, Dec. 11, 2024.
Patent Owner's Sur-Reply, IPR No. 2023-01409, Dec. 10, 2024.
Deposition of Gary D. Fletcher, Ph.D., IPR No. 2023-01409, Dec. 4, 2024.

Reexamination No. U.S. Appl. No. 90/019,307 Office Action, Mar. 18, 2025.
Reexamination No. U.S. Appl. No. 90/019,307 Decision on Petition, Feb. 13, 2025.
Reexamination U.S. Appl. No. 90/019,329 Decision on Petition Under 37 C.F.R. § 1.181, Mar. 18, 2025.
WO PCT/US25/13698 Invitation to Pay Additional Fees. Apr. 15, 2025.
CN 202180063087.5 First Office Action Aug. 14, 2025.
EP 17182379.2 Written Submissions Aug. 6, 2025.
EP 17182379.2 Summons to Attend Oral Proceedings Jul. 4, 2025.
EP 19151577.4 Examination Report Sep. 3, 2025.
EP 20177712.5 Written Submissions Gulde Aug. 21, 2025.
EP 20177712.5 Response to Summons to Attend Oral Proceeding Aug. 21, 2025.
EP 21192910.4 Notice of Opposition Stolmar Sep. 10, 2025.
EP 21192910.4 Notice of Opposition Strawman Sep. 10, 2025.
EP 24218309.3 Extended Search Report Jul. 9, 2025.
EP 24194029.5 Examination Report Aug. 26, 2025.
EP 24220160.6 Extended Search Report Jun. 17, 2025.
JP 2023-514023 Final Office Action Aug. 20, 2025.
JP 2023-514024 Office Action Apr. 30, 2025.
JP 2023-532327 Office Action Jul. 23, 2025.
JP 2025-026588 Office Action Aug. 27, 2025.
Reexamination No. U.S. Appl. No. 90/019,307 Final Office Action Jul. 8, 2025.
WO PCT/US25/13698 ISR and Written Opinion Jun. 5, 2025.
WO PCT/US25/27260 Invitation to Pay Additional Fees Jul. 24, 2025.
EP 18741791.0 Examination Report, Sep. 12, 2025.
WO PCT/US2025/027260 ISR and Written Opinion, Sep. 16, 2025.

* cited by examiner

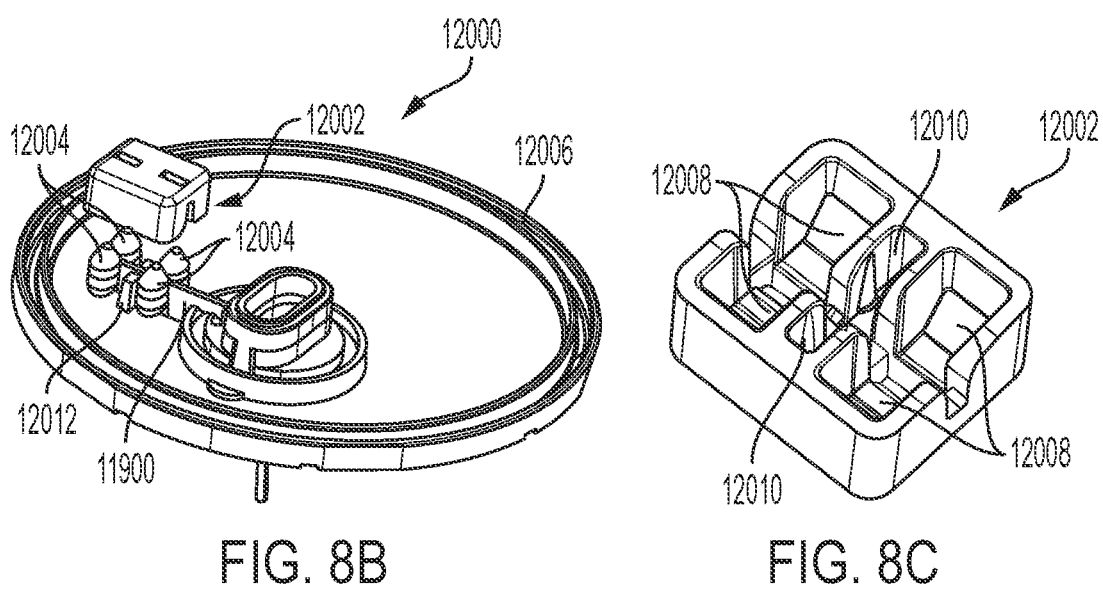
FIG. 8B
FIG. 8C
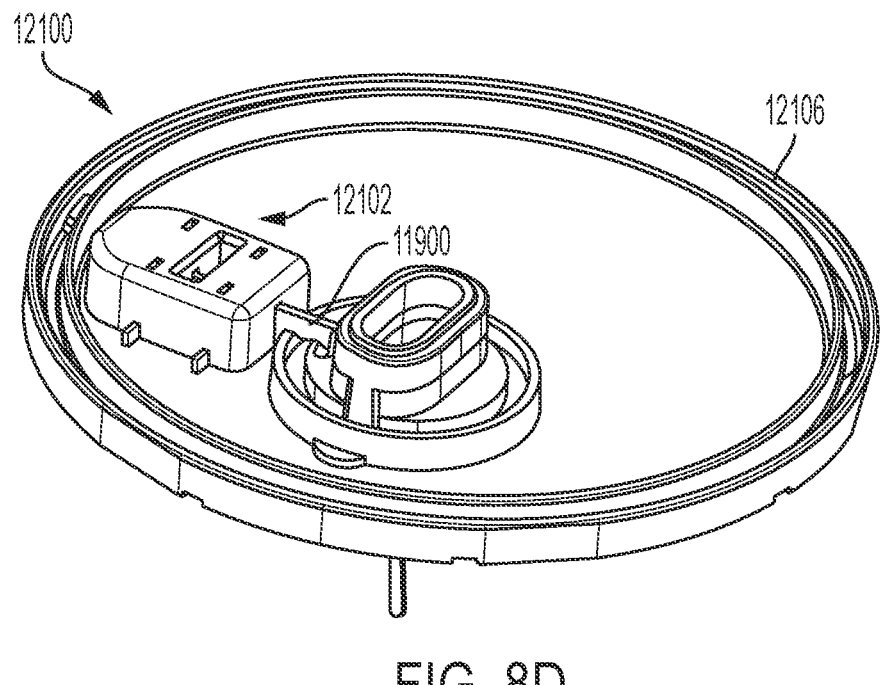
FIG. 8D

SYSTEMS, DEVICES, AND METHODS FOR ANALYTE MONITORING

CROSS-REFERENCE TO RELATED APPLICATIONS

This application is a continuation of U.S. application Ser. No. 17/865,843, filed Jul. 15, 2022, which claims priority to U.S. Provisional Application No. 63/222,851, filed Jul. 16, 2021, which is herein expressly incorporated by reference in its entirety for all purposes.

FIELD

The subject matter described herein relates generally to systems, devices, and methods for in vivo analyte monitoring.

BACKGROUND

The detection and/or monitoring of analyte levels, such as glucose, ketones, lactate, oxygen, hemoglobin AIC, or the like, can be vitally important to the health of an individual having diabetes. Patients suffering from diabetes mellitus can experience complications including loss of consciousness, cardiovascular disease, retinopathy, neuropathy, and nephropathy. Diabetics are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device may be worn on the body of an individual who requires analyte monitoring. To increase comfort and convenience for the individual, the sensor control device may have a small form-factor, and can be assembled and applied by the individual with a sensor applicator. The application process includes inserting a sensor using an applicator or insertion mechanism, such that the sensor comes into contact with a bodily fluid. The sensor control device may also be configured to transmit analyte data to another device, from which the individual or her health care provider ("HCP") can review the data and make therapy decisions.

While current sensors can be convenient for users, they are also susceptible to malfunctions and/or mechanical failures due to improper handling and/or storage of the sensor and/or applicator, user error, lack of proper training, poor user coordination, overly complicated procedures, and other issues. This can be particularly true for analyte monitoring systems having in vivo analyte sensors used to measure an analyte level in an interstitial fluid ("ISF"), and which are inserted using sharps (also known as "introducers" or "needles"). Some prior art systems, for example, may utilize certain mechanisms and features that are susceptible to failure or reduced efficacy due to adverse conditions. These challenges and others described herein can lead to improperly inserted or damaged sensors, and consequently, a failure to properly monitor the patient's analyte level.

Thus, needs exist for more reliable sensor insertion devices, as well as systems and methods relating thereto, that are easy to use by the patient, less prone to error, and less susceptible to malfunctions or mechanical failures.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to an applicator for delivering a sensor control device. The applicator can include a housing configured to move between a first position and a second position; a sheath slidably coupled with the housing; a sharp carrier coupled with a sharp, a sensor control device comprising an analyte sensor coupled with sensor electronics, and a sensor carrier.

In some embodiments, the applicator can include an applicator cap threadably coupled with the housing, wherein the applicator cap and housing define an interior space, and wherein the interior space comprises a lightly pressurized inert gas.

According to some embodiments, the sharp carrier of the applicator can comprise one or more magnets, wherein the sensor control device further comprises one or more ferromagnetic components, and wherein the one or more magnets are configured to exert a magnetic force upon the ferromagnetic components in a proximate direction such that the sensor control device is retained in the sensor carrier when the housing is in the first position.

In some embodiments, the sensor control device can include a connector assembly comprising a pull-tab, wherein the pull-tab is comprised of an electrically insulative material, and wherein the pull-tab is removably engaged with a plurality of sensor contacts of the analyte sensor. In other embodiments, the pull-tab can be coupled with a power supply in the sensor control device. According to some embodiments, the sensor control device can further comprise an adhesive liner coupled with a bottom surface of an adhesive patch on the bottom surface of the sensor control device.

In some embodiments, the applicator can further comprise a leaf spring coupled with a sharp, wherein the sharp is configured to position at least a portion of the analyte sensor under a skin surface when the housing is moved to the second position, and wherein the leaf spring is configured to retract the sharp into the applicator after the housing is moved to the second position.

Other systems, devices, methods, features and advantages of the subject matter described herein will be or will become apparent to one with skill in the art upon examination of the following figures and detailed description. It is intended that all such additional systems, devices, methods, features, and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 8A and 8B are isometric and partially exploded isometric views of an example connector assembly, according to one or more embodiments.

FIG. 8C is an isometric bottom view of the connector of FIGS. 8A-8B.

FIGS. 8D and 8E are isometric and partially exploded isometric views of another example connector assembly, according to one or more embodiments.

FIG. 8F is an isometric bottom view of the connector of FIGS. 8D-8E.

DETAILED DESCRIPTION

Figure 1:
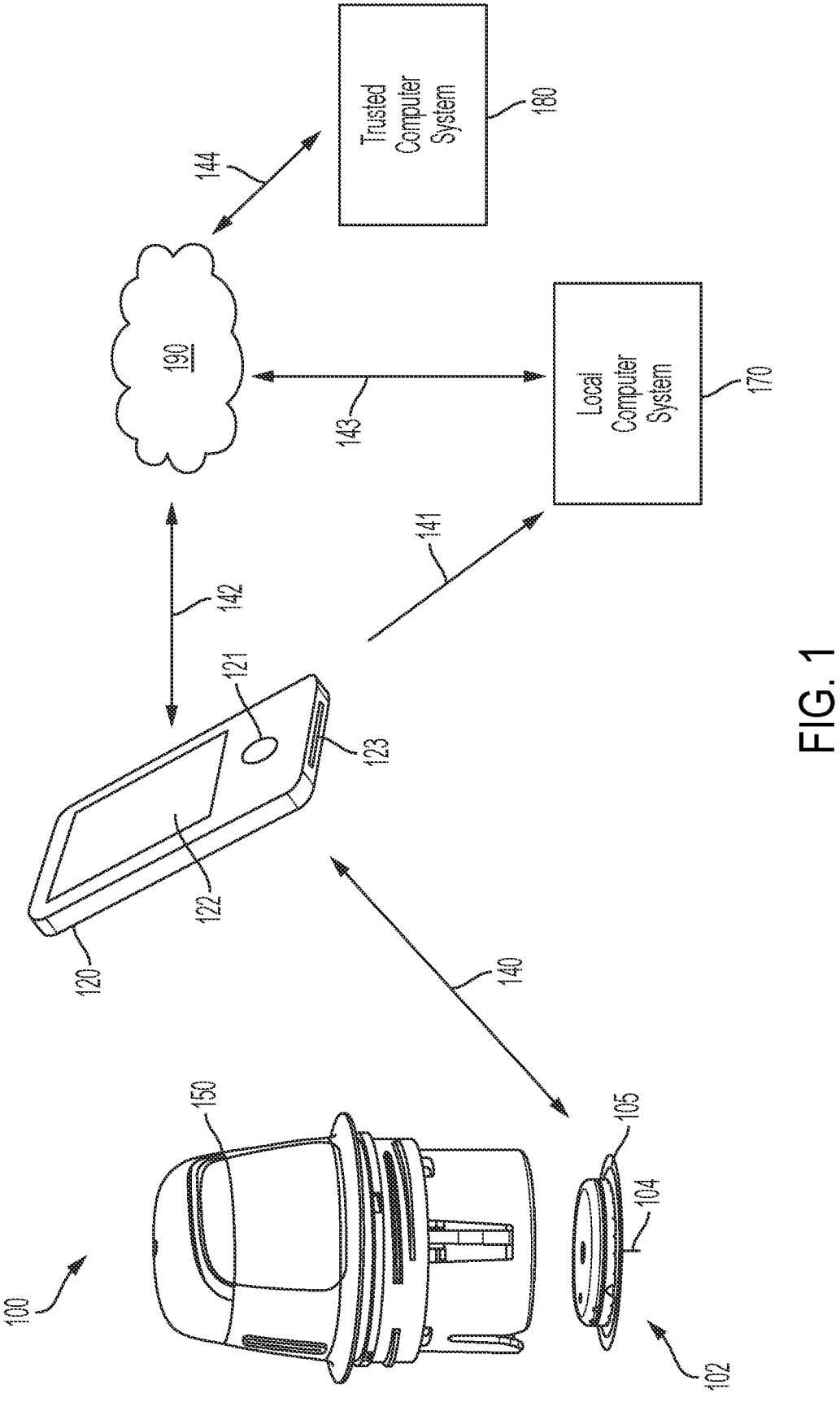
FIG. 1 is a system overview of a sensor applicator, reader device, monitoring system, network, and remote system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices, and methods for the use of analyte sensor insertion applicators for use with in vivo analyte monitoring systems. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer's bodily fluid. Some embodiments provided herein are improvements to maintain the sterility of the applicator, sensor control device, and/or analyte sensor during storage. Some embodiments provided herein reduce the susceptibility of the applicator, sensor control device, and/or analyte sensor to malfunction and mechanical failure. Other improvements and advantages are provided as well. The various configurations of these devices are described in detail by way of the embodiments which are only examples.

Furthermore, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

As mentioned, a number of embodiments of systems, devices, and methods are described herein that provide for improvements to sensor insertion devices and sensor control devices for use with in vivo analyte monitoring systems. In particular, several embodiments of the present disclosure are designed to improve the longevity of certain components of a sensor applicator device and reduce their susceptibility to mechanical failure. Some embodiments, for example, include a pull-tab comprising an electrically insulative material coupled with one or more of: the sensor contacts, power supply, or another component of the sensor electronics. In certain embodiments, the pull-tab can be configured to prevent electrical coupling between the power supply and the sensor electronics of the sensor control device, thereby preserving the power supply of the sensor control device during storage or shipment. In another embodiment, a leaf spring retraction mechanism is implemented in a sensor applicator to reduce the number of potential sensor applicator device components susceptible to mechanical failure. In yet another embodiment, a plurality of magnetic elements is employed to retain a sensor control device in a sensor carrier of the applicator, and also reduces the number of sensor applicator device components susceptible to mechanical failure. Consequently, these embodiments can improve the longevity and functionality of sensor applicator devices and the sensor control devices, to name a few advantages.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Exemplary In Vivo Analyte Monitoring System

FIG. 1 is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121 and the device battery can be recharged using power port 123. Reader device 120 can communicate with local computer system 170 via a communication path 141 using a wired or wireless technique. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by wired or wireless technique as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique.

Exemplary Reader Device

Figure 2A:
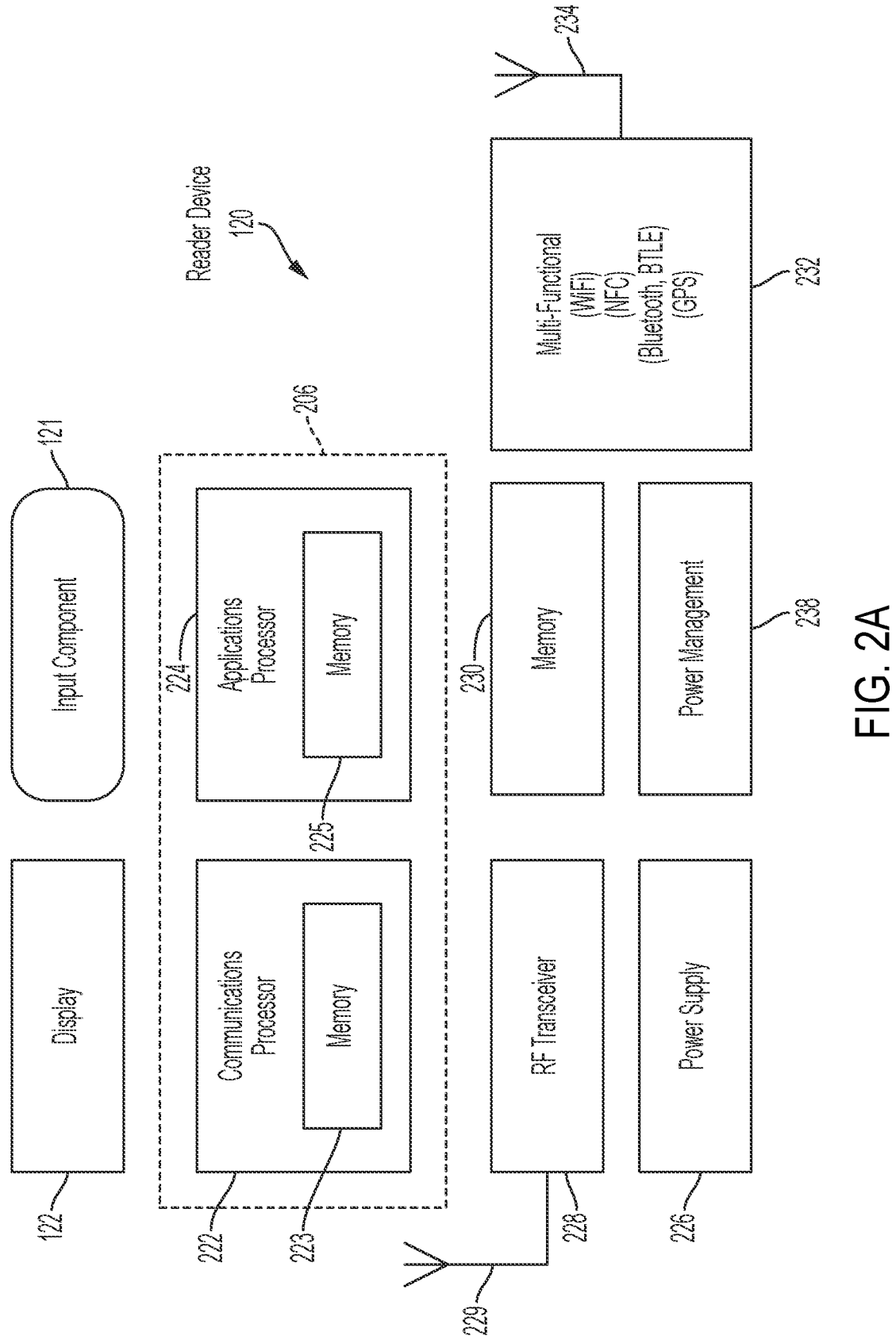
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further included can be a multifunctional transceiver 232 which can communicate over Wi-Fi, NFC, Bluetooth, BTLE, and GPS with an antenna 234. As understood by one of skill in the art, these components are electrically and communicatively coupled in a manner to make a functional device.

Exemplary Sensor Control Devices

Figures 2B, 2C:
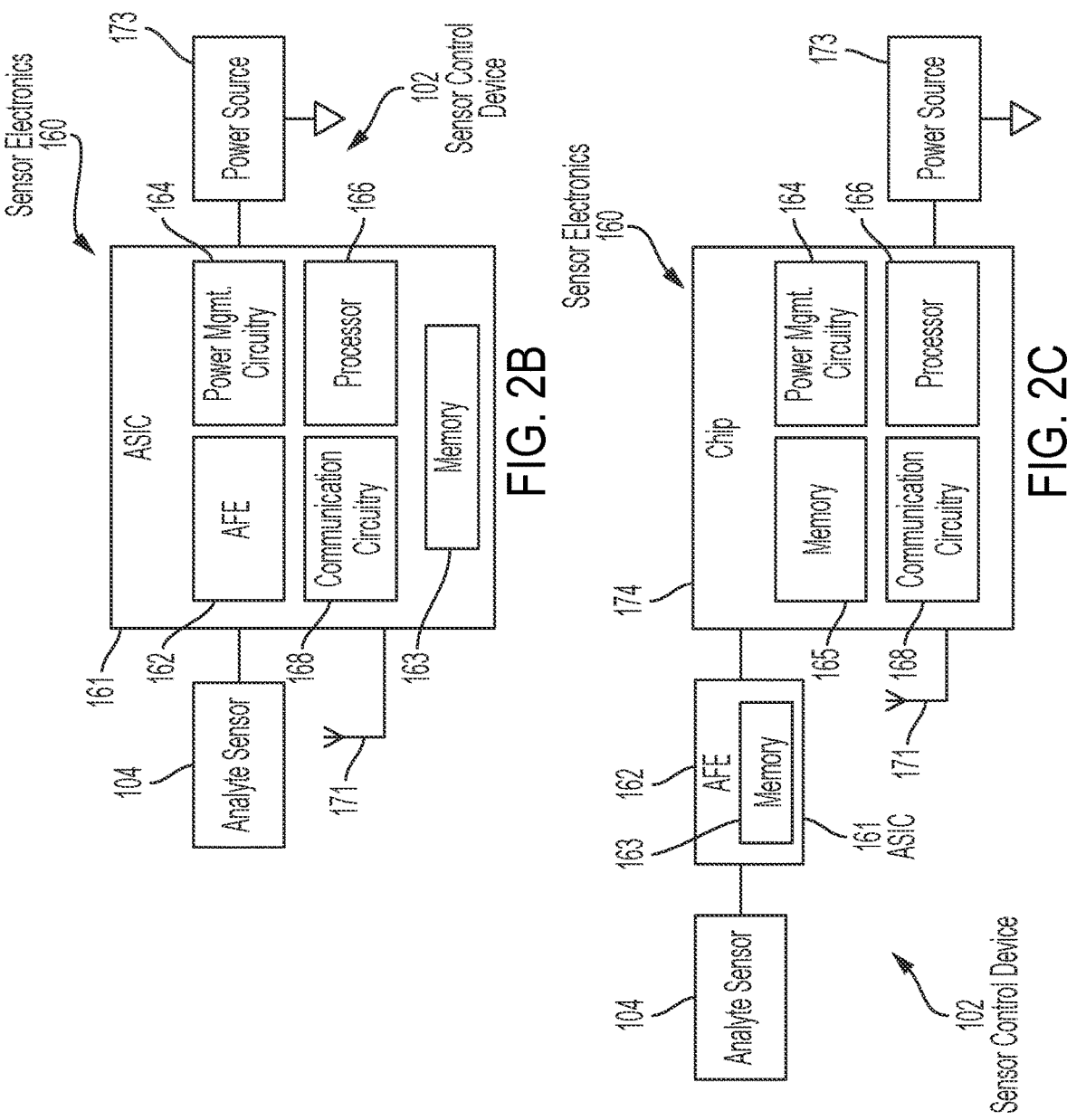
FIGS. 2B and 2C are block diagrams depicting example embodiments of sensor control devices.

FIGS. 2B and 2C are block diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 173, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Exemplary Assembly Processes for Sensor Control Devices

The components of sensor control device 102 can be acquired by a user in multiple packages requiring final assembly by the user before delivery to an appropriate user location. FIGS. 3A-3D depict an example embodiment of an assembly process for sensor control device 102 by a user, including preparation of separate components before coupling the components in order to ready the sensor for delivery. FIGS. 3E-3F depict an example embodiment of delivery of sensor control device 102 to an appropriate user location by selecting the appropriate delivery location and applying device 102 to the location.

Figures 3A, 3B, 3C:
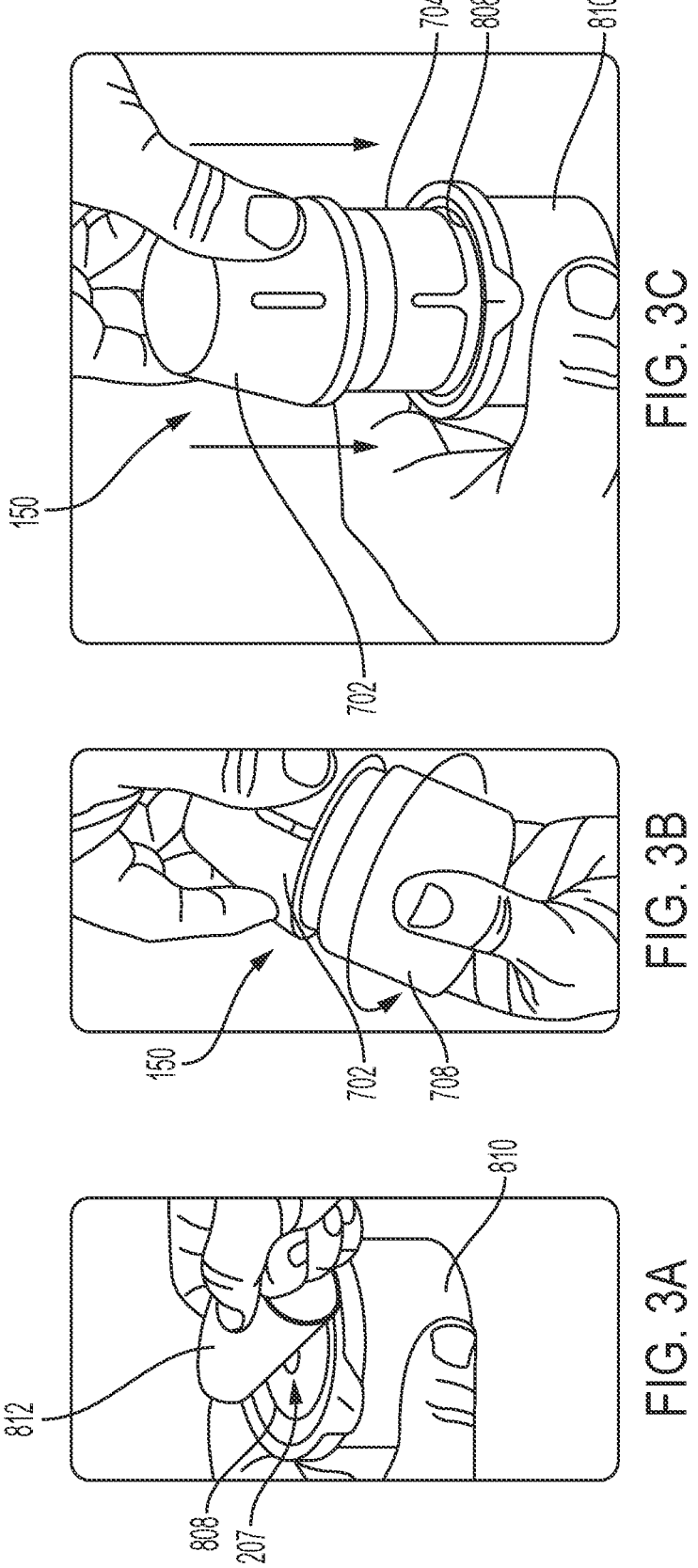
FIGS. 3A-3G are progressive views of an example embodiment of the assembly and application of an in vivo analyte monitoring system incorporating a two-piece architecture.
Figure 3E:
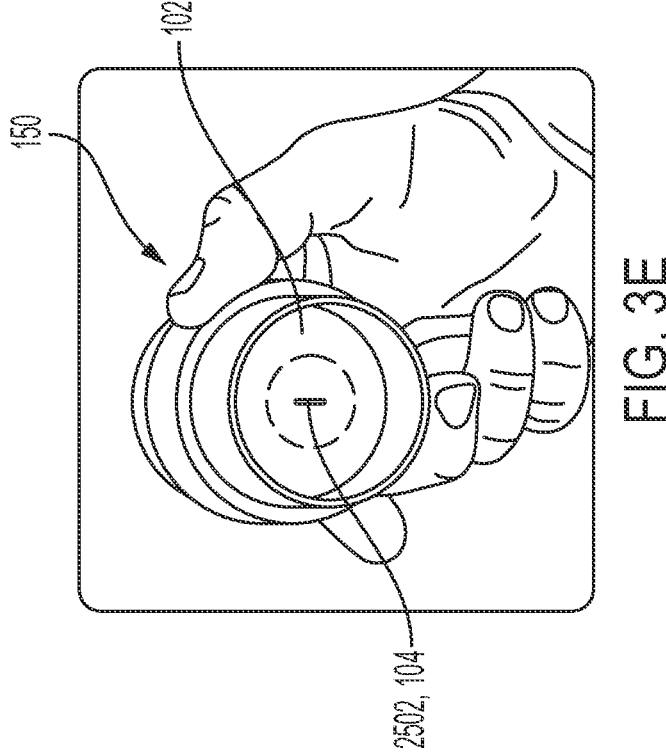

FIG. 3A is a proximal perspective view depicting an example embodiment of a user preparing a container 810, configured here as a tray (although other packages can be used), for an assembly process. The user can accomplish this preparation by removing lid 812 from tray 810 to expose platform 808, for instance by peeling a non-adhered portion of lid 812 away from tray 810 such that adhered portions of lid 812 are removed. Removal of lid 812 can be appropriate in various embodiments so long as platform 808 is adequately exposed within tray 810. Lid 812 can then be placed aside.

FIG. 3B is a side view depicting an example embodiment of a user preparing an applicator device 150 for assembly. Applicator device 150 can be provided in a sterile package sealed by a cap 708. Preparation of applicator device 150 can include uncoupling housing 702 from cap 708 to expose sheath 704 (FIG. 3C). This can be accomplished by unscrewing (or otherwise uncoupling) cap 708 from housing 702. Cap 708 can then be placed aside.

FIG. 3C is a proximal perspective view depicting an example embodiment of a user inserting an applicator device 150 into a tray 810 during an assembly. Initially, the user can insert sheath 704 into platform 808 inside tray 810 after aligning housing orienting feature 1302 (or slot or recess) and tray orienting feature 924 (an abutment or detent). Inserting sheath 704 into platform 808 temporarily unlocks sheath 704 relative to housing 702 and also temporarily unlocks platform 808 relative to tray 810. At this stage, removal of applicator device 150 from tray 810 will result in the same state prior to initial insertion of applicator device 150 into tray 810 (i.e., the process can be reversed or aborted at this point and then repeated without consequence).

Sheath 704 can maintain position within platform 808 with respect to housing 702 while housing 702 is distally advanced, coupling with platform 808 to distally advance platform 808 with respect to tray 810. This step unlocks and collapses platform 808 within tray 810. Sheath 704 can contact and disengage locking features (not shown) within tray 810 that unlock sheath 704 with respect to housing 702 and prevent sheath 704 from moving (relatively) while housing 702 continues to distally advance platform 808. At the end of advancement of housing 702 and platform 808, sheath 704 is permanently unlocked relative to housing 702. A sharp and sensor (not shown) within tray 810 can be coupled with an electronics housing (not shown) within housing 702 at the end of the distal advancement of housing 702. Operation and interaction of the applicator device 150 and tray 810 are further described below.

Figure 3D:
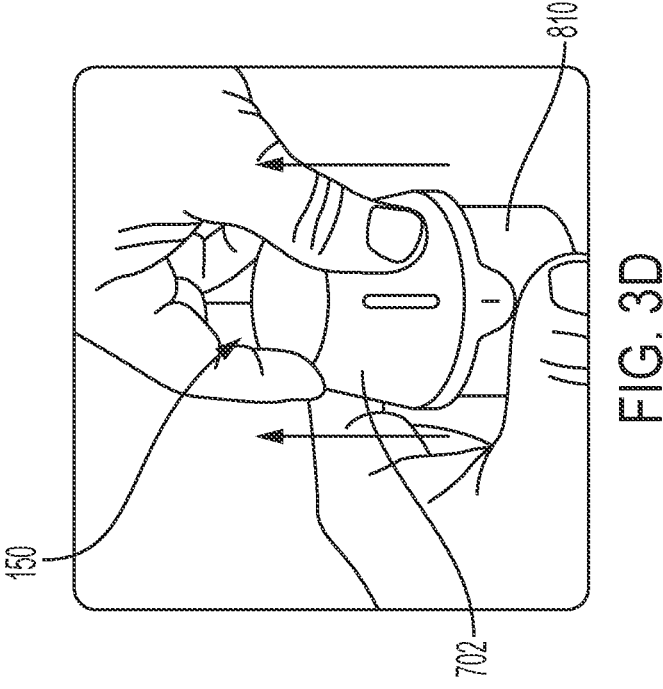
Figure 3G:
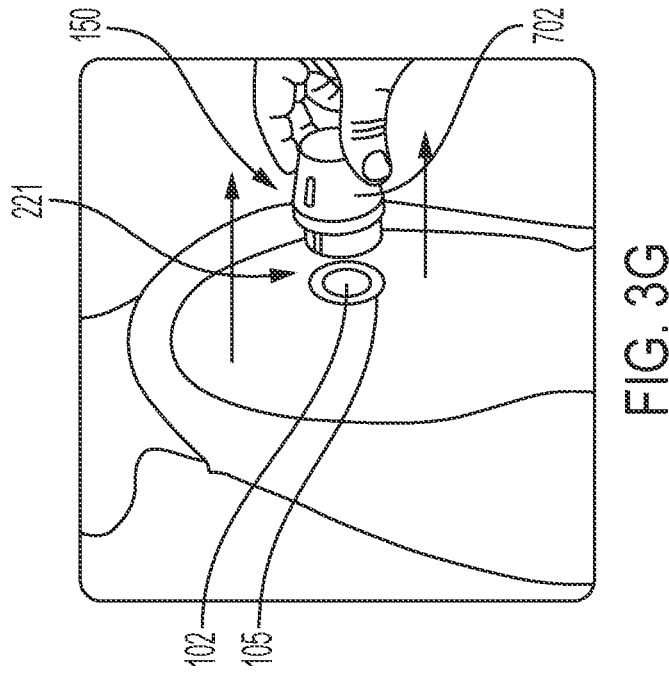
Figure 3F:
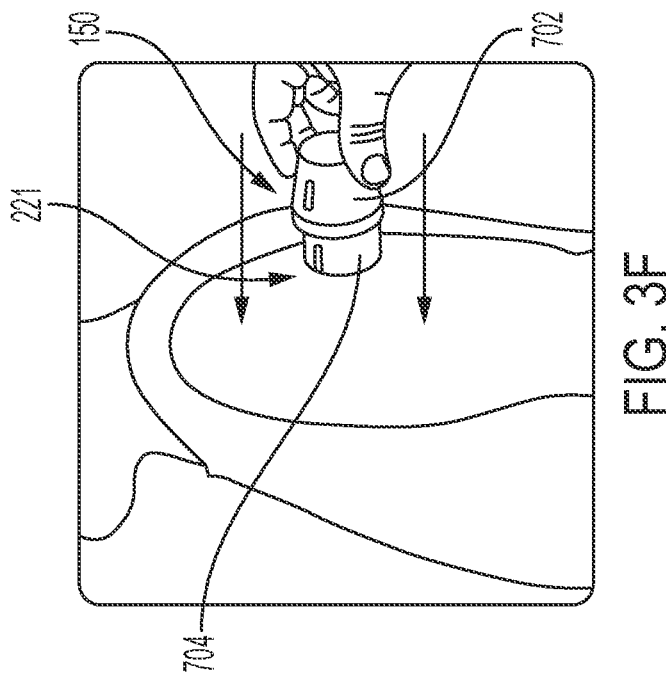

FIG. 3D is a proximal perspective view depicting an example embodiment of a user removing an applicator device 150 from a tray 810 during an assembly. A user can remove applicator 150 from tray 810 by proximally advancing housing 702 with respect to tray 810 or other motions having the same end effect of uncoupling applicator 150 and tray 810. The applicator device 150 is removed with sensor control device 102 (not shown) fully assembled (sharp, sensor, electronics) therein and positioned for delivery.

FIG. 3E is a proximal perspective view depicting an example embodiment of a patient applying sensor control device 102 using applicator device 150 to a target area of skin, for instance, on an abdomen or other appropriate location. Advancing housing 702 distally collapses sheath 704 within housing 702 and applies the sensor to the target location such that an adhesive layer on the bottom side of sensor control device 102 adheres to the skin. The sharp is automatically retracted when housing 702 is fully advanced, while the sensor (not shown) is left in position to measure analyte levels.

FIG. 3F is a proximal perspective view depicting an example embodiment of a patient with sensor control device 102 in an applied position. The user can then remove applicator 150 from the application site.

System 100, described with respect to FIGS. 3A-3F and elsewhere herein, can provide a reduced or eliminated chance of accidental breakage, permanent deformation, or incorrect assembly of applicator components compared to prior art systems. Since applicator housing 702 directly engages platform 808 while sheath 704 unlocks, rather than indirect engagement via sheath 704, relative angularity between sheath 704 and housing 702 will not result in breakage or permanent deformation of the arms or other components. The potential for relatively high forces (such as in conventional devices) during assembly will be reduced, which in turn reduces the chance of unsuccessful user assembly.

Exemplary Sensor Applicator Devices

Figures 4A, 4B, 4C:
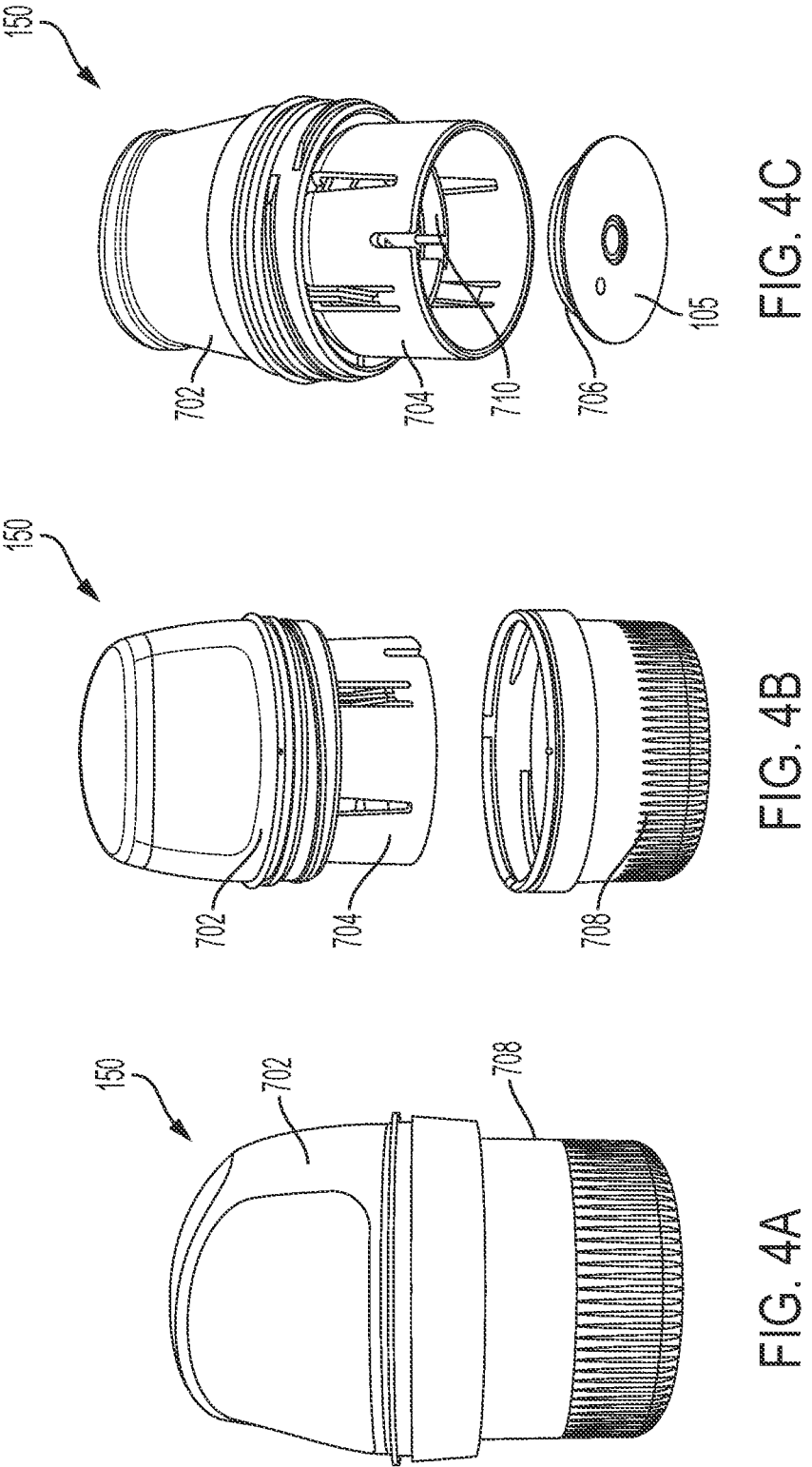
FIG. 4A is a side view depicting an example embodiment of an applicator device coupled with a cap.
FIG. 4B is a side perspective view depicting an example embodiment of an applicator device and cap decoupled.
FIG. 4C is a perspective view depicting an example embodiment of a distal end of an applicator device and electronics housing.

FIG. 4A is a side view depicting an example embodiment of an applicator device 150 coupled with screw cap 708. This is an example of how applicator 150 is shipped to and received by a user, prior to assembly by the user with a sensor. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within sensor carrier 710 of sheath 704, when cap 708 is in place.

Figure 4E:
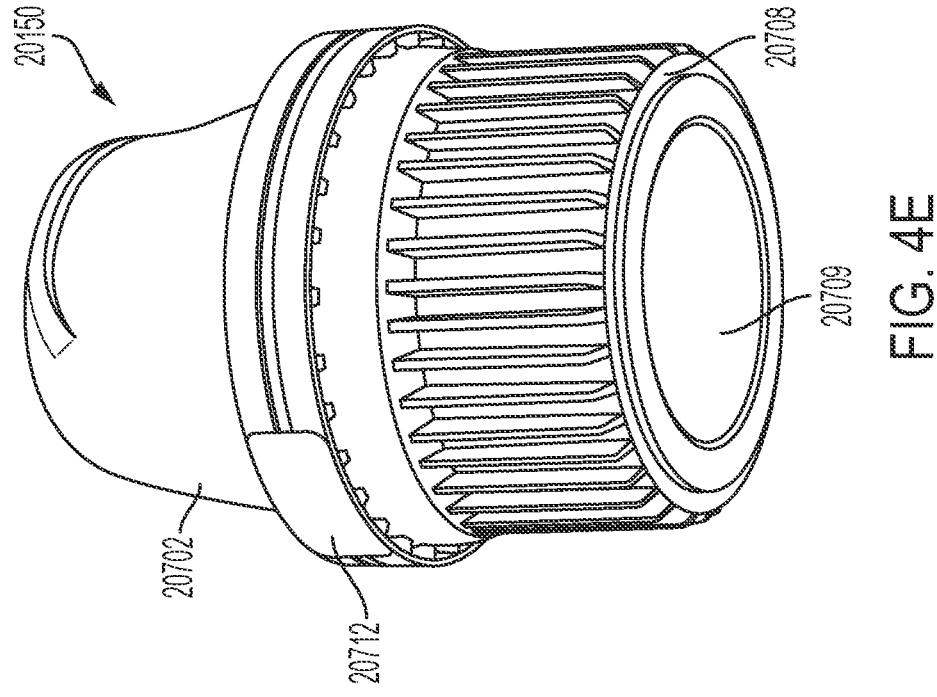
FIG. 4E is a bottom perspective view of the applicator device of FIG. 4D.
Figure 4D:
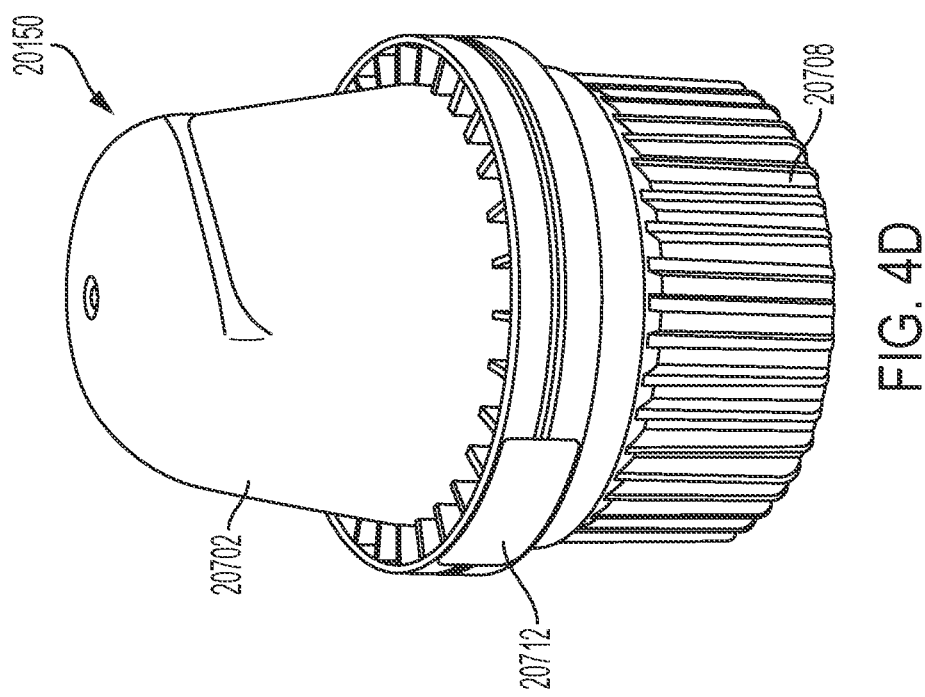
FIG. 4D is a top perspective view of an exemplary applicator device in accordance with the disclosed subject matter.
Figure 4F:
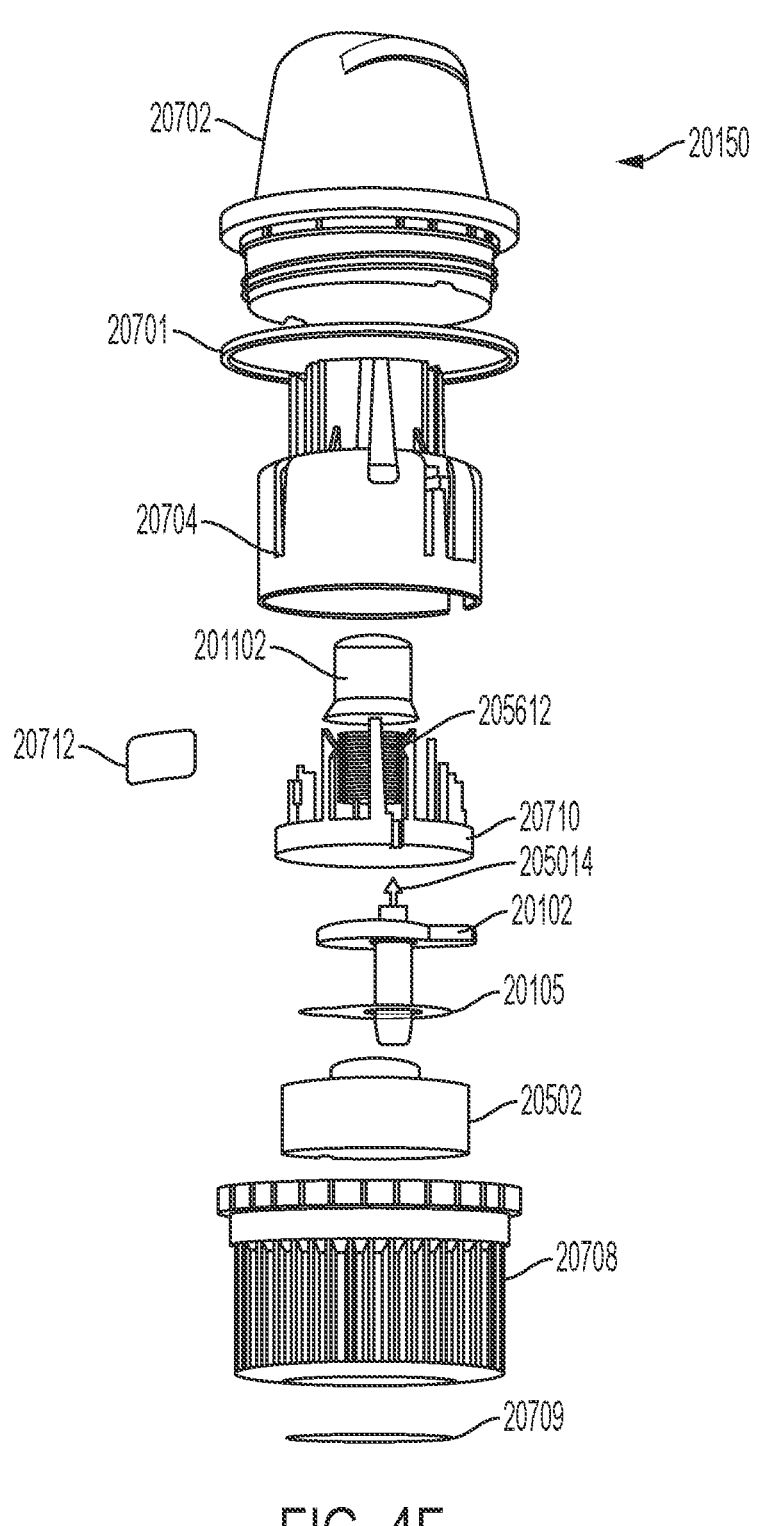
FIG. 4F is an exploded view of the applicator device of FIG. 4D.
Figure 4G:
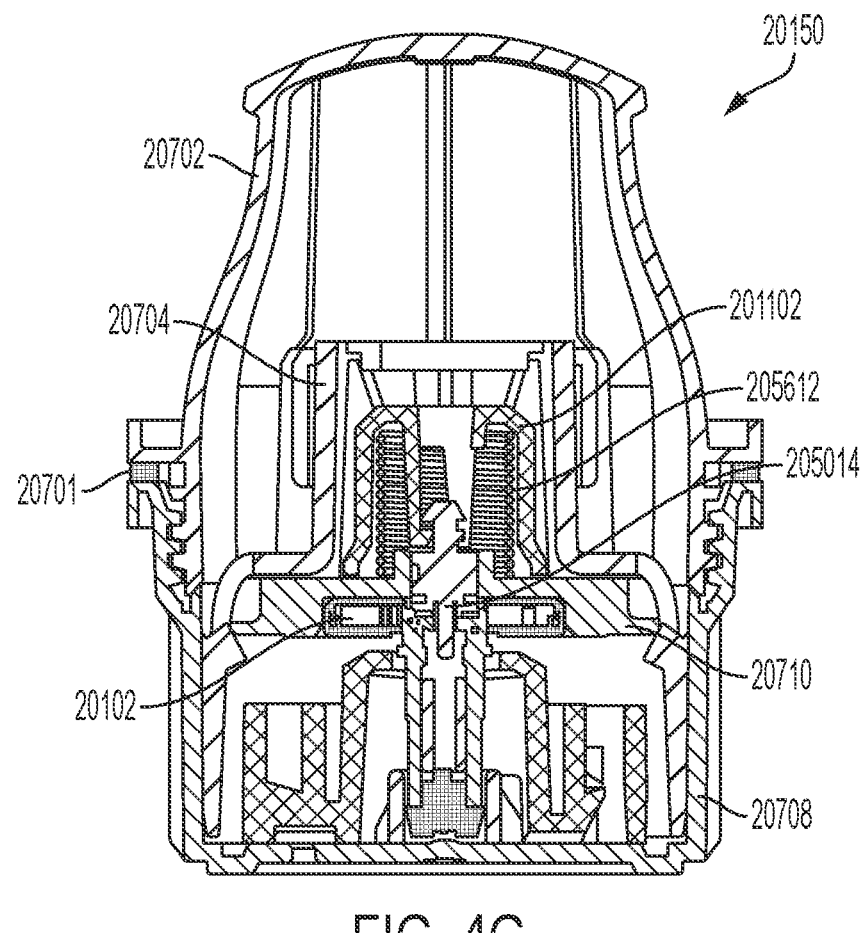
FIG. 4G is a side cutaway view of the applicator device of FIG. 4D.

Referring to FIG. 4D-G for purpose of illustration and not limitation, the applicator device 20150 can be provided to a user as a single integrated assembly. FIGS. 4D and 4E provide perspective top and bottom views, respectively, of the applicator device 20150, FIG. 4F provides an exploded view of the applicator device 20150 and FIG. 4G provides a side cut-away view. The perspective views illustrate how applicator 20150 is shipped to and received by a user. The exploded and cut-away views illustrate the components of the applicator device 20150. The applicator device 20150 can include a housing 20702, gasket 20701, sheath 20704, sharp carrier 201102, spring 205612, sensor carrier 20710 (also referred to as a "puck carrier"), sharp hub 205014, sensor control device (also referred to as a "puck") 20102, adhesive patch 20105, desiccant 20502, cap 20708, serial label 20709, and tamper evidence feature 20712. As received by a user, only the housing 20702, cap 20708, tamper evidence feature 20712, and label 20709 are visible. The tamper evidence feature 20712 can be, for example, a sticker coupled to each of the housing 20702 and the cap 20708, and tamper evidence feature 20712 can be damaged, for example, irreparably, by uncoupling housing 20702 and cap 20708, thereby indicating to a user that the housing 20702 and cap 20708 have been previously uncoupled. These features are described in greater detail below.

Referring to FIG. 4G, in some embodiments, the interior of housing 20702 and cap 20708 can be lightly pressurized with an inert gas during assembly. According to one aspect of some embodiments, filling the interior of housing 20702 and cap 20708 with an inert, dry gas (e.g., nitrogen or argon) during assembly can be used either in place of, or in addition to, a desiccant. According to another aspect of some embodiments, lightly pressurizing the interior of housing 20702 and cap 20708 with an inert gas can also outwardly bias the flow of materials across the seal formed by housing 20702 and cap 20708, and can reduce the chance of ingress of unwanted contaminants. Moreover, as a further advantage of some embodiments, a slight release of gas pressure from the applicator when the user removes cap 20708 can be audible to indicate to the user that the seal has not been compromised during shipping and/or storage.

According to another aspect of some embodiments, an inert gas can be introduced into the interior of housing 20702 using a closed temperature-controlled system (not shown). First, one or more applicator devices 20150 can be placed into the closed system, while the closed system is at a first predetermined temperature. In some embodiments, the closed system can already be filled with the inert gas before the applicator devices 20150 are placed within. In other embodiments, the closed system can be filled with the inert gas after the applicator devices 20150 are placed within. The closed system is sealed such that the inert gas is prevented from escaping, while other external gases cannot enter. According to an aspect of some embodiments, when the closed system is maintained at the first predetermined temperature, applicator housing 20702 and cap 20708 form a seal, as described in the previous sections. Subsequently, the closed system is heated to a second predetermined temperature greater than the first predetermined temperature. According to an aspect of some embodiments, at the second predetermined temperature, for each of the one or more applicator devices 20150, the thermal expansion of cap 20708 can be different (e.g., greater or less) than the thermal expansion of the corresponding housing 20702, thereby unsealing each applicator device 20150. Consequently, the inert gas can diffuse into the interior of each housing 20702 while the applicator device 20150 is in an unsealed state. After a predetermined amount of time has elapsed that is sufficient to allow the inert gas to diffuse into each housing 20702, the temperature of the closed system can then be reduced to a lower temperature. In some embodiments, the lower temperature can be the first predetermined temperature. In other embodiments, the lower temperature can be a third predetermined temperature that is different from the first predetermined temperature, but is also lower than the second predetermined temperature. At the lower temperature, cap 20708 can contract such that the seal with the housing 20702 can be formed once again. Finally, the one or more applicators can be removed from the closed system.

Exemplary Sensor Carriers

Figure 5A:
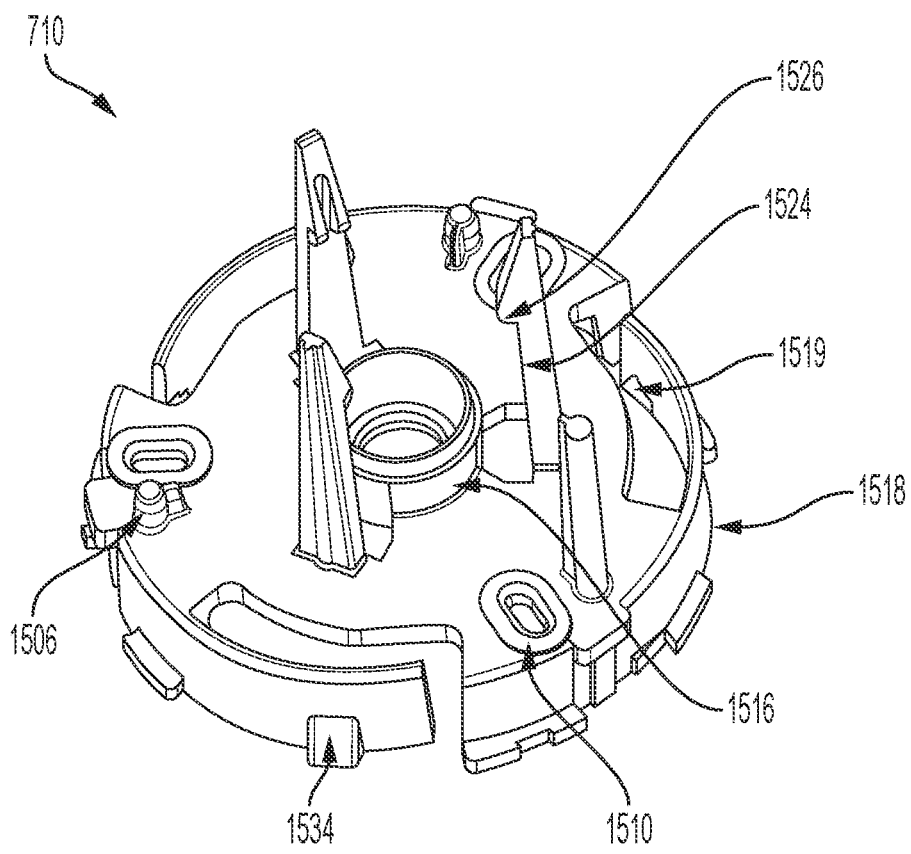
FIG. 5A is a proximal perspective view depicting an example embodiment of a sensor carrier.

FIG. 5A is a proximal perspective view depicting an example embodiment of sensor carrier 710 that can retain sensor control device within applicator 150. It can also retain sharp carrier 2102 with sharp module 2500. In this example embodiment, sensor carrier 710 generally has a hollow round flat cylindrical shape, and can include one or more deflectable sharp carrier lock arms 1524 (e.g., three) extending proximally from a proximal surface surrounding a centrally located spring alignment ridge 1516 for maintaining alignment of spring 1104. Each lock arm 1524 has a detent or retention feature 1526 located at or near its proximal end. Shock lock 1534 can be a tab located on an outer circumference of sensor carrier 710 extending outward and can lock sensor carrier 710 for added safety prior to firing. Rotation limiter 1506 can be a proximally extending relatively short protrusion on a proximal surface of sensor carrier 710 which limits rotation of carrier 710. Sharp carrier lock arms 1524 can interface with sharp carrier 2102 as described with reference to FIGS. 6A-6E below.

Figure 5B:
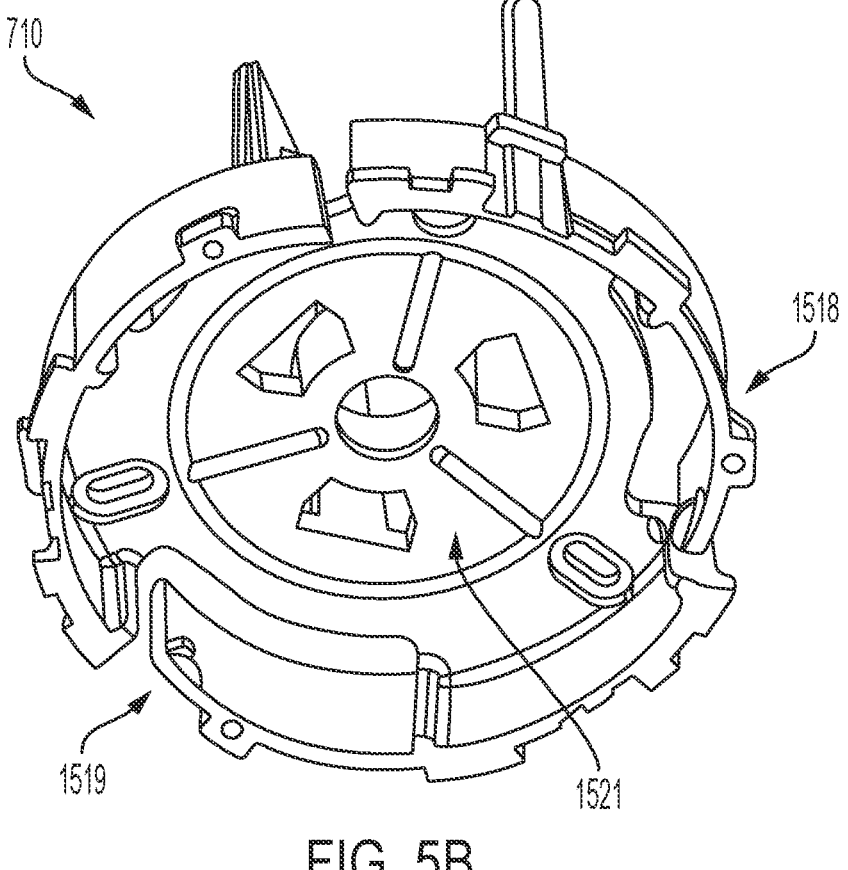
FIG. 5B is a distal perspective view depicting an example embodiment of a sensor carrier.

FIG. 5B is a distal perspective view of sensor carrier 710. Here, one or more sensor electronics retention spring arms 1518 (e.g., three) are normally biased towards the position shown and include a detent 1519 that can pass over the distal surface of electronics housing 706 of device 102 when housed within recess or cavity 1521. In certain embodiments, after sensor control device 102 has been adhered to the skin with applicator 150, the user pulls applicator 150 in a proximal direction, i.e., away from the skin. The adhesive force retains sensor control device 102 on the skin and overcomes the lateral force applied by spring arms 1518. As a result, spring arms 1518 deflect radially outwardly and disengage detents 1519 from sensor control device 102 thereby releasing sensor control device 102 from applicator 150.

Figure 5C:
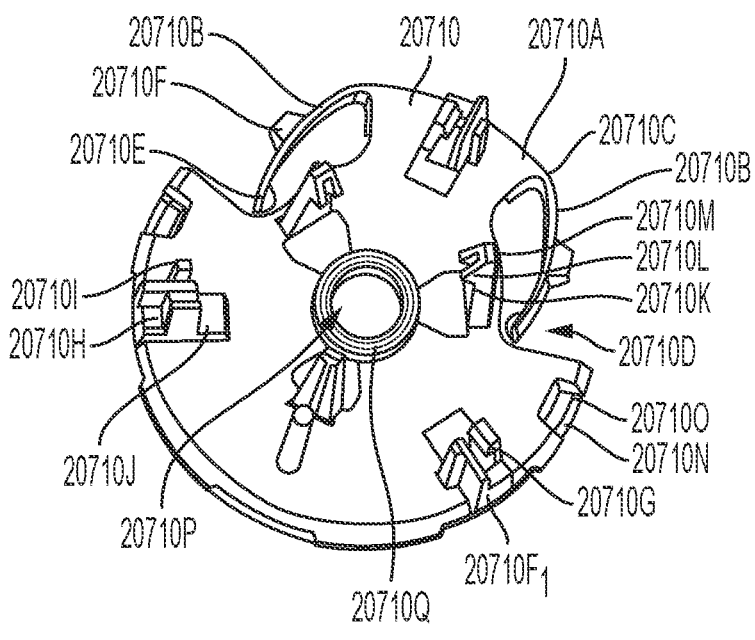
FIG. 5C is a top perspective view of a sensor carrier in accordance with the disclosed subject matter.
Figure 5D:
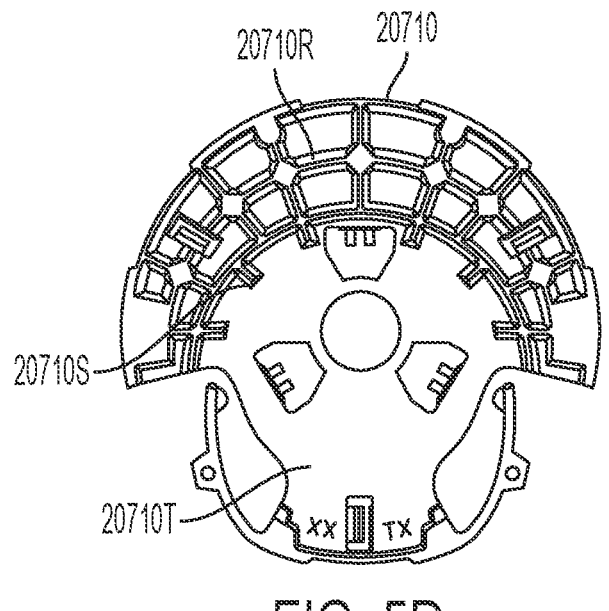
FIG. 5D is a bottom view of the sensor carrier of FIG. 5C.

Referring to FIGS. 5C and 5D, for purpose of illustration and not limitation, an exemplary sensor carrier 20710 is provided. Sensor carrier 20710 can include one or more of the features described herein with regard to sensor carriers, wherein similar features can operate as described herein. For example, sensor carrier 20710 can include a base 20710A and first and second retention arms 20710B. Each retention arm 20710B can include a first end portion 20710C coupled to the base 20710A and a free end portion 20710D. For example, each retention arm 20710B can be coupled to the base 20710A at a first half of the base 20710A and the free end portion 20710D can extend toward a second half of the base 20710A. Each retention arm 20710B can include a sensor retention feature 20710E disposed on an inner surface of the sensor retention arm 20710B. The sensor retention feature 20710E can be disposed on the free end portion 20710D. The sensor retention feature 20710E can be configured to retain the sensor control device 20102 within the housing 20702. The retention feature 20710E can include a conical surface and angular parting line, which can allow for release of the sensor control device 20102 upon delivery. Each retention arm 20710 can include a lock interface 20710F disposed on an outer surface of the retention arm 20710B. The lock interface 20710F can engage rib 20704U on the sheath 20704. As described hereinabove, the rib 20704U can prevent the sensor retention arm 20710B from flexing outwardly, for example, during a shock event, and therefore can keep retention feature 20710E engaged with the sensor control device 20102, and thereby prevent movement of the sensor control device 20102 during a shock event.

In some embodiments, sensor control device (e.g., 102 or 20102) can be retained in sensor carrier (e.g., 710 or 20710) by one or more magnets (not shown) disposed on a sharp carrier. According to one aspect of some embodiments, and as further described below with respect to FIGS. 6A-6D, one or more magnets disposed in the sharp carrier can be configured to attract one or more ferromagnetic components disposed in sensor control device (e.g., 102 or 20102) and, consequently, retain sensor control device (e.g., 102 or 20102) in sensor carrier (e.g., 710 or 20710). In some embodiments, the one or more ferromagnetic components can be disposed in a housing of the sensor control device (e.g., 102 or 20102). In some embodiments, the one or more magnets can be implemented either in addition to, or in place of, the one or more sensor electronics retention spring arms 1518 and corresponding detents 1519 of sensor carrier 710

(FIGS. 5A-5B), or retention arms 20710B with corresponding sensor retention features 20710E of sensor carrier 20710 (FIGS. 5C-5D). In certain embodiments, it may be preferable to implement the one or more magnets without spring arms 1518, detents 1519, retention arms 201710B, and sensor retention features 20710E because such structural features can be subject to adverse conditions during storage or use that can cause, for example, material creep over time.

In other embodiments, sensor control device (e.g., 102 or 20102) can be retained in sensor carrier (e.g., 710 or 20710) by one or more magnets disposed in the sensor carrier itself. According to one aspect of some embodiments, one advantage of locating the one or more magnets in the sensor carrier (e.g., 710 or 20710) is the proximity between the one or more magnets and the sensor control device (e.g., 102 or 20102). As a result, less magnetic force may be required because, in some embodiments, the one or more magnets in the sensor carrier can be configured to directly engage at least a portion of the sensor control device (e.g., a top portion). Furthermore, according to another aspect of some embodiments, the adhesive patch can be configured such that the adhesive property is greater than the magnetic force between the one or more magnets and the sensor control device. Accordingly, after the sensor control unit reaches the distal position and the adhesive patch is coupled with the skin, the sensor control unit can disengage from the sensor carrier when the user pulls the applicator device away from the skin.

Referring back to FIGS. 5C and 5D, sensor carrier 20710 can include a plurality of housing attachment features 20710F1. In some embodiments, for example, sensor carrier 20710 can include three housing attachment features 20710F1. In other embodiments, sensor carrier 20710 can include two, four, five, six, or more housing attachment features 20710F1. The housing attachment features 20710F1 can be equally spaced on the sensor carrier 20710 and can extend upwardly from a top surface of the sensor carrier 20710. Each sensor housing attachment feature 20710F1 can include a housing snap 20710G, housing locator feature 20710H, biasing feature 20710I, and housing stop 20710J. The housing locator feature 20710H can axially locate the sensor carrier 20710 relative the housing 20702 when the two are to be coupled together. The housing snap 20710G can engage the sensor carrier attach slots 20702K on the housing 20702 to couple the sensor carrier 20710 to the housing 20702. The biasing feature 20710I can engage sensor carrier biasing feature 20702M on housing 20702 configured to remove slop between the sensor carrier 20710 and the housing 20702.

Sensor carrier 20710 can further include a plurality of sharp carrier lock arms 20710K, for example three sharp carrier lock arms 20710K. The sharp carrier lock arms 20710K can be equally spaced on the sensor carrier 20710 and can extend upwardly form a top surface of the sensor carrier 20710. Each sharp carrier lock arm 20710K can include a sharp carrier retention feature 20710L and a rib 20710M. Rib 20710M can engage an inner surface of the sheath 20704, which can urge the sharp carrier lock arm 20710K inwardly and cause sharp carrier retention feature 20710L to retain sharp carrier 201102, as described in greater detail below. The carrier retention feature 20710L can have a triangle shape when viewed in side view and a "U" shape when viewed in top view.

In accordance with the disclosed subject matter, the sensor carrier 20710 can include a plurality of lock ledges 20710N configured to engage lock arm interface 20704M of the sheath 20704 as described herein above. For example, the sensor carrier 20710 can include two lock ledges 20710N. Sensor carrier 20710 can include recesses 207100 disposed proximate each lock ledge 20710N and configured to receive the lock arm interface 20704M during firing, to prevent the lock arm 20704J from engaging with housing 20702 during firing. Sensor carrier 20710 can include a hole 20710P extending through a middle of the base 20710A. The hole 20710P can guide and limit movement of sharp hub 205014 during insertion. Additionally, or alternatively, sensor carrier 20710 can include spring locator 20710Q.

A bottom surface of the sensor carrier 20710 can include stiffening ribs 20710R and sensor locator ribs 20710S, which can limit planar motion of the sensor control device 20102 relative the sensor carrier 20710. The bottom surface of the sensor carrier 20710 can include a sensor support surface 20710T configure to support the sensor control device 20102.

Exemplary Sharp Carriers

Figure 6B:
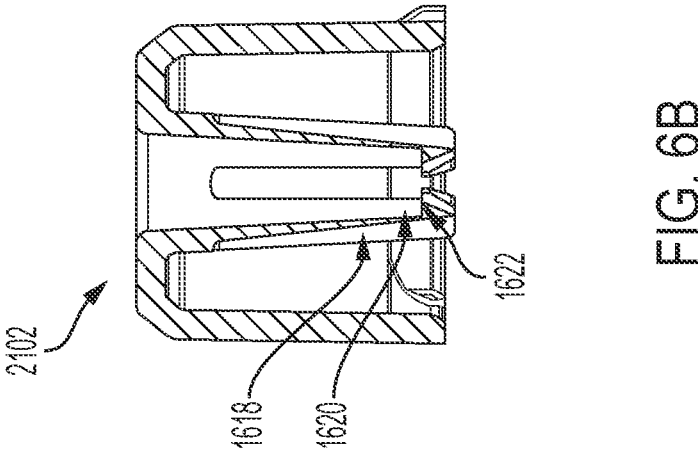
FIG. 6B is a side cutaway view of the sharp carrier of FIG. 6A.
Figure 6A:
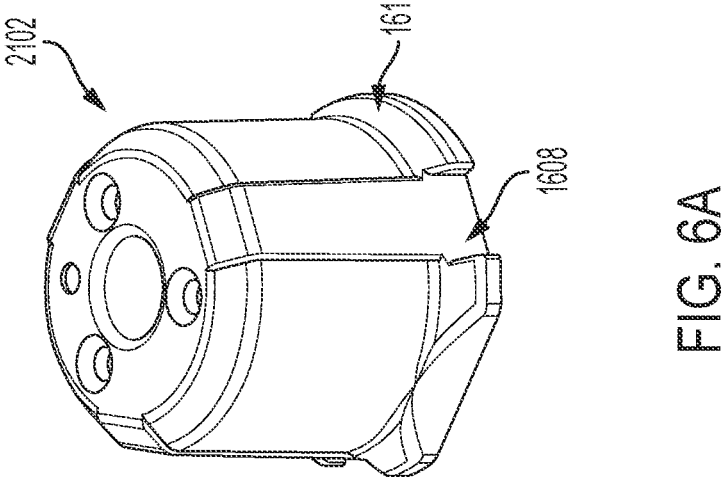
FIG. 6A is a perspective view of a sharp carrier in accordance with the disclosed subject matter.
Figure 9A:
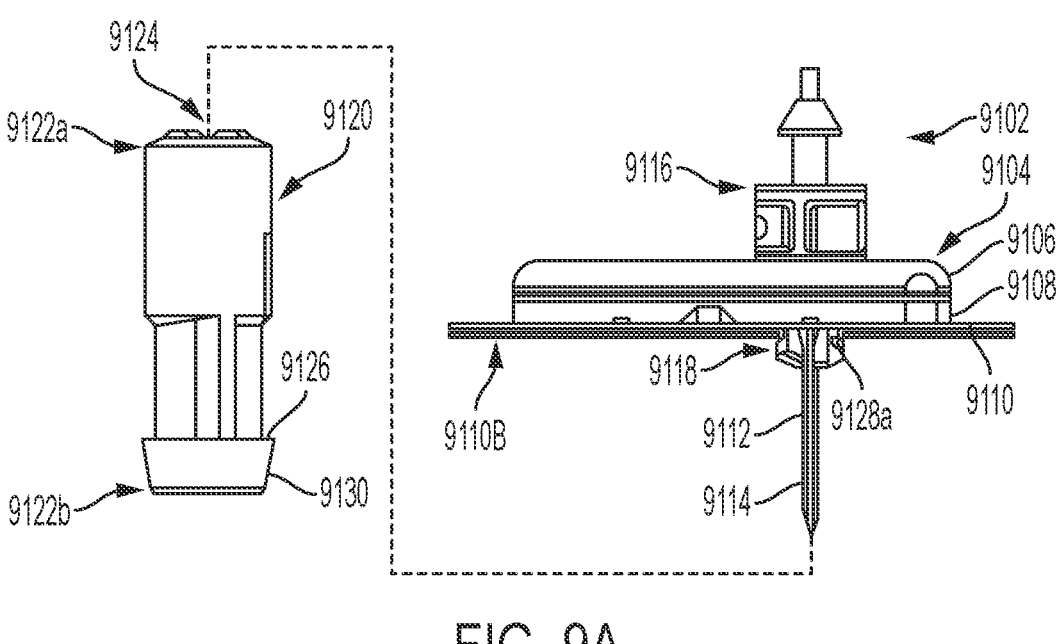
FIGS. 9A and 9B are side and isometric views, respectively, of an example sensor control device, according to one or more embodiments of the present disclosure.

FIGS. 6A and 6B are a proximal perspective view and a side cross-sectional view, respectively, depicting an example embodiment of sharp carrier 2102. Sharp carrier 2102 can grasp and retain sharp module 2500 within applicator 150. It can also automatically retract as a result of one or more springs changing from a preloaded, compressed state to an expanded state during an insertion process, as described with respect to FIGS. 10A-10E. Near a distal end of sharp carrier 2102 can be anti-rotation slots 1608 which prevent sharp carrier 2102 from rotating when located within a central area of sharp carrier lock arms 1524 (as shown in FIG. 9A). Anti-rotation slots 1608 can be located between sections of sharp carrier base chamfer 1610, which can ensure full retraction of sharp carrier 2102 through sheath 704 upon retraction of sharp carrier 2102 at the end of the deployment procedure.

As shown in FIG. 6B, sharp retention arms 1618 can be located in an interior of sharp carrier 2102 about a central axis and can include a sharp retention clip 1620 at a distal end of each arm 1618. Sharp retention clip 1620 can have a proximal surface which can be nearly perpendicular to the central axis and can abut a distally facing surface of sharp hub 2516.

Figure 6C:
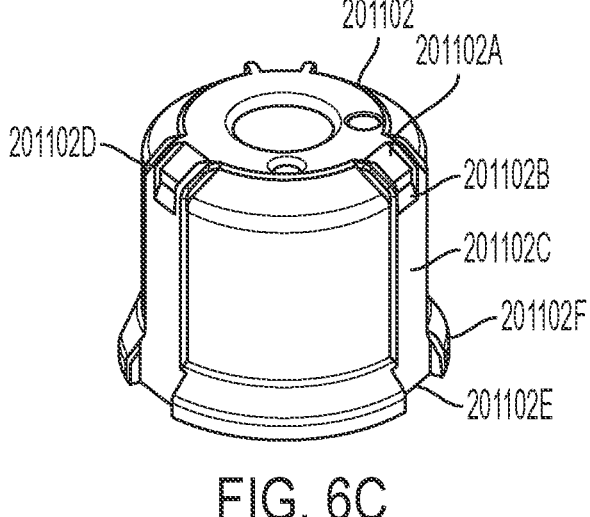
FIG. 6C is a perspective view of a sharp carrier in accordance with the disclosed subject matter.
Figure 6D:
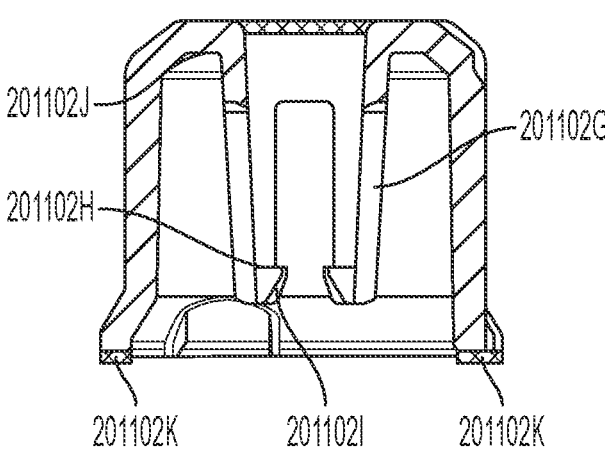
FIG. 6D is a side cutaway view of the sharp carrier of FIG. 6C.

Referring to FIGS. 6C and 6D, for purpose of illustration and not limitation, an exemplary sharp carrier 201102 is provided. Sharp carrier 201102 can include one or more features described herein with regard to sharp carriers, wherein similar features can operate as describe herein. For example, sharp carrier 201102 can include a series of features for engaging with the three sharp carrier lock arms 20710K of the sensor carrier 20710. The features can include a pre-partial-retraction retention face 201102A and a post-partial-retraction retention face 201102B. The pre-partial retraction retention face 201102A can engage the sharp carrier retention feature 20710L prior to partial retraction, for example, during shipping and storage. Post-partial-retraction retention face 201102B can engage the sharp carrier retention feature 20710L after partial retraction. For example, as the sheath 20704 initially move proximally relative to the sensor carrier 20710, the rib 20710M of the retention arm 20710L can engage slot 20704Q of sheath 20704, which can allow the retention arm 20710L to move radially outward and allow sharp carrier retention feature 20710L to clear the pre-partial retraction retention face 201102A and engage the post-partial retraction retention face 201102B. A height between the end of the pre-partial-retraction face 201102A and the start of the post-partial-retraction face 201102B can be the distance of the partial retraction. A running face 201102C can be disposed below the post-partial-retraction retention face 201102B and can slide against the retention arm 20710L as the sharp carrier 201102 is retracted. Alignment walls 201102D can help to keep the sharp carrier 201102 aligned with the sensor carrier 20704 during partial retraction. Sharp carrier 201102 can include a chamfer 201102F, which can include anti-rotation slots 201102E to engage the retention arms 20710L on the sensor carrier 20710.

Internally, sharp carrier 201102 can include sharp retention arms 201102G including lead-in face 201102I and sharp hub contact face 201102H. The retention arms 201102G can receive and hold sharp hub 205014. Spring stop 201102J can engage retraction spring 205612.

Figures 10A, 10B:
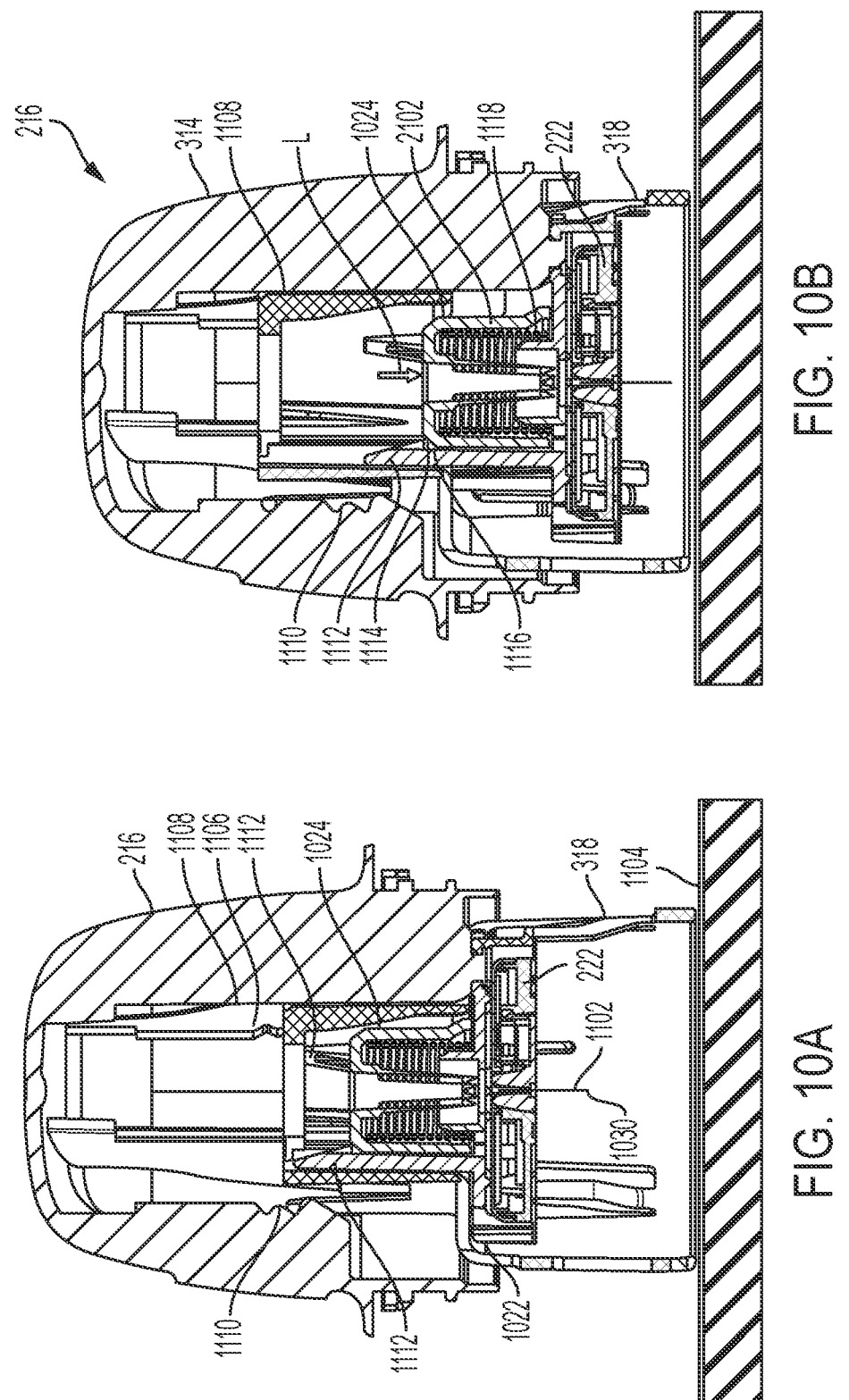
FIGS. 10A-10E illustrate cross-sectional views depicting an example embodiment of an applicator during various stages of deployment.

Referring to FIG. 6D, according to some embodiments, sharp carrier 201102 can also comprise one or more magnets 201102K for retaining a sensor control device in the sensor carrier (e.g., 710 or 20710 of FIGS. 5A-5D). By way of illustration, sharp carrier 201102 can comprise one or more magnets 201102K disposed in or on a distal-facing surface of sharp carrier 201102. According to one aspect of these embodiments, the one or more magnets 201102K are configured to attract one or more ferromagnetic components disposed in the sensor control device, which can cause the sensor control device to be retained in the sensor carrier when sharp carrier 201102 and sensor carrier are proximate to each other. More specifically, when sharp carrier 201102K and sensor carrier are coupled, as depicted in FIGS. 10A-10C, the one or more magnets 201102K are configured to generate a magnetic field having sufficient strength to exert a "pulling" force upon the ferromagnetic components disposed in the sensor control device in a proximal direction, such that the sensor control device is retained in the sensor carrier.

Figure 10D:
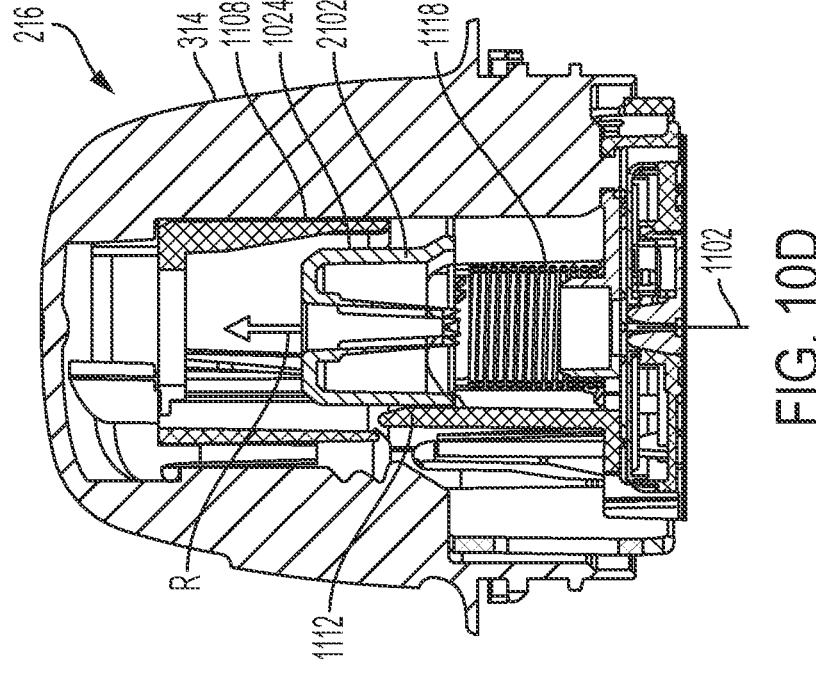
Figure 10C:
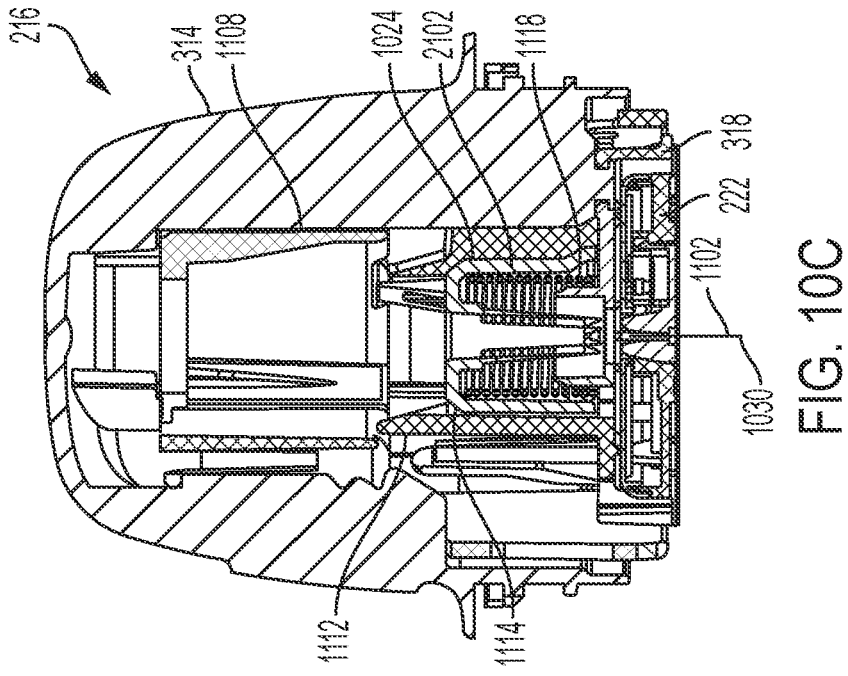
Figure 10E:
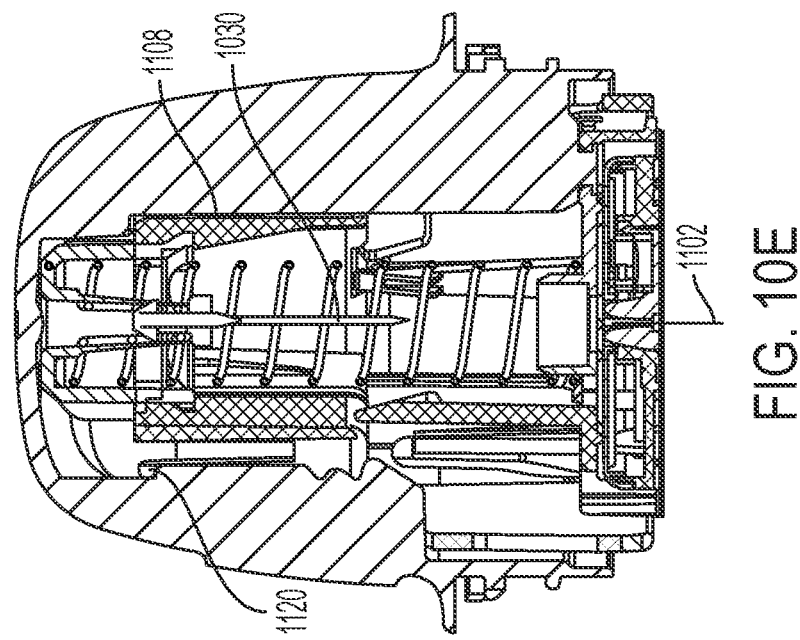

According to another aspect of the embodiments, as shown in FIG. 10E, the expansion of the return spring during the retraction of the sharp causes sharp carrier 201102 to separate from the sensor carrier and to be displaced in a proximal direction. As sharp carrier 201102 moves further away from the sensor carrier, the one or more magnets 201102K no longer exert a sufficient magnetic force to retain the sensor control device in the sensor carrier. Subsequently, the sensor control device can disengage from the sensor carrier.

According to some embodiments, the one or more magnets 201102K can be embedded in a distal end of the sharp carrier 201102 such that the distal-facing surface is flush against the sensor carrier. In some embodiments, the one or more magnets 201102K can comprise either a single magnetic element or a plurality of discrete magnetic elements. For example, in some embodiments, the one or more magnets 201102K can comprise a single magnetic element having an annular geometry. In other embodiments, the one or more magnets 201102K can comprise two, three, four, five or more discrete magnetic elements disposed upon distal facing surface of sharp carrier 201102. In still other embodiments, at least a portion of the distal end of sharp carrier 201102 itself can be constructed from a magnetic material. Those of skill in the art will appreciate that other configurations and geometries for implementing the one or more magnets for retaining a sensor control device in the sensor carrier are possible and fully within the scope of the present disclosure.

Exemplary Sensor and Connector Assemblies

Figure 7:
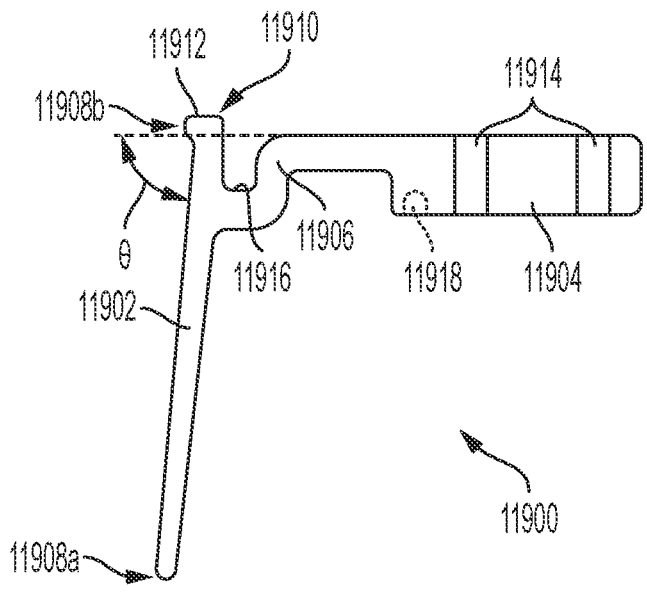
FIG. 7 is a side view of an exemplary sensor according to one or more embodiments of the disclosure.

FIG. 7 is a side view of an example sensor 11900, according to one or more embodiments of the disclosure. The sensor 11900 may be similar in some respects to any of the sensors described herein and, therefore, may be used in an analyte monitoring system to detect specific analyte concentrations. As illustrated, the sensor 11900 includes a tail 11902, a flag 11904, and a neck 11906 that interconnects the tail 11902 and the flag 11904. The tail 11902 includes an enzyme or other chemistry or biologic and, in some embodiments, a membrane may cover the chemistry. In use, the tail 11902 is transcutaneously received beneath a user's skin, and the chemistry included thereon helps facilitate analyte monitoring in the presence of bodily fluids.

The tail 11902 may be received within a hollow or recessed portion of a sharp (not shown) to at least partially circumscribe the tail 11902 of the sensor 11900. As illustrated, the tail 11902 may extend at an angle Q offset from horizontal. In some embodiments, the angle Q may be about 85°. Accordingly, in contrast to other sensor tails, the tail 11902 may not extend perpendicularly from the flag 11904, but instead at an angle offset from perpendicular. This may prove advantageous in helping maintain the tail 11902 within the recessed portion of the sharp.

The tail 11902 includes a first or bottom end 11908a and a second or top end 11908b opposite the bottom end 11908a. A tower 11910 may be provided at or near the top end 11908b and may extend vertically upward from the location where the neck 11906 interconnects the tail 11902 to the flag 11904. During operation, if the sharp moves laterally, the tower 11910 will help pivot the tail 11902 toward the sharp and otherwise stay within the recessed portion of the sharp. Moreover, in some embodiments, the tower 11910 may provide or otherwise define a protrusion 11912 that extends laterally therefrom. When the sensor 11900 is mated with the sharp and the tail 11902 extends within the recessed portion of the sharp, the protrusion 11912 may engage the inner surface of the recessed portion. In operation, the protrusion 11912 may help keep the tail 11902 within the recessed portion.

The flag 11904 may comprise a generally planar surface having one or more sensor contacts 11914 arranged thereon. The sensor contact(s) 11914 may be configured to align with a corresponding number of compliant carbon impregnated polymer modules encapsulated within a connector.

In some embodiments, as illustrated, the neck 11906 may provide or otherwise define a dip or bend 11916 extending between the flag 11904 and the tail 11902. The bend 11916 may prove advantageous in adding flexibility to the sensor 11900 and helping prevent bending of the neck 11906.

In some embodiments, a notch 11918 (shown in dashed lines) may optionally be defined in the flag near the neck 11906. The notch 11918 may add flexibility and tolerance to the sensor 11900 as the sensor 11900 is mounted to the mount. More specifically, the notch 11918 may help take up interference forces that may occur as the sensor 11900 is mounted within the mount.

Figure 8A:
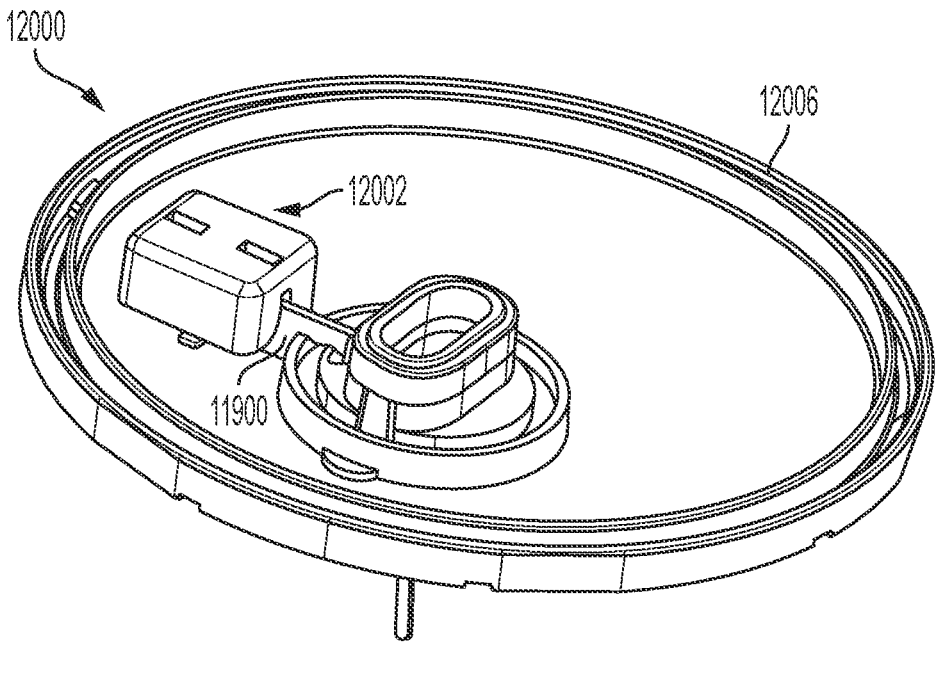

FIGS. 8A and 8B are isometric and partially exploded isometric views of an example connector assembly 12000, according to one or more embodiments. As illustrated, the connector assembly 12000 may include a connector 12002, and FIG. 8C is an isometric bottom view of the connector 12002. The connector 12002 may comprise an injection molded part used to help secure one or more compliant carbon impregnated polymer modules 12004 (four shown in FIG. 8B) to a mount 12006. More specifically, the connector 12002 may help secure the modules 12004 in place adjacent the sensor 11900 and in contact with the sensor contacts 11914 (FIG. 7C) provided on the flag 11904 (FIG. 7C). The modules 12004 may be made of a conductive material to provide conductive communication between the sensor

11900 and corresponding circuitry contacts (not shown) provided within the mount 12006.

As best seen in FIG. 8C, the connector 12002 may define pockets 12008 sized to receive the modules 12004. Moreover, in some embodiments, the connector 12002 may further define one or more depressions 12010 configured to mate with one or more corresponding flanges 12012 (FIG. 8B) on the mount 12006. Mating the depressions 12010 with the flanges 12012 may secure the connector 12002 to the mount 12006 via an interference fit or the like. In other embodiments, the connector 12002 may be secured to the mount 12006 using an adhesive or via sonic welding.

Figures 8E, 8F:
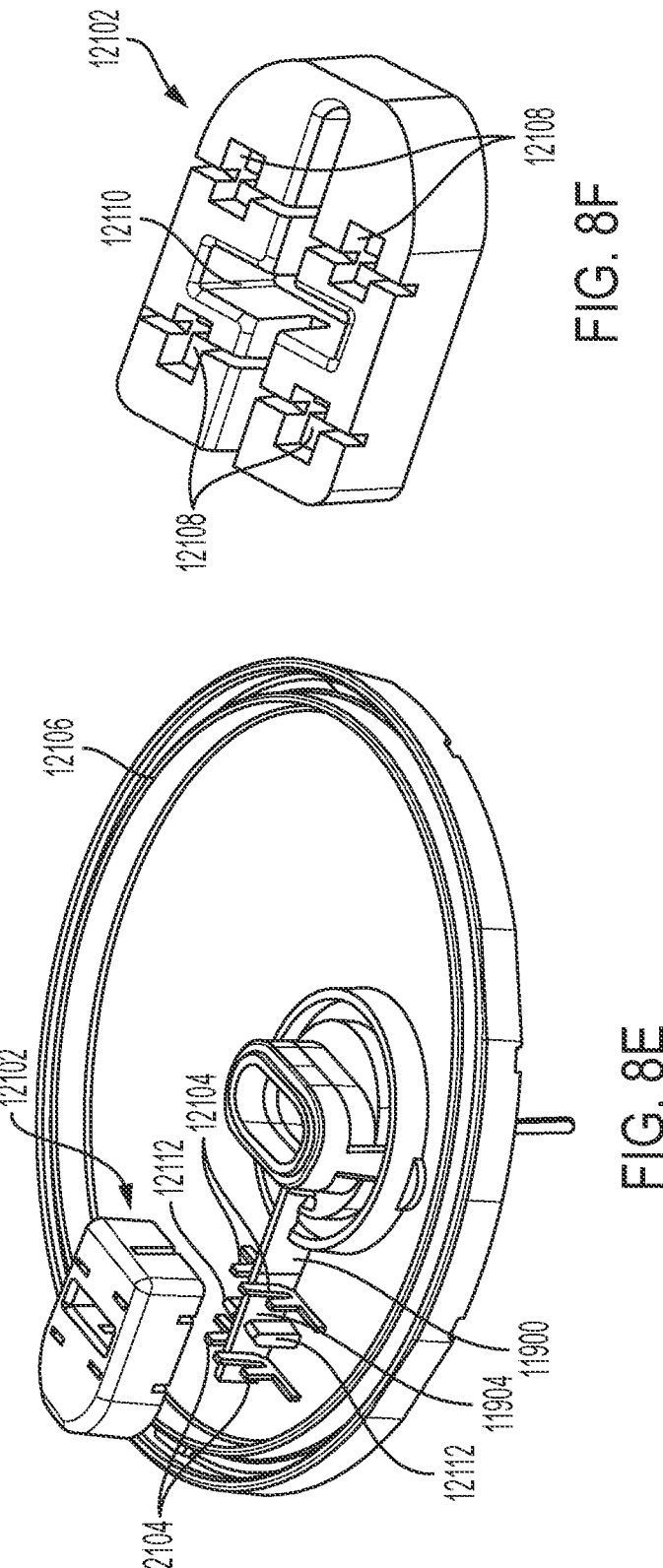

FIGS. 8D and 8E are isometric and partially exploded isometric views of another example connector assembly 12100, according to one or more embodiments. As illustrated, the connector assembly 12100 may include a connector 12102, and FIG. 8F is an isometric bottom view of the connector 12102. The connector 12102 may comprise an injection molded part used to help keep one or more compliant metal contacts 12104 (four shown in FIG. 8E) secured against the sensor 11900 on a mount 12106. More specifically, the connector 12102 may help secure the contacts 12104 in place adjacent the sensor 11900 and in contact with the sensor contacts 11914 (FIG. 7C) provided on the flag 11904. The contacts 12104 may be made of a stamped conductive material that provides conductive communication between the sensor 11900 and corresponding circuitry contacts (not shown) provided within the mount 12106. In some embodiments, for example, the contacts 12104 may be soldered to a PCB (not shown) arranged within the mount 12106.

As best seen in FIG. 8F, the connector 12102 may define pockets 12108 sized to receive the contacts 12104. Moreover, in some embodiments, the connector 12102 may further define one or more depressions 12110 configured to mate with one or more corresponding flanges 12112 on the mount 12006. Mating the depressions 12110 with the flanges 12112 may help secure the connector 12102 to the mount 12106 via an interference fit or the like. In other embodiments, the connector 12102 may be secured to the mount 12106 using an adhesive or via sonic welding.

In some embodiments, connector assembly (e.g., 12000 or 12100) can include a pull-tab (not shown) constructed from one or more electrically insulative materials configured to prolong the life of the battery and/or prevent current leakage during storage. According to some embodiments, for example, a first portion of the pull-tab can be removably engaged with sensor 11900 to prevent electrical coupling between sensor contacts 11914, on the one hand, and either of modules 12004 of FIG. 8B or contacts 12104 in FIG. 8E, on the other hand. Furthermore, in some embodiments, a second portion of the pull-tab can be coupled with the sharp or sharp carrier such that the pull-tab is disengaged from sensor 11900 when the applicator is actuated. In other embodiments, the second portion of the pull-tab can be coupled with the sharp or sharp carrier such that the pull-tab is disengaged from sensor 11900 during or after the retraction of the sharp.

According to other embodiments, a first portion of a pull-tab (not shown) can be removably engaged with the power supply (e.g., battery) to prevent electrical coupling between the power supply and the rest of the sensor electronics (e.g., PCB). In said embodiments, the second portion of the pull-tab can be coupled with the sharp or sharp carrier such that the pull-tab is disengaged from the power supply either when the applicator is actuated, or during (or after) the retraction of the sharp. In still other embodiments, a first portion of a pull-tab (not shown) can be removably engaged with any componentry of sensor electronics in the sensor control unit that would otherwise create a closed circuit with the power supply. Those of skill in the art will recognize that other configurations to preserve battery life and prevent current leakage during storage are possible, and are fully within the scope of the present disclosure.

Example Embodiments of Sensor Control Devices

Figure 9B:
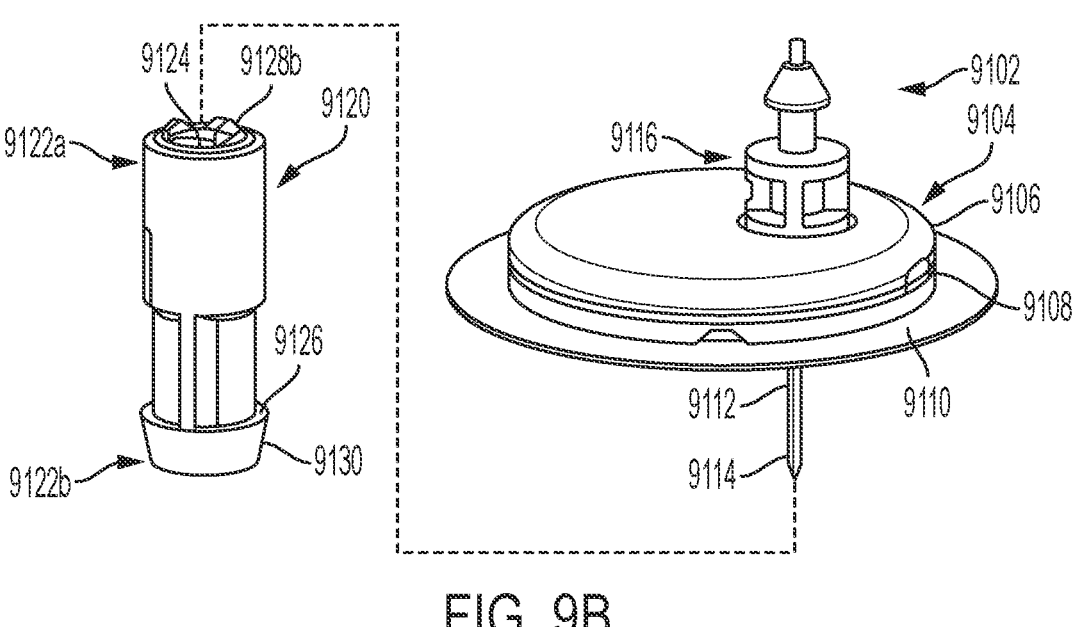

FIGS. 9A and 9B are side and isometric views, respectively, of an example sensor control device 9102, according to one or more embodiments of the present disclosure. The sensor control device 9102 may be similar in some respects to the sensor control device 102 of FIG. 1 and therefore may be best understood with reference thereto. Moreover, the sensor control device 9102 may replace the sensor control device 102 of FIG. 1 and, therefore, may be used in conjunction with the sensor applicator 102 of FIG. 1, which may deliver the sensor control device 9102 to a target monitoring location on a user's skin.

As illustrated, the sensor control device 9102 includes an electronics housing 9104, which may be generally disc-shaped and have a circular cross-section. In other embodiments, however, the electronics housing 9104 may exhibit other cross-sectional shapes, such as ovoid, oval, or polygonal, without departing from the scope of the disclosure. The electronics housing 9104 includes a shell 9106 and a mount 9108 that is mateable with the shell 9106. The shell 9106 may be secured to the mount 9108 via a variety of ways, such as a snap fit engagement, an interference fit, sonic welding, laser welding, one or more mechanical fasteners (e.g., screws), a gasket, an adhesive, or any combination thereof. In some cases, the shell 9106 may be secured to the mount 9108 such that a sealed interface is generated therebetween. An adhesive patch 9110 may be positioned on and otherwise attached to the underside of the mount 9108. According to an aspect of the embodiments, the adhesive patch 9110 (shown in FIG. 9A in non-hatched shading) may be configured to secure and maintain the sensor control device 9102 in position on the user's skin during operation.

The sensor control device 9102 may further include a sensor 9112 and a sharp 9114 used to help deliver the sensor 9112 transcutaneously under a user's skin during application of the sensor control device 9102. Corresponding portions of the sensor 9112 and the sharp 9114 extend distally from the bottom of the electronics housing 9104 (e.g., the mount 9108). A sharp hub 9116 may be overmolded onto the sharp 9114 and configured to secure and carry the sharp 9114. As best seen in FIG. 9A, the sharp hub 9116 may include or otherwise define a mating member 9118. In assembling the sharp 9114 to the sensor control device 9102, the sharp 9114 may be advanced axially through the electronics housing 9104 until the sharp hub 9116 engages an upper surface of the electronics housing 9104 or an internal component thereof and the mating member 9118 extends distally from the bottom of the mount 9108. As described herein below, in at least one embodiment, the sharp hub 9116 may sealingly engage an upper portion of a seal overmolded onto the mount 9108. As the sharp 9114 penetrates the electronics housing 9104, the exposed portion of the sensor 9112 may be received within a hollow or recessed (arcuate) portion of the sharp 9114. The remaining portion of the sensor 9112 is arranged within the interior of the electronics housing 9104.

The sensor control device 9102 may further include a sensor cap 9120, shown detached from the electronics housing 9104 in FIGS. 9A-9B. The sensor cap 9120 may help provide a sealed barrier that surrounds and protects exposed portions of the sensor 9112 and the sharp 9114. As illustrated, the sensor cap 9120 may comprise a generally cylindrical body having a first end 9122a and a second end 9122b opposite the first end 9122a. The first end 9122a may be open to provide access into an inner chamber 9124 defined within the body. In contrast, the second end 9122b may be closed and may provide or otherwise define an engagement feature 9126. As described in more detail below, the engagement feature 9126 may help mate the sensor cap 9120 to an applicator cap of a sensor applicator (e.g., the sensor applicator 102 of FIG. 1), and may help remove the sensor cap 9120 from the sensor control device 9102 upon removing the sensor cap from the sensor applicator.

The sensor cap 9120 may be removably coupled to the electronics housing 9104 at or near the bottom of the mount 9108. More specifically, the sensor cap 9120 may be removably coupled to the mating member 9118, which extends distally from the bottom of the mount 9108. In at least one embodiment, for example, the mating member 9118 may define a set of external threads 9128a (FIG. 9A) mateable with a set of internal threads 9128b (FIG. 9B) defined within the inner chamber 9124 of the sensor cap 9120. In some embodiments, the external and internal threads 9128a,b may comprise a flat thread design (e.g., lack of helical curvature), but may alternatively comprise a helical threaded engagement. Accordingly, in at least one embodiment, the sensor cap 9120 may be threadably coupled to the sensor control device 9102 at the mating member 9118 of the sharp hub 9116. In other embodiments, the sensor cap 9120 may be removably coupled to the mating member 9118 via other types of engagements including, but not limited to, an interference or friction fit, or a frangible member or substance (e.g., wax, an adhesive, etc.) that may be broken with minimal separation force (e.g., axial or rotational force).

In some embodiments, the sensor cap 9120 may comprise a monolithic (singular) structure extending between the first and second ends 9122a,b. In other embodiments, however, the sensor cap 9120 may comprise two or more component parts. In the illustrated embodiment, for example, the body of the sensor cap 9120 may include a desiccant cap 9130 arranged at the second end 9122b. The desiccant cap 9130 may house or comprise a desiccant to help maintain preferred humidity levels within the inner chamber 9124. Moreover, the desiccant cap 9130 may also define or otherwise provide the engagement feature 9126 of the sensor cap 9120. In at least one embodiment, the desiccant cap 9130 may comprise an elastomeric plug inserted into the bottom end of the sensor cap 9120.

In some embodiments, sensor control device 9102 can also include an adhesive liner 9110B (shown in FIG. 9A in hatched shading) coupled with a bottom surface of adhesive patch 9110. Under certain conditions within the housing and cap of the applicator, chemical interactions between the adhesive patch 9110, trapped atmosphere, desiccant, and outgassing of materials can cause the adhesive to degrade during storage or shipment of the applicator. Applying liner 9110B can mitigate degradation of the adhesive of adhesive patch 9110. According to another aspect of the embodiments, liner 9110B can also be operatively coupled with sensor cap 9120 such that removal of sensor cap 9120 also causes removal of liner 9110B.

Exemplary Firing Mechanism of One-Piece and Two-Piece Applicators

FIGS. 10A-10E illustrate example details of embodiments of the internal device mechanics of "firing" the applicator 216 to apply sensor control device 222 to a user and including retracting sharp 1030 safely back into used applicator 216. All together, these drawings represent an example sequence of driving sharp 1030 (supporting a sensor coupled to sensor control device 222) into the skin of a user, withdrawing the sharp while leaving the sensor behind in operative contact with interstitial fluid of the user, and adhering the sensor control device to the skin of the user with an adhesive. Modification of such activity for use with the alternative applicator assembly embodiments and components can be appreciated in reference to the same by those with skill in the art. Moreover, applicator 216 may be a sensor applicator having one-piece architecture or a two-piece architecture as disclosed herein.

Turning now to FIG. 10A, a sensor 1102 is supported within sharp 1030, just above the skin 1104 of the user. Rails 1106 (optionally three of them) of an upper guide section 1108 may be provided to control applicator 216 motion relative to sheath 318. The sheath 318 is held by detent features 1110 within the applicator 216 such that appropriate downward force along the longitudinal axis of the applicator 216 will cause the resistance provided by the detent features 1110 to be overcome so that sharp 1030 and sensor control device 222 can translate along the longitudinal axis into (and onto) skin 1104 of the user. In addition, catch arms 1112 of sensor carrier 1022 engage the sharp retraction assembly 1024 to maintain the sharp 1030 in a position relative to the sensor control device 222.

In FIG. 10B, user force is applied to overcome or override detent features 1110 and sheath 318 collapses into housing 314 driving the sensor control device 222 (with associated parts) to translate down as indicated by the arrow L along the longitudinal axis. An inner diameter of the upper guide section 1108 of the sheath 318 constrains the position of carrier arms 1112 through the full stroke of the sensor/sharp insertion process. The retention of the stop surfaces 1114 of carrier arms 1112 against the complimentary faces 1116 of the sharp retraction assembly 1024 maintains the position of the members with return spring 1118 fully energized.

In FIG. 10C, sensor 1102 and sharp 1030 have reached full insertion depth. In so doing, the carrier arms 1112 clear the upper guide section 1108 inner diameter. Then, the compressed force of the coil return spring 1118 drives angled stop surfaces 1114 radially outward, releasing force to drive the sharp carrier 2102 of the sharp retraction assembly 1024 to pull the (slotted or otherwise configured) sharp 1030 out of the user and off of the sensor 1102 as indicated by the arrow R in FIG. 10D.

With the sharp 1030 fully retracted as shown in FIG. 10E, the upper guide section 1108 of the sheath 318 is set with a final locking feature 1120. Subsequently, the spent applicator assembly 216 is removed from the insertion site, leaving behind the sensor control device 222, and with the sharp 1030 secured safely inside the applicator assembly 216. The spent applicator assembly 216 is now ready for disposal.

Operation of the applicator 216 when applying the sensor control device 222 is designed to provide the user with a sensation that both the insertion and retraction of the sharp 1030 is performed automatically by the internal mechanisms of the applicator 216. In other words, the present invention avoids the user experiencing the sensation that he is manually driving the sharp 1030 into his skin. Thus, once the user applies sufficient force to overcome the resistance from the detent features of the applicator 216, the resulting actions of the applicator 216 are perceived to be an automated response to the applicator being "triggered." The user does not perceive that he is supplying additional force to drive the sharp 1030 to pierce his skin despite that all the driving force is provided by the user and no additional biasing/driving means are used to insert the sharp 1030. As detailed above in FIG. 10C, the retraction of the sharp 1030 is automated by the coil return spring 1118 of the applicator 216.

Figure 11A:
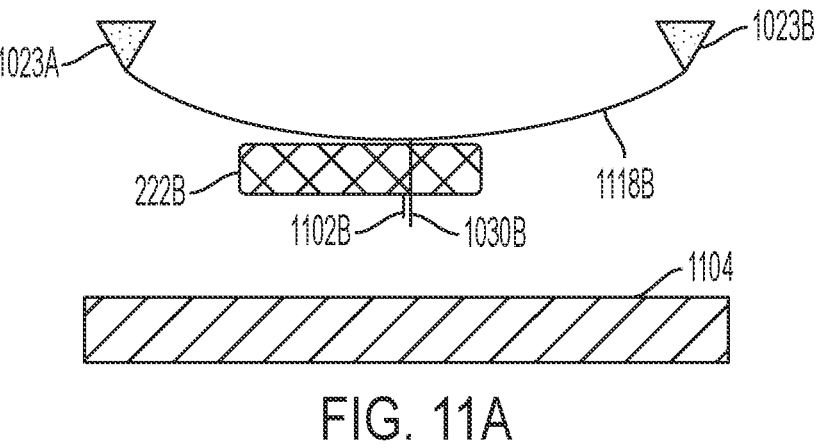
FIGS. 11A-11C are side views of a leaf spring and sharp assembly according to one or more embodiments of the present disclosure.
Figure 11B:
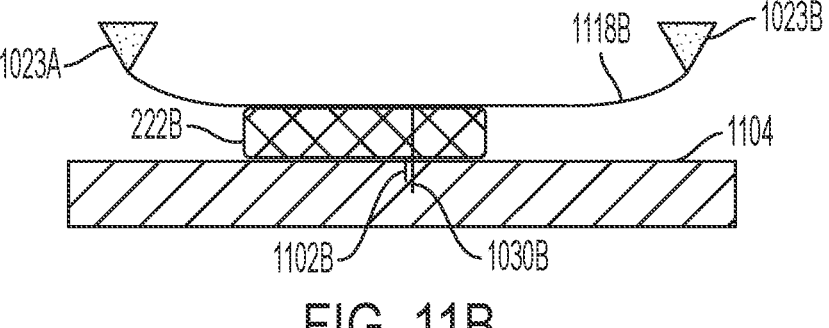
Figure 11C:
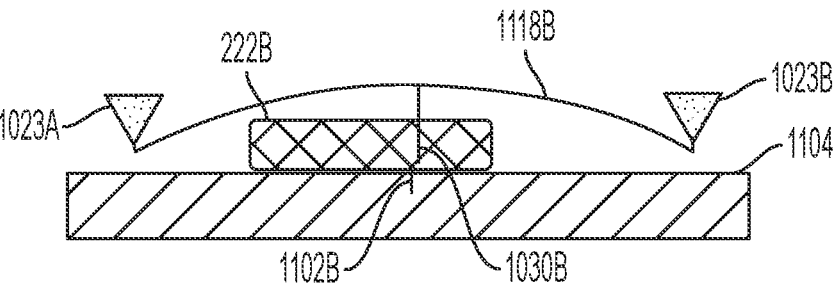

FIGS. 11A-11C depict an alternative embodiment of a spring-biased retraction mechanism for implementation in a sensor applicator device. According to one aspect of some embodiments, in order to reduce the number of components in a sensor applicator (and reduce the number of potential mechanical failures), a leaf spring 1118B can be employed in a sensor applicator, such as applicator 216 of FIGS. 10A-10E, in place of a coiled return spring 1118.

Referring first to FIG. 11A, a partial cross-sectional side view of certain sensor applicator components, according to some embodiments, is shown in a pre-firing stage (similar to FIG. 10A). In particular, FIG. 11A depicts leaf spring 1118B coupled with sharp 1030B, wherein sharp 1030B is in a spaced relation with the skin surface 1104. As further shown in FIG. 11A, leaf spring 1118B is depicted in a first state in which a distal facing surface of leaf spring 1118B is in a convex configuration relative to skin surface 1104.

According to some embodiments, sharp 1030B can be coupled with a center portion of leaf spring 1118B by an interference fit, sonic welding, laser welding, one or more mechanical fasteners (e.g., screws), a gasket, an adhesive, or any combination thereof. In some embodiments, leaf spring 1118B can be constructed from the same material (e.g., stainless steel) as sharp 1030B. In other embodiments, leaf spring 1118B can be constructed from a first material (e.g., stainless steel) having a first stiffness, and sharp 1030B can be constructed from a second material (e.g., plastic) having a second stiffness different than the first stiffness. According to another aspect of some embodiments, like the embodiment depicted in FIG. 10A, sharp 1030B can extend through sensor control device 222B, and a portion of glucose sensor 1102B can be coupled with, or partially disposed within, a distal portion of sharp 1030B.

According to another aspect of some embodiments, a plurality of engagement features 1023A, 1023B are configured to affix leaf spring 1118B with either sensor carrier (not shown) or a sharp retraction assembly (not shown), such that the downward movement of the housing, sensor carrier and sharp retraction assembly will also cause at least the edge portions of leaf spring 1118B to move in the distal direction.

FIG. 11B is another partial cross-sectional side view of the aforementioned sensor applicator components, according to some embodiments, wherein the applicator is depicted in an insertion stage (similar to FIG. 10C). In particular, FIG. 11B shows sharp 1030B after it has pierced skin surface 1104, and sensor 1102B has reached a predetermined insertion depth. According to an aspect of some embodiments, at the insertion stage, the adhesive pad (not shown) on the bottom surface of sensor control device 222B is adhered to skin surface 1104.

As can be further seen in FIG. 11B, leaf spring 1118B is depicted in a second state in which the surface of leaf spring 1118B has been transformed from a convex configuration (relative to skin surface 1104) to a substantially planar configuration, as the housing, sensor carrier, and sharp retraction assembly (not shown) of the applicator continue to advance in a distal direction. In some embodiments, the substantially planar surface of leaf spring 1118B can also be configured to apply a force in a distal direction against either the sensor control device 222B or the sensor carrier (not shown).

FIG. 11C is another partial cross-section side view of the aforementioned applicator components, according to some embodiments, wherein the applicator is shown in a retraction stage (similar to FIGS. 10D and 10E). In particular, as the housing (not shown) of the applicator is further displaced in the distal direction, leaf spring 1118B is depicted in a third state in which the surface of leaf spring 1118B has reached or exceeded a deformation threshold level such that the leaf spring 1118B "snaps" into a concave configuration relative skin surface 1104. As a result of the concave configuration, according to an aspect of some embodiments, sharp 1030B is retracted in a proximal direction away from skin surface 1104, while leaving behind sensor 1102B under skin surface 1104. In some embodiments, the concave configuration can also cause leaf spring 1118B to disengage from sensor control device 222B.

Subsequently, according to some embodiments, the applicator can be removed from the insertion site, leaving behind the sensor control device 222B, and with the sharp 1030B secured safely inside the applicator assembly. The applicator assembly can now be disposed of.

With respect to any of the applicator embodiments described herein, as well as any of the components thereof, including but not limited to the sharp, sharp module and sensor module embodiments, those of skill in the art will understand that said embodiments can be dimensioned and configured for use with sensors configured to sense an analyte level in a bodily fluid in the epidermis, dermis, or subcutaneous tissue of a subject. In some embodiments, for example, sharps and distal portions of analyte sensors disclosed herein can both be dimensioned and configured to be positioned at a particular end-depth (i.e., the furthest point of penetration in a tissue or layer of the subject's body, e.g., in the epidermis, dermis, or subcutaneous tissue). With respect to some applicator embodiments, those of skill in the art will appreciate that certain embodiments of sharps can be dimensioned and configured to be positioned at a different end-depth in the subject's body relative to the final end-depth of the analyte sensor. In some embodiments, for example, a sharp can be positioned at a first end-depth in the subject's epidermis prior to retraction, while a distal portion of an analyte sensor can be positioned at a second end-depth in the subject's dermis. In other embodiments, a sharp can be positioned at a first end-depth in the subject's dermis prior to retraction, while a distal portion of an analyte sensor can be positioned at a second end-depth in the subject's subcutaneous tissue. In still other embodiments, a sharp can be positioned at a first end-depth prior to retraction and the analyte sensor can be positioned at a second end-depth, wherein the first end-depth and second end-depths are both in the same layer or tissue of the subject's body.

Additionally, with respect to any of the applicator embodiments described herein, those of skill in the art will understand that an analyte sensor, as well as one or more structural components coupled thereto, including but not limited to one or more spring-mechanisms, can be disposed within the applicator in an off-center position relative to one or more axes of the applicator. In some applicator embodiments, for example, an analyte sensor and a spring mechanism can be disposed in a first off-center position relative to an axis of the applicator on a first side of the applicator, and the sensor electronics can be disposed in a second off-center position relative to the axis of the applicator on a second side of the applicator. In other applicator embodiments, the analyte sensor, spring mechanism, and sensor electronics can be disposed in an off-center position relative to an axis of the applicator on the same side. Those of skill in the art will appreciate that other permutations and configurations in which any or all of the analyte sensor, spring mechanism, sensor electronics, and other components of the applicator are disposed in a centered or off-centered position relative to one or more axes of the applicator are possible and fully within the scope of the present disclosure.

A number of deflectable structures are described herein, including but not limited to deflectable detent snaps, deflectable locking arms, sharp carrier lock arms, sharp retention arms, and module snaps. These deflectable structures are composed of a resilient material such as plastic or metal (or others) and operate in a manner well known to those of ordinary skill in the art. The deflectable structures each has a resting state or position that the resilient material is biased towards. If a force is applied that causes the structure to deflect or move from this resting state or position, then the bias of the resilient material will cause the structure to return to the resting state or position once the force is removed (or lessened). In many instances these structures are configured as arms with detents, or snaps, but other structures or configurations can be used that retain the same characteristics of deflectability and ability to return to a resting position, including but not limited to a leg, a clip, a catch, an abutment on a deflectable member, and the like.

Additional details of suitable devices, systems, methods, components and the operation thereof along with related features are set forth in International Publication No. WO2018/136898 to Rao et. al., International Publication No. WO2019/236850 to Thomas et. al., International Publication No. WO2019/236859 to Thomas et. al., International Publication No. WO2019/236876 to Thomas et. al., and U.S. Patent Publication No. 2020/0196919, filed Jun. 6, 2019, each of which is incorporated by reference in its entirety herein. Further details regarding embodiments of applicators, their components, and variants thereof, are described in U.S. Patent Publication Nos. 2012/0197222, 2013/0150691, 2016/0128615, 2016/0331283, 2018/0235520, 2019/0298240, and 2020/0397356 all of which are incorporated by reference herein in their entireties and for all purposes. Further details regarding embodiments of sharp modules, sharps, their components, and variants thereof, are described in U.S. Patent Publication No. 2014/0171771, which is incorporated by reference herein in its entirety and for all purposes.

Exemplary embodiments and features are set out in the following numbered clauses:

1. A sensor applicator assembly comprising:
a housing configured to move between a first position and a second position;
a sheath slidably coupled with the housing; and
a sensor carrier coupled with the housing;
an applicator cap threadably coupled with the housing, wherein the applicator cap and the housing define an interior space, and wherein the interior space comprises a lightly pressurized inert gas.
2. The sensor applicator assembly of clause 1, wherein the housing comprises an applicator cap sealing lip configured to interface with the applicator cap.
3. The sensor applicator assembly of clause 2, wherein the applicator cap includes a seal interface configured to receive the applicator cap sealing lip of the housing.
4. The sensor applicator assembly of clause 3, wherein the seal interface and the applicator cap sealing lip are configured to form a seal between the housing and the applicator cap.
5. The sensor applicator assembly of clause 4, wherein the seal further comprises a gasket.
6. The sensor applicator assembly of clause 4 or 5, wherein the lightly pressurized inert gas creates an outwardly biased flow across the seal.

7. The sensor applicator assembly of any of clauses 1 to 6, wherein the lightly pressurized gas comprises nitrogen.

8. The sensor applicator assembly of any of clauses 1 to 7, wherein the applicator cap is configured to retain a desiccant.

9. The sensor applicator assembly of any of clauses 1 to 8, wherein the applicator cap does not include a desiccant.

10. The sensor applicator assembly of any of clauses 1 to 9, wherein the interior space comprises a first pressure, and wherein an exterior space external to the sensor applicator assembly comprises a second pressure that is less than the first pressure.

11. A sensor applicator assembly comprising:
  a housing configured to move between a first position and a second position;
  a sheath slidably coupled with the housing;
  a sharp carrier comprising one or more magnets;
  a sensor control device comprising an analyte sensor, sensor electronics, and one or more ferromagnetic components; and
  a sensor carrier configured to retain the sensor control device,
    wherein the one or more magnets are configured to exert a magnetic force upon the ferromagnetic components in a proximate direction, such that the sensor control device is retained in the sensor carrier when the housing is in the first position.

12. The sensor applicator assembly of clause 11, wherein the one or more ferromagnetic components are disposed in the sensor control device.

13. The sensor applicator assembly of clause 11 or 12, wherein the one or more ferromagnetic components are embedded in a housing of the sensor control device.

14. The sensor applicator assembly of any of clauses 11 to 13, wherein the sensor carrier is configured to retain the sensor control device by magnetic force only.

15. The sensor applicator assembly of any of clauses 11 to 14, wherein the one or more magnets are disposed on a distal-facing surface of the sharp carrier.

16. The sensor applicator assembly of any of clauses 11 to 15, wherein the one or more magnets are embedded in a distal end of the sharp carrier.

17. The sensor applicator assembly of any of clauses 11 to 16, wherein the one or more magnets comprise a single magnetic element.

18. The sensor applicator assembly of clause 17, wherein the single magnetic element comprises an annular geometry.

19. The sensor applicator assembly of clauses 11 to 18, wherein at least a portion of a distal end of the sharp carrier comprises a magnetic material.

20. The sensor applicator assembly of clauses 11 to 16, wherein the one or more magnets comprises two magnetic elements disposed upon a distal facing surface of the sharp carrier.

21. The sensor applicator assembly of clauses 11 to 16, wherein the one or more magnets comprises three magnetic elements disposed upon a distal facing surface of the sharp carrier.

22. The sensor applicator assembly of clauses 11 to 21, further comprising a return spring.

23. The sensor applicator assembly of clause 22, wherein the return spring is configured to expand and move the sharp carrier in a proximate direction after the housing has reached the second position.

24. The sensor applicator assembly of clause 23, wherein the one or more magnets are configured such that the magnetic force exerted upon the ferromagnetic components is not sufficient to retain the sensor control device in the sensor carrier after the sharp carrier has moved in the proximate direction.

25. The sensor applicator assembly of clause 24, wherein the sensor control device is configured to disengage from the sensor carrier after the sharp carrier has moved in the proximate direction.

26. A sensor applicator assembly comprising:
  a housing configured to move between a first position and a second position;
  a sheath slidably coupled with the housing;
  a sharp carrier coupled with a sharp;
  a sensor control device comprising:
  an analyte sensor comprising a plurality of sensor contacts,
  a connector assembly comprising one or more of a plurality of sensor modules or a plurality of connector contacts, the connector assembly configured to couple with the analyte sensor, and a power supply; and
  a sensor carrier configured to retain the sensor control device,
  wherein the connector assembly further comprises a pull-tab comprising an electrically insulative material.

27. The sensor applicator assembly of clause 26, wherein the pull-tab comprises a first portion removably engaged with the plurality of sensor contacts.

28. The sensor applicator assembly of clause 27, wherein the first portion of the pull-tab is configured to prevent electrical coupling between the sensor contacts and the plurality of sensor modules.

29. The sensor applicator assembly of clause 27, wherein the first portion of the pull-tab is configured to prevent electrical coupling between the sensor contacts and the plurality of connector contacts.

30. The sensor applicator assembly of any of clauses 27 to 29, wherein the pull-tab comprises a second portion coupled with the sharp or the sharp carrier.

31. The sensor applicator assembly of clause 30, wherein the pull-tab is configured to disengage from the plurality of sensor contacts by movement of the sharp or the sharp carrier when the sensor applicator assembly is actuated.

32. The sensor applicator assembly of clause 30, wherein the pull-tab is configured to disengage from the plurality of sensor contacts when the sharp or the sharp carrier is retracted within the sensor applicator assembly.

33. A sensor applicator assembly comprising:
  a housing configured to move between a first position and a second position;
  a sheath slidably coupled with the housing;
  a sharp carrier coupled with a sharp;
  a sensor control device comprising:
  an analyte sensor comprising a plurality of sensor contacts,
  a connector assembly configured to couple with the analyte sensor, and
  a power supply; and
  a sensor carrier configured to retain the sensor control device,
  wherein the sensor control device further comprises a pull-tab coupled with the power supply,
  wherein the pull-tab comprises an electrically insulative material.

34. The sensor applicator assembly of clause 33, wherein the power supply is a coin cell battery.

35. The sensor applicator assembly of clause 33 or 34, wherein the pull-tab comprises a first portion removably engaged with the power supply.

36. The sensor applicator assembly of clause 35, wherein the first portion of the pull-tab is configured to prevent electrical coupling between the power supply and sensor electronics of the sensor control device.

37. The sensor applicator assembly of clause 35 or 36, wherein the pull-tab comprises a second portion coupled with the sharp or the sharp carrier.

38. The sensor applicator assembly of clause 37, wherein the pull-tab is configured to disengage from the power supply by movement of the sharp or the sharp carrier when the sensor applicator assembly is actuated.

39. The sensor applicator assembly of clause 37, wherein the pull-tab is configured to disengage from the power supply when the sharp or the sharp carrier is retracted within the sensor applicator assembly.

40. A sensor applicator assembly comprising:
a housing configured to move between a first position and a second position;
a sheath slidably coupled with the housing;
a sharp carrier coupled with a sharp;
a sensor control device comprising:
an electronics housing,
sensor electronics disposed within the electronics housing,
an analyte sensor coupled with the sensor electronics,
an adhesive patch disposed on a bottom surface of the electronics housing, and
an adhesive liner coupled with a bottom surface of the adhesive patch; and
a sensor carrier configured to retain the sensor control device; and
a sensor cap removably coupled with the sensor control device.

41. The sensor applicator assembly of clause 40, wherein adhesive liner is operatively coupled with the sensor cap such that removal of the sensor cap causes removal of the adhesive liner.

42. A sensor applicator assembly of clause 41, further comprising an applicator cap threadably coupled with the housing, wherein the applicator cap is configured to remove the sensor cap from the sensor applicator assembly when the applicator cap is decoupled from the housing.

43. The applicator assembly of clause 41 or 42,
wherein the sensor control device comprises a first aperture on a top surface of the electronics housing,
wherein the sensor control device comprises a second aperture on the bottom surface of the electronics housing,
wherein the adhesive patch comprises a third aperture,
wherein the adhesive liner comprises a fourth aperture, and
wherein the sharp extends through the first, second, third, and fourth apertures when the housing is in the first position.

44. A sensor applicator assembly comprising:
a housing configured to move between a first position and a second position;
a sheath slidably coupled with the housing, wherein a distal end of the sheath is configured to be placed against a skin surface;
a leaf spring coupled with a sharp;
a sensor control device comprising an analyte sensor coupled with sensor electronics; and
a sensor carrier configured to retain the sensor control device when the housing is in the first position,
wherein the sharp is configured to position at least a portion of the analyte sensor under the skin surface when the housing is moved to the second position, and wherein the leaf spring is configured to retract the sharp into the sensor applicator assembly after the housing is moved to the second position.

45. The sensor applicator assembly of clause 44, wherein the leaf spring comprises a convex configuration relative to the skin surface when the housing is in the first position.

46. The sensor applicator assembly of clause 44 or 45, wherein the leaf spring is configured to deform while the housing is moving between the first position and the second position.

47. The sensor applicator assembly of any of clauses 44 to 46, wherein the leaf spring comprises a substantially planar configuration relative to the skin surface before the sharp is retracted into the sensor applicator assembly.

48. The sensor applicator assembly of any of clauses 44 to 47, wherein the sensor control device is configured to be adhere to the skin surface when the housing is moved to the second position, and
wherein the leaf spring comprises a substantially planar configuration relative to the skin surface when the sensor control device is adhered to the skin surface.

49. The sensor applicator assembly of any of clauses 44 to 48, wherein the leaf spring comprises a concave configuration relative to the skin surface after the sharp is retracted into the sensor applicator assembly.

50. The sensor applicator assembly of any of clauses 44 to 49, wherein the leaf spring is coupled to the sharp by an interference fit.

51. The sensor applicator assembly of any of clauses 44 to 49, wherein the leaf spring is coupled to the sharp by sonic welding.

52. The sensor applicator assembly of any of clauses 44 to 49, wherein the leaf spring is coupled to the sharp by laser welding.

53. The sensor applicator assembly of any of clauses 44 to 49, wherein the leaf spring is coupled to the sharp by one or more mechanical fasteners.

54. The sensor applicator assembly of any of clauses 44 to 53, wherein the leaf spring comprises a first material, and the sharp comprises a second material different from the first material.

55. The sensor applicator assembly of any of clauses 44 to 53, wherein the leaf spring and the sharp comprise a stainless steel material.

56. The sensor applicator assembly of any of clauses 44 to 55, wherein the leaf spring comprises a first stiffness, and wherein the sharp comprises a second stiffness different than the first stiffness.

57. The sensor applicator assembly of any of clauses 44 to 56, further comprising a plurality of engagement features configured to affix the leaf spring with the sensor carrier.

58. The sensor applicator assembly of any of clauses 44 to 56, further comprising a plurality of engagement features configured to affix the leaf spring with the sharp carrier.

59. The sensor applicator assembly of any of clauses 44 to 58, wherein the leaf spring is further configured to apply a force in a distal direction against the sensor control device.

60. The sensor applicator assembly of any of clauses 44 to 59, wherein the leaf spring is further configured to apply a force in a distal direction against the sensor carrier.

61. A method for introducing an inert gas into a sensor applicator assembly comprising a housing and a cap, the method comprising:
placing the sensor applicator assembly into a closed system while the closed system is at a first predetermined temperature, wherein at the first predetermined temperature, the housing and the cap form a seal;

heating the closed system from the first predetermined temperature to a second predetermined temperature, wherein at the second predetermined temperature, a thermal expansion of the cap causes the cap to unseal from the housing;

diffusing the inert gas into an interior of the sensor applicator assembly; and cooling the closed system from the second predetermined temperature to a third predetermined temperature, wherein at the third predetermined temperature, contraction of the cap causes the cap to form the seal with the housing.

62. The method of clause 61, wherein the inert gas is argon.

63. The method of clause 61 or 62, wherein the first predetermined temperature is equal to the third predetermined temperature.

64. The method of any of clauses 61 to 63, wherein diffusing the inert gas into the interior of the sensor applicator assembly includes maintaining the closed system at the second predetermined temperature for a predetermined period of time.

65. The method of any of clauses 61 to 64, further comprising introducing the inert gas into the closed system before placing the sensor applicator assembly therein.

66. The method of any of clauses 61 to 64, further comprising introducing the inert gas into the closed system after placing the sensor applicator assembly therein.

67. A sensor applicator assembly comprising:

a housing configured to move between a first position and a second position;

a sheath slidably coupled with the housing;

a sensor control device comprising an analyte sensor, sensor electronics, and one or more ferromagnetic components; and a sensor carrier comprising one or more magnets, the sensor carrier configured to retain the sensor control device, wherein the one or more magnets are configured to exert a magnetic force upon the ferromagnetic components in a proximate direction, such that the sensor control device is retained in the sensor carrier when the housing is in the first position.

68. The sensor applicator assembly of clause 67, wherein the one or more ferromagnetic components are disposed in the sensor control device.

69. The sensor applicator assembly of clause 67 or 68, wherein the sensor control device further comprises an adhesive patch.

70. The sensor applicator assembly of clause 69, wherein the adhesive patch, when coupled with a skin surface, creates an adhesive force greater than the magnetic force.

71. The sensor applicator assembly of clause 70, wherein the adhesive patch is configured such that the adhesive force causes the sensor control device to disengage from the sensor carrier when the sensor control device is adhered to the skin.

72. A sensor applicator assembly comprising:

a housing comprising an interior;

a sensor carrier configured to retain a sensor control device and to move between a first position and a second position within the interior of the housing, wherein the sensor carrier comprises a magnet;

the sensor control device comprising a glucose sensor coupled with sensor electronics, the wherein the sensor control device is disposed within the interior of the housing when the sensor carrier is in the first position.

73. The sensor applicator assembly of clause 72, further comprising a sharp carrier, a sharp, and a return spring.

74. The sensor applicator assembly of clause 73, wherein the return spring is configured to expand and move the sharp carrier in a proximate direction.

75. The sensor control assembly of clause 72, wherein the magnet engages at least a portion of the sensor control device.

76. The sensor control assembly of clause 72, wherein the sensor control device comprises a material responsive to a magnetic field created by the magnet of the sensor carrier.

77. The sensor control assembly of clause 72, wherein the sensor control device further comprises an adhesive patch disposed on a bottom surface of the sensor control device.

The description encompasses and expressly envisages methods that are non-surgical, non-invasive methods implemented outside the body. The methods are typically implemented by a user who is not required to be a medical professional.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Thus, the foregoing description of specific embodiments of the disclosed subject matter has been presented for purposes of illustration and description. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents. Furthermore, any features, functions, steps, or elements of the embodiments may be recited in or added to the claims, as well as negative limitations that define the inventive scope of the claims by features, functions, steps, or elements that are not within that scope.

The invention claimed is:

1. An assembly for insertion of a glucose sensor in a subject's body, the assembly comprising:

(1) an applicator, comprising:

an applicator housing defining an interior;

a sheath slidably coupled with the applicator housing and comprising a distal end configured for placement on the skin;

a sharp carrier assembly coupled with a sharp;

a sensor carrier comprising a cavity formed by a proximal wall and a side wall comprising a magnetic component, the cavity configured to retain a sensor control device therein;

a spring, comprising a distal end in contact with the sensor carrier; and a cap configured to threadably couple with a distal part of the applicator housing;

(2) the sensor control device configured to be worn on the subject's body, the sensor control device comprising:

an adhesive patch disposed on a bottom surface of the sensor control device and configured to adhere the sensor control device to the subject's skin;

the glucose sensor comprising:

a proximal portion configured to electrically couple with electronics;

a distal portion having a glucose-responsive enzyme, wherein the distal portion is configured to be positioned in a bodily fluid of the subject's body and to sense glucose in the subject's bodily fluid in a subcutaneous layer; and the electronics comprising one or more processors, a memory, and communication circuitry configured to wirelessly transmit data according to a Bluetooth Low Energy protocol, wherein the sharp carrier assembly, the sharp, the spring, the sensor carrier, the magnet, and the sensor control device are configured to advance a distance within the interior of the applicator housing, relative to the sheath, and in a linear direction from a proximal position to a distal position, wherein, in the proximal position, the distal end of the glucose sensor is received in a portion of the sharp, wherein the magnetic component is configured to exert a magnetic force upon one or more ferromagnetic components of the sensor control device when the sensor carrier and the sensor control device are in the proximal position, and wherein, in the distal position, the sensor control device is configured to adhere to the subject's skin via the adhesive patch, disengage from the sensor carrier, and increase a spaced relation with the magnetic component.

2. The assembly of claim 1, wherein the sensor control device further comprises a housing of the sensor control device defining an interior of the sensor control device, and wherein the one or more ferromagnetic components are disposed in the interior of the sensor control device.

3. The assembly of claim 2, wherein an adhesive force created by an adhesive property of the adhesive patch is greater than the magnetic force exerted by the magnetic component upon the one or more ferromagnetic components.

4. The assembly of claim 3, wherein the sensor control device is configured to disengage from the sensor carrier when the subject pulls the applicator away from the subject's skin.

5. The assembly of claim 4, wherein the spring is configured to retract the sharp carrier assembly and the sharp in a proximal direction into the applicator after the sharp carrier assembly, the sharp, the spring, the sensor carrier, the magnetic component, and the sensor control device reach the distal position.

6. The assembly of claim 4, wherein the subcutaneous glucose sensor further comprises a proximal portion including one or more electrical contacts.

7. The assembly of claim 6, wherein the subcutaneous glucose sensor further comprises a bent portion between the proximal portion of the subcutaneous glucose sensor and the distal portion of the subcutaneous glucose sensor.

8. The assembly of claim 7, wherein the proximal portion of the subcutaneous glucose sensor is perpendicular to the distal portion of the subcutaneous glucose sensor.

9. The assembly of claim 8, wherein the applicator further comprises a gasket configured to create a seal between the applicator housing and the cap.

10. The assembly of claim 9, wherein the distal end of the subcutaneous glucose sensor and a distal portion of the sharp extend in a distal direction from the bottom surface of the sensor control device when the sharp carrier assembly, the sharp, the spring, the sensor carrier, the magnetic component, and the sensor control device are in the proximal position.

11. The assembly of claim 10, wherein the sensor control device further comprises a first aperture on a top surface of the housing of the sensor control device, wherein the sensor control device further comprises a second aperture on the bottom surface of the sensor control device, and wherein the sharp is configured to extend through the first aperture and the second aperture when the sharp carrier assembly, the sharp, the spring, the sensor carrier, the magnet, and the sensor control device are in the proximal position.

12. The assembly of claim 11, wherein the adhesive patch comprises a third aperture, and wherein the sharp is configured to extend through the third aperture when sharp carrier assembly, the sharp, the spring, the sensor carrier, the magnet, and the sensor control device are in the proximal position.

13. The assembly of claim 2, wherein the sensor carrier does not have one or more spring arms configured to retain the sensor control device.

* * * * *